United States Patent
Van Der Boom et al.

(10) Patent No.: US 9,611,218 B2
(45) Date of Patent: Apr. 4, 2017

(54) METAL-ORGANIC MATERIALS AND METHOD FOR PREPARATION

(71) Applicant: YEDA RESEARCH AND DEVELOPMENT CO. LTD., Rehovot (IL)

(72) Inventors: Milko E. Van Der Boom, Rishon Lezion (IL); Michal Lahav, Rehovot (IL); Renata Balgley, Rehovot (IL); Sreejith Shankar Poopanal, Rehovot (IL)

(73) Assignee: YEDA RESEARCH AND DEVELOPMENT CO., LTD., Rehovot (IL)

( * ) Notice: Subject to any disclaimer, the term of this patent is extended or adjusted under 35 U.S.C. 154(b) by 0 days.

(21) Appl. No.: 14/904,708

(22) PCT Filed: Jul. 13, 2014

(86) PCT No.: PCT/IL2014/050635
§ 371 (c)(1),
(2) Date: Jan. 13, 2016

(87) PCT Pub. No.: WO2015/008280
PCT Pub. Date: Jan. 22, 2015

(65) Prior Publication Data
US 2016/0152568 A1  Jun. 2, 2016

Related U.S. Application Data

(60) Provisional application No. 61/846,021, filed on Jul. 14, 2013.

(51) Int. Cl.
| | | |
|---|---|---|
| C07D 213/06 | (2006.01) | |
| B01J 20/02 | (2006.01) | |
| C07F 19/00 | (2006.01) | |
| C08G 83/00 | (2006.01) | |
| C08L 101/00 | (2006.01) | |
| C07F 15/00 | (2006.01) | |
| C07F 1/08 | (2006.01) | |
| C07F 3/06 | (2006.01) | |
| C07D 213/53 | (2006.01) | |
| B01J 20/22 | (2006.01) | |
| B01D 53/02 | (2006.01) | |

(52) U.S. Cl.
CPC ........... *C07D 213/06* (2013.01); *B01D 53/02* (2013.01); *B01J 20/02* (2013.01); *B01J 20/226* (2013.01); *C07D 213/53* (2013.01); *C07F 1/08* (2013.01); *C07F 3/06* (2013.01); *C07F 15/0066* (2013.01); *C07F 19/00* (2013.01); *C08G 83/00* (2013.01); *C08L 101/005* (2013.01); *B01D 2253/204* (2013.01)

(58) Field of Classification Search
None
See application file for complete search history.

(56) References Cited

FOREIGN PATENT DOCUMENTS

WO    WO 2013/058844 A1    4/2013

OTHER PUBLICATIONS

Kaminker, R. et al., Angewandte Chemie IEE 2011 vol. 50 pp. 3224-3226.*
Adisa et al. "Methane storage in molecular nanostructures", Nanoscale. Jun. 7, 2012;4(11):3295-307.
Ban et al. "Microporous and Mesoporous Materials", Microporous and Mesoporous Materials vol. 173, Jun. 2013, pp. 29-36.
Batten, S.R., CrystEnggComm, 2001, 18, 1-7.
Biradha et al. "Coordination Polymers Versus Metal-Organic Frameworks", Cryst. Growth Des., 2009, 9 (7), pp. 2969-2970.
Bridgeman, JA, "On the origin of paramagnetism in planar nickel(II) complexes", Dalton Trans. Apr. 21, 2008;(15):1989-92.
Carne-Sanchez et al. "Metal-organic frameworks: from molecules/metal ions to crystals to superstructures", Chemistry. Apr. 25, 2014;20(18):5192-201.
Chen et al. "Metal-organic frameworks with functional pores for recognition of small molecules", Acc Chem Res. Aug. 17, 2010;43(8):1 115-24.
Cho et al. "Growth-controlled formation of porous coordination polymer particles", J Am Chem Soc. Dec. 17, 2008;130(50):16943-6.
Choudhury et al. "Linear vs exponential formation of molecular-based assemblies", J Am Chem Soc. Jul. 14, 2010;132(27):9295-7.
Cook et al. "Metal-organic frameworks and self-assembled supramolecular coordination complexes: comparing and contrasting the design, synthesis, and functionality of metal-organic materials", Chem Rev. Jan. 9, 2013;113(1):734-77.
Evans et al. "Crystal engineering of NLO materials based on metal-organic coordination networks", Acc Chem Res. Jul. 2002;35(7):511-22.
Furukawa et al. "The chemistry and applications of metal-organic frameworks", Science. Aug. 30, 2013;341(6149):1230444.
Gao et al. "Growing crystalline zinc-1,3,5-benzenetricarboxylate metal-organic frameworks in different surfactants", Inorg Chem. Jan. 21, 2014;53(2):691-3.
Gu et al. "Size-dependent deformation of nanocrystalline Pt nanopillars", Nano Lett. Dec. 12, 2012;12(12):6385-92; including supporting information.
Guo et al. "Effect of cationic surfactants on structure and morphology of mesostructured MOFs", RSC Adv., 2012,2, 5424-5429.

(Continued)

*Primary Examiner* — Heidi Reese
(74) *Attorney, Agent, or Firm* — Mark S. Cohen; Pearl Cohen Zedek Latzer Baratz LLP

(57) ABSTRACT

The present invention provides metal-organic materials, more specifically organometallic polymers, comprising polypyridyl organic ligands such as tetrakis(4-(pyridin-4-ylethynyl)phenyl)methane, tetrakis(4-(2-(pyridin-4-yl)vinyl)phenyl)methane,3,5,7-tetrakis(4-(pyridin-4-ylethynyl) phenyl)adamantane or 1,3,5,7-tetrakis(4-(2-(pyridine-4-yl) vinyl)phenyl)adamantine, and metal ions structurally coordinated with said ligands, and having three-dimensional crystalline micro or sub-micro structure; as well as a method for the preparation thereof. These metal-organic materials are useful as adsorbents in processes for gas adsorption or separation.

31 Claims, 35 Drawing Sheets

(56) References Cited

OTHER PUBLICATIONS

Hasenknopf et al. "Self-assembly of a heteroduplex helicate from two different ligand strands and Cu(II) cations", Proc Natl Acad Sci U S A. Feb. 20, 1996;93(4):1397-400.
Hu, Moqing "Design, synthesis and Applications of Metal Organic Framework", A Thesis Submitted to the Faculty of the Department of Chemistry and Biochemistry Worcester Polytechnic Institute, 2011, pp. 1-80.
International Search Report for PCT Application No. PCT/IL2014/050635 dated Sep. 14, 2014.
Jeon et al. "Tröger's-base-derived infinite co-ordination polymer microparticles", Small. Jan. 2009;5(1):46-50.
Jung et al. "Monitoring shape transformation from nanowires to nanocubes and size-controlled formation of coordination polymer particles", Angew Chem Int Ed Engl. 2008;47(11):2049-51.
Kaminker et al. "Stepwise assembly of coordination-based metal-organic networks", J Am Chem Soc. Oct. 20, 2010;132(41):14554-61.
Kaminker et al. "Coordination-polymer nanotubes and spheres: a ligand-structure effect", Angew Chem Int Ed Engl. Mar. 28, 2011;50(14):3224-6; including Supplement—Supporting Information, pp. S1-S5.
Kitagawa et al. "Functional porous coordination polymers", Angew Chem Int Ed Engl. Apr. 26, 2004;43(18):2334-75.
Kondo et al. "Rational Synthesis of Stable Channel-Like Cavities with Methane Gas Adsorption Properties: [{Cu2(pzdc)2(L)}n] (pzdc=pyrazine-2,3-dicarboxylate; L=a Pillar Ligand)", Angewandte vol. 38, Issue 1-2 Jan. 15, 1999 pp. 140-143.
Lei et al. "Synthesis, Characterization, and Oxygen Sensing Properties of Functionalized Mesoporous SBA-15 and MCM-41 with a Covalently Linked Ruthenium(II) Complex", J. Phys. Chem. C, 2007, 111 (30), pp. 11291-11301.
Li et al. "Pyrite nanocrystals: shape-controlled synthesis and tunable optical properties viareversible self-assembly", J. Mater. Chem., 2011,21, 17946-17952.
Liu et al. "Hierarchically Nanostructured Coordination Polymer: Facile and Rapid Fabrication and Tunable Morphologies", Cryst. Growth Des., 2010, 10 (2), pp. 790-797.
Long et al. "The pervasive chemistry of metal-organic frameworks", Chem. Soc. Rev., 2009,38, 1213-1214.
Lu et al. "Shape controlled synthesis of superhydrophobic zinc coordination polymersparticles and their calcination to superhydrophobic ZnO", J. Mater. Chem., 2011,21, 8633-8639.
Lu et al. "Tuning the structure and function of metal-organic frameworks via linker design", Chem Soc Rev. Aug. 21, 2014;43(16):5561-93.
Mason et al. "Evaluating metal-organic frameworks for natural gas storage", Chemical Science; Journal vol. 5; Journal Issue: 1, Jan. 1, 2014, pp. 32-51.
Masoomi, M.Y. "Morphological study and potential applications of nano metal-organic coordination polymers", Morsali, A., RSC Adv., 2013, 3, 19191-19218.
Murray et al. "Colloidal synthesis of nanocrystals and nanocrystal superlattices", IBM Journal of Research and Development 45.1 (Jan. 2001): 47-56.
Ni et al. "Rapid production of metal-organic frameworks via microwave-assisted solvothermal synthesis", J Am Chem Soc. Sep. 27, 2006;128(38):12394-5.
Noorduin et al. "Rationally designed complex, hierarchical microarchitectures", Science. May 17, 2013;340(6134):832-7.
Oh et al. "Chemically tailorable colloidal particles from infinite coordination polymers", Nature. Dec. 2005 1;438(7068):651-4.
Oh et al. "Ion exchange as a way of controlling the chemical compositions of nano- and microparticles made from infinite coordination polymers", Angew Chem Int Ed Engl. Aug. 18, 2006;45(33):5492-4.
Park et al. "Self-supported organometallic rhodium quinonoid nanocatalysts for stereoselective polymerization of phenylacetylene", J Am Chem Soc. Jul. 12, 2006;128(27):8740-1.

Pevzner et al. "Confinement-guided shaping of semiconductor nanowires and nanoribbons: "writing with nanowires"", Nano Lett. Jan. 11, 2012;12(1):7-12.
Ranft et al. "Additive-mediated size control of MOF nanoparticles", CrystEngComm, 2013,15, 9296-9300.
Rieter et al. "Nanoscale metal-organic frameworks as potential multimodal contrast enhancing agents", J Am Chem Soc. Jul. 19, 2006;128(28):9024-5.
Roberts et al. "The relationship between Young's modulus of elasticity of organic solids and their molecular structure", Powder Technology vol. 65, Issues 1-3, Mar. 1991, pp. 139-146.
Rowsell et al. "Strategies for hydrogen storage in metal—organic frameworks", Angew Chem Int Ed Engl. Jul. 25, 2005;44(30):4670-9.
Sader et al. "Calibration of rectangular atomic force microscope cantilevers", Rev. Sci. Instrum. 70, 3967 (1999).
Schilling et al. "Fourfold Suzuki-Miyaura and Sonogashira Cross-Coupling Reactions on Tetrahedral Methane and Adamantane Derivatives", European Journal of Organic Chemistry vol. 2011, Issue 9, pp. 1743-1754, Mar. 2011.
Seo et al. "A homochiral metal-organic porous material for enantioselective separation and catalysis", Nature. Apr. 27, 2000;404(6781):982-6.
Shankar et al. "Homogeneously Micro-structured Metal-Organic Coordination Polymers", 4th National Graduate Student, Symposium in Organic Chemistry, Sep. 10, 2012, 2 pages.
Shi et al. "Facile synthesis of shape and size tunable porphyrinoid coordination polymers: from copper porphyrin nanoplates to microspindles", Chem Commun (Camb). May 7, 2011;47(17):5055-7.
Shirman et al. "Halogen-Bonded Supramolecular Assemblies Based on Phenylethynyl Pyridine Derivatives: Driving Crystal Packing through Systematic Chemical Modifications", Cryst. Growth Des., 2008, 8 (8), pp. 3066-3072.
Sindoro et al. "Colloidal-sized metal-organic frameworks: synthesis and applications", Acc Chem Res. Feb. 18, 2014;47(2):459-69.
Smulders et al. "Building on architectural principles for three-dimensional metallosupramolecular construction", Chem Soc Rev. Feb. 21, 2013;42(4):1728-54.
Spokoyny et al. "Infinite coordination polymer nano- and microparticle structures", Chem Soc Rev. May 2009;38(5):1218-27.
Stock et al. "Synthesis of metal-organic frameworks (MOFs): routes to various MOF topologies, morphologies, and composites", Chem Rev. Feb. 8, 2012;112(2):933-69.
Sun et al. "Coordination-induced formation of submicrometer-scale, monodisperse, spherical colloids of organic-inorganic hybrid materials at room temperature", J Am Chem Soc. Sep. 28, 2005;127(38):13102-3.
Tabellion et al. "Discrete supramolecular architecture vs crystal engineering: the rational design of a platinum-based bimetallic assembly with a chairlike structure and its infinite, copper analogue", J Am Chem Soc. Aug. 8, 2001;123(31):7740-1.
Tabor et al. "Surface forces and surface interactions", Journal of Colloid and Interface Science vol. 58, Issue 1, Jan. 1977, pp. 2-13.
Tao et al. "Shape Control of Colloidal Metal Nanocrystals", Small vol. 4, Issue 3 Mar. 3, 2008, pp. 310-325.
Thompson et al. "Molybdenum complexes of two new pyridyl-based tetranucleating bridging ligands with unusual geometries: one with a tetrahedral donor set, and one containing two orthogonal non-interacting components", Inorganica Chimica Acta vol. 256, Issue 2, Mar. 31, 1997, pp. 331-334.
Tomasik, P., Ratajewicz, Z., Newkome, G.R., Strekowski, L.E., In Chemistry of Heterocyclic Compounds: Pyridine Metal Complexes (Part 6, vol. 14). (John Wiley & Sons, Inc., 2008).
Tuxen et al. "Size-dependent dissociation of carbon monoxide on cobalt nanoparticles", J Am Chem Soc. Feb. 13, 2013;135(6):2273-8.
Wang et al. "Facile synthesis of size-tunable micro-octahedra via metal-organic coordination", Chem Commun (Camb). Sep. 28, 2009;(36):5457-9.
Wang et al. "Metal-organic frameworks as a tunable platform for designing functional molecular materials", J Am Chem Soc. Sep. 11, 2013;135(36):13222-34.

(56) References Cited

OTHER PUBLICATIONS

Wei et al. "Nucleobase-Metal Hybrid Materials: Preparation of Submicrometer-Scale, Spherical Colloidal Particles of Adenine-Gold(III) via a Supramolecular Hierarchical Self-Assembly Approach", Chem. Mater., 2007, 19 (12), pp. 2987-2993.

Whitesides et al. "Self-assembly at all scales", Science. Mar. 29, 2002;295(5564):2418-21.

Yaghi et al. "Reticular synthesis and the design of new materials", Nature. Jun. 12, 2003;423(6941):705-14.

Zhang et al. "Metal-ion-coated graphitic nanotubes: controlled self-assembly of a pyridyl-appended gemini-shaped hexabenzocoronene amphiphile", Angew Chem Int Ed Engl. 2009;48(26):4747-50.

Zhao et al. "Hysteretic adsorption and desorption of hydrogen by nanoporous metal-organic frameworks", Science. Nov. 5, 2004;306(5698):1012-5.

Zhao et al. "Two Dawson-templated three-dimensional metal-organic frameworks based on oxalate-bridged binuclear cobalt(II)/Nickel(II) SBUs and Bpy linkers", Inorg Chem. Aug. 18, 2008:47(16):7133-8.

Zhao et al. "Tuning the topology and functionality of metal-organic frameworks by ligand design", Acc Chem Res. Feb. 15, 2011;44(2):123-33.

Supplementary Search Report for European Application No. 14825682.9 dated Jan. 26, 2017.

\* cited by examiner

Fig. 1A
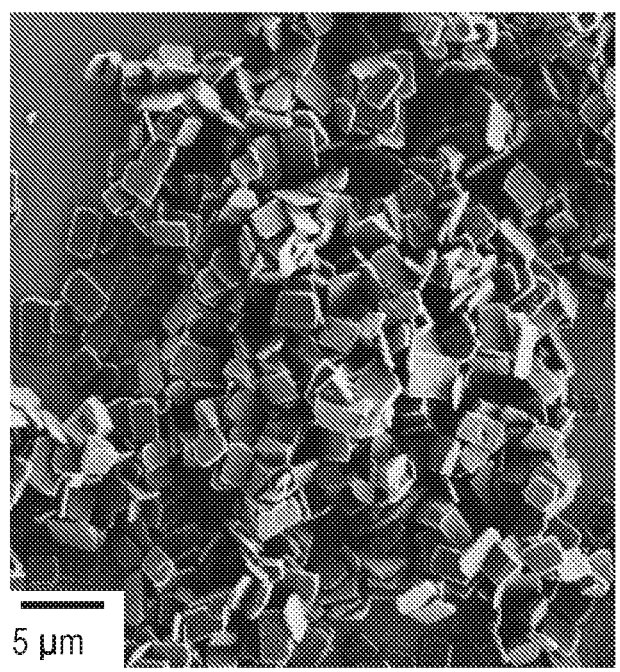
Fig. 1B
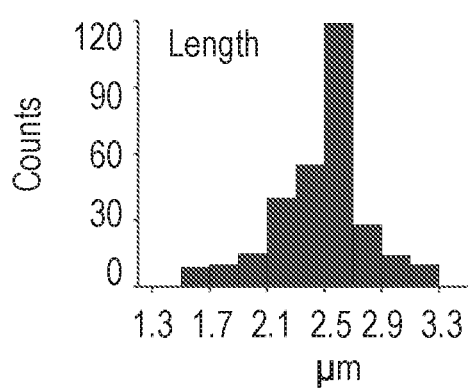
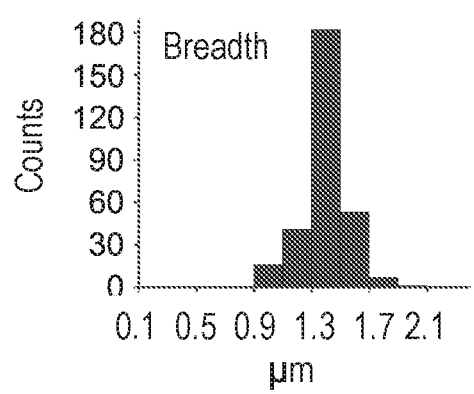

Fig. 2A
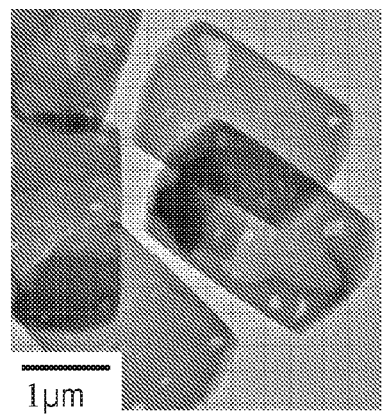
Fig. 2B
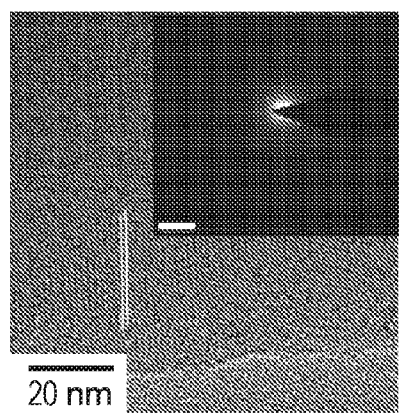
Fig. 3
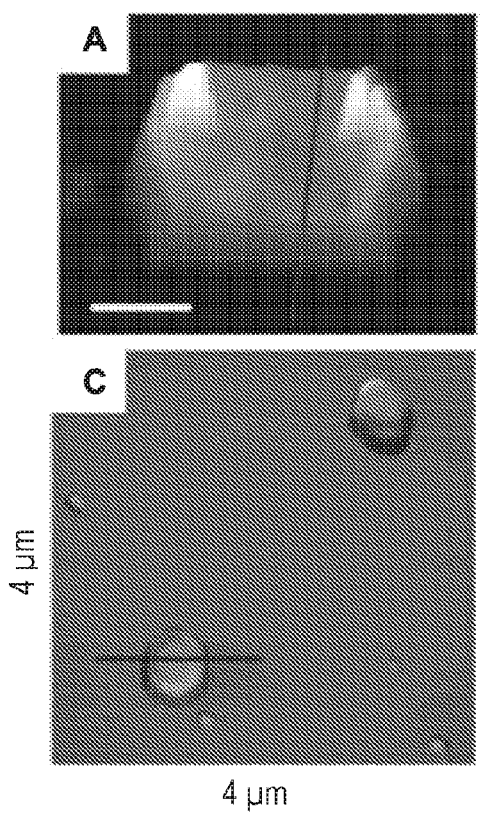
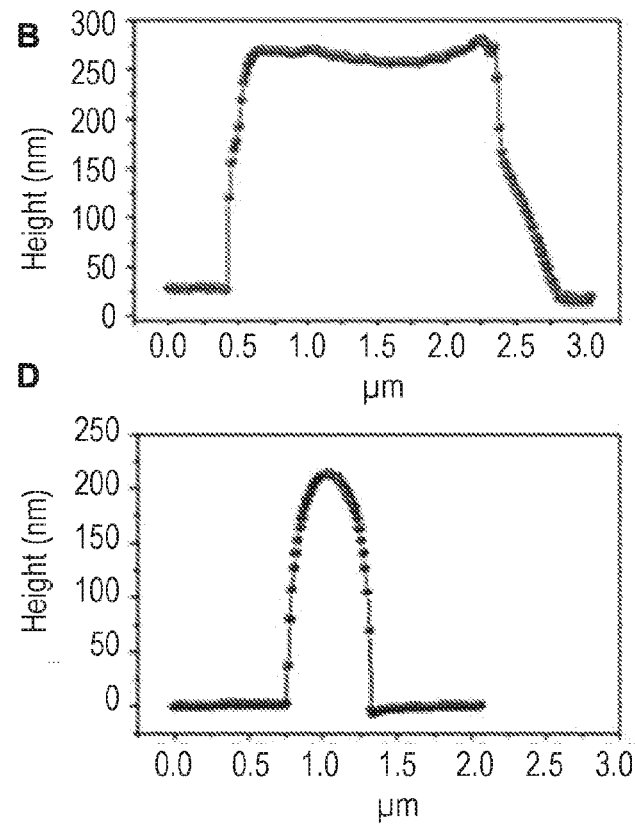

METAL-ORGANIC MATERIALS AND METHOD FOR PREPARATION

CROSS-REFERENCE TO RELATED APPLICATIONS

This application is a National Phase Application of PCT International Application No. PCT/IL2014/050635, international Filing Date Jul. 13, 2014, claiming priority of U.S. Provisional Patent Application No. 61/846,021, filed Jul. 14, 2013 which are hereby incorporated by reference.

TECHNICAL FIELD

The present invention provides metal-organic materials comprising polypyridyl organic ligands and metal ions structurally coordinated with said ligands, and a method for the preparation thereof.

ABBREVIATIONS

AFM, atomic force microscope; CP, coordination polymer; DMF, dimethylformamide; EDS, energy dispersive spectroscopy; FC, field cooled; FT-IR, infrared Fourier transform spectrophotometer; MOF, metal-organic framework; RT, room temperature; RTP, rapid thermal processing; SAED, selected area electron diffraction; SEM, scanning electron microscope; SQUID, superconducting quantum interference device; TEM, transmission electron microscope; TGA, thermogravimetric analysis; XRD, X-ray diffraction; ZFC, zero field cooled;

BACKGROUND ART

Research related to metal-organic frameworks (MOFs) as well as coordination polymers (CPs) (for a perspective understanding of the differences between the terms CP, MOF and hybrid organic-inorganic materials, see Biradha et al., 2009) has been treated with overwhelming interest by the scientific community of chemists and physicists due to tunable properties of these molecular assemblies by controlling their growth, size and shape, and their potential applications in the fields of catalysis, gas storage, separation, recognition and purification, optics, sensors, etc. (Zhao et al., 2004; Yaghi et al., 2003; Seo et al., 2000; Kitagawa et al., 2004; Evans and Lin, 2002; Rowsell and Yaghi, 2005; Tabellion et al., 2001; Lei et al., 2007; Zhao et al., 2008; Chen et al., 2010). It was in 1964 that J. C. Bailar defined the term "coordination polymer" (Bailar, 1964) and a wide variety of techniques such as solvothermal (Jung and Oh, 2008; Ni and Masel, 2006), precipitation (Oh and Mirkin, 2005; Oh and Mirkin, 2006; Sun et al., 2005; Park et al., 2006; Wei et al., 2007) and reverse microemulsion (Rieter et al., 2006) methods have been employed in the generation of shape selective nano and micro structured CPs (Wang et al., 2009; Shi et al., 2011; Liu et al., 2010; Lu et al., 2011; Li et al., 2011; Cho et al., 2008).

Structural uniformity is a prerequisite for many real-world applications that involve oriented fabrication of various materials, often in size-confined regimes (Tuxen et al., 2013). At the same time, structural diversity can lead to control of desired physical and chemical properties (Noorduin et al., 2013; Pevzner et al., 2012; Whitesides and Grzybowski, 2002; Masoomi and Morsali, 2013; Gu et al., 2012). Molecular self-assembly allows the construction of composite superstructures with unique structure and properties. Size and shape confined synthesis of such composites are advantageous for their intrinsic and complex multi-functionalities, allows addressing properties of individual components and the combination thereof, and the possibilities of their spatial integration into devices and onto surfaces (Carné-Sánchez et al., 2014). Needless to say "structure dictates function at all scales" (Tao et al., 2008).

Due to their unique, often porous structures and special properties achieved through synthetic tunability, MOFs have been actively studied over the last few decades (Furukawa et al., 2013; Cook et al., 2013; Long and Yaghi, 2009). However, control over their spatial topologies at the micro and nano levels is still limited and difficult to achieve (Stock and Biswas, 2011; Sindoro et al., 2014). Many variables, e.g., anions, solvents, and electronic configuration, play a key role in the formation of geometrically well-defined and uniform shapes. Thus far, the shapes of MOFs are limited to simple polyhedra (Sindoro et al., 2014).

SUMMARY OF INVENTION

It has been found, in accordance with the present invention, that metal-organic materials, in particular such materials comprising tetrahedral polypyridyl ligands and transition metal ions coordinated therewith, having diverse three-dimensional (sub)-microstructures with a high degree of uniformity, can be prepared by a particular solvothermal synthesis, while controlling the uniformity and topology of said microstructures without the addition of any surfactants or modulators.

In one aspect, the present invention thus provides a metal-organic material comprising at least two ligands, at least two metal ions structurally coordinated with said ligands, and counter anions, wherein each one of the ligands is of the general formula I:

$$R_1(R_2-R_3-R_4)_4, \qquad I$$

wherein
$R_1$ is C, i.e.,

or adamantane-1,3,5,7-tetrayl, i.e.,

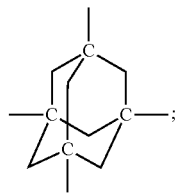

$R_2$ and $R_3$ each independently is absent, or selected from $(C_1-C_8)$alkylene, $(C_2-C_8)$alkenylene, $(C_2-C_8)$alkynylene, cycloalkylene, heterocycloalkylene, arylene-diyl, heteroarylene-diyl, or —N═N—, wherein said alkylene, alkenylene, alkynylene, cycloalkylene, heterocycloalkylene, arylene-diyl and heteroarylene-diyl may optionally be substituted with one or more groups each independently selected from halogen, —OR$_6$, —CN, —COR$_6$, —COOR$_6$, —CON(R$_6$)$_2$, —OCOOR$_6$, —OCON(R$_6$)$_2$, —(C$_1$-C$_4$)alkyl, —O—(C$_1$-C$_4$)alkyl, —(C$_1$-C$_4$)alkylene-COOR$_6$, —N(R$_6$)$_2$, —NO$_2$, —SR$_6$, —SO$_2$R$_6$, or —S(═O)R$_6$, or said alkylene, alkenylene and alkynylene may optionally be interrupted by one or more identical or different heteroatoms selected from S, O or N, and/or at least one group selected from —N=N—, —NH—CO—, —CO—NH—, —N($C_1$-$C_4$alkyl)-, —N($C_6$-$C_{10}$aryl)-, or —($C_6$-$C_{10}$)arylene-diyl-, wherein $R_6$ each independently is H, ($C_1$-$C_4$)alkyl, ($C_2$-$C_4$)alkenyl or ($C_2$-$C_4$)alkynyl;

$R_4$ each independently is a pyridyl of the formula II, 2,2'-bipyridyl of the formula III, or 2,2':6',2''-terpyridyl of the formula IV, linked through a carbon atom thereof; and

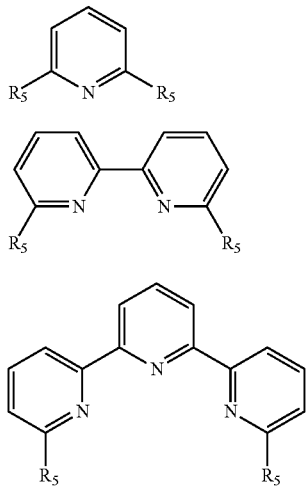

$R_5$ each independently is H, —COOH, —CN, —OH, or —$NH_2$.

In another aspect, the present invention relates to a method for the preparation of a metal-organic material as defined above, comprising the steps of:
(i) providing (a) an organic solution or suspension of a metal salt consisting of anions and said metal ions; and (b) an organic solution or suspension of said ligands, in a pressure vessel, e.g., a glass pressure vessel;
(ii) sealing and keeping said pressure vessel for a period of time with exclusion of light and without stirring, optionally while heating to a temperature ranging from 60° C. to 120° C. for the whole said period of time or a part thereof and then gradually cooling, thereby reacting said metal ions with said ligands to obtain said metal-organic material as a precipitate; and
(iii) collecting said precipitate.

In yet another aspect, the present invention relates to use of a metal-organic material as defined above as an adsorbent in a process for gas adsorption or gas separation.

In still another aspect, the present invention relates to a process for gas adsorption or gas separation by adsorbing said gas to an adsorbent, the improvement wherein said adsorbent is a metal-organic material as defined above.

BRIEF DESCRIPTION OF DRAWINGS

FIGS. 1A-1B show (1A) SEM image of the brick-like microstructures (NiClL1); and (1B) distribution of length and breadth of the microbricks. Each bar corresponds to the counts in the interval x to (x+0.2) µm. AFM measurements indicated a thickness of 200-300 nm.

FIGS. 2A-2B show TEM image of the brick-like microstructures (NiClL1) (2A); and TEM image showing the diffraction grating (inset–electron diffraction, scale bar=1 $nm^{-1}$) (2B).

FIGS. 3A-3D show AFM topography of NiClL1 (scale bar=1 µm) (3A); height profile corresponding to the vertical line in 3A of an individual crystallite (3B); AFM topography of NiBrL2 (3C); and height profile corresponding to the horizontal line in 3C of an individual crystallite (3D).

DETAILED DESCRIPTION OF THE INVENTION

Figure 4:
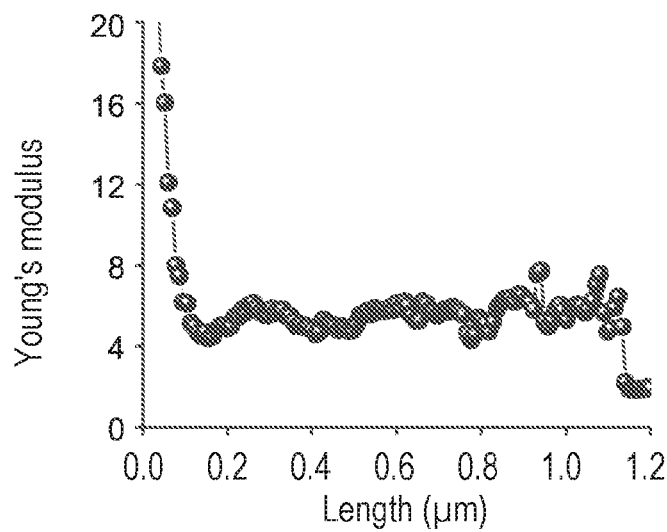
FIG. 4 shows Young's Modulus across one of the randomly chosen brick-like mucrostructures, as measured by an AFM.

In one aspect, the present invention provides a metal-organic material as defined above, i.e., a metal-organic material comprising at least two ligands each of the general formula I as defined above, at least two metal ions structurally coordinated with said ligands, and counter anions.

The term "metal-organic material" or "metal-organic framework (MOF)" as used herein refers to a particular type of a coordination polymer, more specifically an organometallic polymer, containing metal cations, preferably transition metal cations, coordinated to organic ligands each of the general formula I to form one-, two-, or three-dimensional structures that can be porous, wherein the choice of metal cation and organic ligand dictates the structure and hence properties of the MOF. More particularly, the MOF is a coordination network with organic ligands containing potential voids, wherein the term "coordination network" refers to a coordination oligomer extending, through repeating coordination entities, either in one dimension but with cross-links between two or more individual chains, loops, or spiro-links, or in two or three dimensions (see also Biradha et al., 2009).

The term "halogen", as used herein, includes fluoro, chloro, bromo, and iodo.

The term "alkane", as used herein, refers to a straight or branched, or cyclic (including bicyclic), saturated hydrocarbon having preferably 5-14, carbon atoms, and includes, e.g., pentane, hexane, cyclohexane, heptane, cycloheptane, octane, cyclooctane, nonane, decane, decalin, and the like.

The term "alkanol", as used herein, refers to an alkane having preferably 1-10 carbon atoms and containing a hydroxy/alcohol functional group (—OH) in place of a hydrogen atom, and includes, e.g., methanol, ethanol, isopropanol, n-butanol, sec-butanol, isobutanol, pentanol, hexanol, and the like.

The term "alkyl", as used herein, typically means a straight or branched hydrocarbon radical having preferably 1-8, more preferably 1-4, carbon atoms, and includes, e.g., methyl, ethyl, n-propyl, isopropyl, n-butyl, isobutyl, sec-butyl, tert-butyl, n-pentyl, isopentyl, 2,2-dimethylpropyl, n-hexyl, n-heptyl, n-octyl, and the like.

The term "alkylene", as used herein, refers to a linear divalent hydrocarbon chain having preferably 1-8 carbon atoms and includes, e.g., methylene, ethylene, propylene, butylene, pentylene, hexylene, heptylene, octylene, and the like. The terms "alkenylene" and "alkynylene" typically mean linear divalent hydrocarbon radicals having preferably 2-8 carbon atoms and at least one double or triple bond, respectively. Non-limiting examples of such alkenylenes include ethenylene, 1,3-propenylene, 1,4-but-1-enylene, 1,4-but-2-enylene, 1,4-but-3-enylene, 1,5-pent-1-enylene, 1,5-pent-2-enylene, 1,5-pent-3-enylene, 1,5-pent-4-enylene, 1,6-hex-1-enylene, 1,6-hex-2-enylene, 1,6-hex-3-enylene, 1,6-hex-4-enylene, 1,6-hex-5-enylene, 1,7-hept-1-enylene, 1,7-hept-2-enylene, 1,7-hept-3-enylene, 1,7-hept-4-enylene, 1,7-hept-5-enylene, 1,7-hept-6-enylene, 1,8-oct-1-enylene, 1,8-oct-2-enylene, 1,8-oct-2-enylene, 1,8-oct-3-enylene, 1,8-oct-4-enylene, 1,8-oct-5-enylene, 1,8-oct-6-enylene, 1,8-oct-7-enylene, and the like; and examples of such alkynylenes include, without limiting, ethynylene, 1,3-propynylene, 1,4-but-1-ynylene, 1,4-but-2-ynylene, 1,4-but-3-ynylene, 1,5-pent-1-ynylene, 1,5-pent-2-ynylene, 1,5-pent-3-ynylene, 1,5-pent-4-ynylene, 1,6-hex-1-ynylene, 1,6-hex-2-ynylene, 1,6-hex-3-ynylene, 1,6-hex-4-ynylene, 1,6-hex-5-ynylene, 1,7-hept-1-ynylene, 1,7-hept-2-ynylene, 1,7-hept-3-ynylene, 1,7-hept-4-ynylene, 1,7-hept-5-ynylene, 1,7-hept-6-ynylene, 1,8-oct-1-ynylene, 1,8-oct-2-ynylene, 1,8-oct-2-ynylene, 1,8-oct-3-ynylene, 1,8-oct-4-ynylene, 1,8-oct-5-ynylene, 1,8-oct-6-ynylene, 1,8-oct-7-ynylene, and the like.

The term "cycloalkylene", as used herein, typically means a mono- or bicyclic saturated divalent hydrocarbon radical having preferably 3-10 carbon atoms such as cyclopropylene, cyclobutylene, cyclopentylene, cyclohexylene, cycloheptylene, cyclooctylene, cyclodecylene, bicyclo[3.2.1]octane-diyl, bicyclo[2.2.1]heptane-diyl, and the like. The term "heterocycloalkylene" refers to a cycloalkylene, in which at least one of the ring carbon atoms is replaced by a heteroatom selected from N, O or S.

The term "aryl", as used herein, denotes an aromatic carbocyclic group, preferably having 6-14 carbon atoms, consisting of a single ring or multiple rings either condensed or linked by a covalent bond such as, but not limited to, phenyl, naphthyl, phenanthryl, and biphenyl. The term "arylene-diyl" refers to a divalent group derived from an arene by removal of a hydrogen atom from two ring carbon atoms. Non-limiting examples of arylene-diyls include benzene-1,3-diyl, benzene-1,4-diyl, naphthalene-diyl, phenanthrene-2,7-diyl, biphenyl-4,4'-diyl, and the like.

The term "heteroarylene-diyl" refers to a divalent group derived from a mono- or polycyclic heteroaromatic ring containing one to three, preferably 1-2, heteroatoms selected from the group consisting of N, O and S, by removal of a hydrogen atom from two ring atoms. When the heteroarylene-diyl is a monocyclic heteroaromatic ring, it is preferably a divalent group of a 5-6-membered ring such as, but not limited to, pyrrole-2,5-diyl, pyrrole-3,5-diyl, furane-2,5-diyl, furane-3,5-diyl, thiophene-2,5-diyl, thiophene-3,5-diyl, thiazine-2,5-diyl, thiazine-3,6-diyl, pyrazole-1,3-diyl, pyrazole-1,4-diyl, pyrazole-3,5-diyl, pyrazine-2,5-diyl, pyrazine-2,6-diyl, imidazole-1,4-diyl, imidazole-2,4-diyl, imidazole-2,5-diyl, oxazole-2,4-diyl, oxazole-2,5-diyl, isoxazole-3,5-diyl, thiazole-2,4-diyl, thiazole-2,5-diyl, isothiazole-3,5-diyl, pyridine-2,4-diyl, pyridine-3,6-diyl, pyrimidine-2,4-diyl, pyrimidine-2,5-diyl, 1,2,3-triazine-4,6-diyl, 1,3,4-triazine-2,5-diyl, 1,3,4-triazine-2,6-diyl, 1,3,5-triazine-2,4-diyl, and the like. Examples of polycyclic heteroarylene-diyls composed of two rings include, without being limited to, benzofurane-2,5-diyl, benzofurane-2,6-diyl, isobenzofurane-2,4-diyl, isobenzofurane-2,5-diyl, benzothiene-2,5-diyl, benzothiene-2,6-diyl, indole-2,5-diyl, indole-2,6-diyl, quinoline-2,6-diyl, quinoline-2,7-diyl, quinoline-3,6-diyl, quinoline-3,7-diyl, isoquinoline-3,6-diyl, isoquinoline-3,7-diyl, imidazo[1,2-a]pyridine-2,6-diyl, imidazo[1,2-a]pyridine-2,7-diyl, benzimidazole-2,5-diyl, benzimidazole-2,6-diyl, benzthiazole-2,5-diyl, benzthiazole-2,6-diyl, benzoxazole-2,5-diyl, benzoxazole-2,6-diyl, pyrido[1,2-a]pyrimidine-2,7-diyl, pyrido[1,2-a]pyrimidine-2,8-diyl, pyrido[1,2-a]pyrimidine-3,7-diyl, pyrido[1,2-a]pyrimidine-3,7-diyl, 1,3-benzodioxin-2,6-diyl, 1,3-benzodioxin-2,7-diyl, and the like.

The alkylene, alkenylene, alkynylene, cycloalkylene, heterocycloalkylene, arylene-diyl and heteroarylene-diyl may optionally be substituted with one or more groups each independently selected from halogen, —$OR_6$, —CN, —$COR_6$, —$COOR_6$, —$CON(R_6)_2$, —$OCOOR_6$, —$OCON(R_6)_2$, —$(C_1$-$C_4)$alkyl, —O—$(C_1$-$C_4)$alkyl, —$(C_1$-$C_4)$alkylene-$COOR_6$, —$N(R_6)_2$, —$NO_2$, —$SR_6$, —$SO_2R_6$, or —$S(=O)R_6$, or said alkylene, alkenylene and alkynylene may optionally be interrupted by one or more, e.g., one or two, identical or different heteroatoms selected from S, O or N, and/or at least one group, e.g., one, two or three groups, each independently selected from —N=N—, —NH—CO—, —CO—NH—, —N($C_1$-$C_4$alkyl)-, —N($C_6$-$C_{10}$aryl)-, or —($C_6$-$C_{10}$)arylene-diyl-, wherein $R_6$ each independently is H, $(C_1$-$C_4)$alkyl, $(C_2$-$C_4)$alkenyl or $(C_2$-$C_4)$alkynyl.

In certain embodiments, the metal-organic material of the present invention is a material of the general formula I as defined above, wherein $R_2$ and $R_3$ each independently is absent, or selected from $(C_1$-$C_8)$alkylene, $(C_2$-$C_8)$alkenylene, $(C_2$-$C_8)$alkynylene, cycloalkylene, heterocycloalkylene, arylene-diyl, heteroarylene-diyl, or —N=N—, wherein said alkylene, alkenylene, alkynylene, cycloalkylene, heterocycloalkylene, arylene-diyl and heteroarylene-diyl may optionally be substituted with one or more groups each independently selected from halogen, —$OR_6$, —CN, —$COR_6$, —$COOR_6$, —$CON(R_6)_2$, —$OCOOR_6$, —$OCON(R_6)_2$, —$(C_1$-$C_4)$alkyl, —O—$(C_1$-$C_4)$alkyl, —$(C_1$-$C_4)$alkylene-$COOR_6$, —$N(R_6)_2$, —$NO_2$, —$SR_6$, —$SO_2R_6$, or —$S(=O)R_6$, wherein $R_6$ is H, or said alkylene, alkenylene and alkynylene may optionally be interrupted by one or more identical or different heteroatoms selected from S, O or N, and/or at least one group selected from —N=N—, —NH—CO—, —CO—NH—, —N($C_1$-$C_4$alkyl)-, —N($C_6$-$C_{10}$aryl)-, or —($C_6$-$C_{10}$)arylene-diyl-.

In certain particular such embodiments, $R_2$ and $R_3$ each independently is absent, or selected from $(C_1$-$C_4)$alkylene, $(C_2$-$C_4)$alkenylene, $(C_2$-$C_4)$alkynylene, cycloalkylene, heterocycloalkylene, arylene-diyl, heteroarylene-diyl, or —N=N—, wherein said alkylene, alkenylene, alkynylene, cycloalkylene, heterocycloalkylene, arylene-diyl and heteroarylene-diyl may optionally be substituted with halogen, —OH, —CN, —COH, —COOH, —$CONH_2$, —OCOOH, —$OCONH_2$, —$(C_1$-$C_2)$alkyl, —O—$(C_1$-$C_2)$alkyl, —$(C_1$-$C_2)$alkylene-COOH, —$NH_2$, —$NO_2$, —SH, —$SO_2H$, or —S(=O)H, or said alkylene, alkenylene and alkynylene may optionally be interrupted by one or more identical or different heteroatoms selected from S, O or N, and/or at least one group selected from —N=N—, —NH—CO—, —CO—NH—, —N($C_1$-$C_2$alkyl)-, —N($C_6$aryl)-, or —($C_6$)arylene-diyl-.

In more particular such embodiments, the metal-organic material of the present invention is a material of the general formula I, wherein $R_2$ and $R_3$ each independently is absent, or selected from $(C_1$-$C_4)$alkylene, $(C_2$-$C_4)$alkenylene, $(C_2$-$C_4)$alkynylene, arylene-diyl, or heteroarylene-diyl, e.g., wherein (i) one of $R_2$ and $R_3$ is absent and another of $R_2$ and $R_3$ is $(C_2$-$C_4)$alkylene, $(C_2$-$C_4)$alkenylene, $(C_2$-$C_4)$alkynylene, arylene-diyl, or heteroarylene-diyl; (ii) one of $R_2$ and $R_3$ is $(C_2$-$C_4)$alkylene, $(C_2$-$C_4)$alkenylene or $(C_2$-$C_4)$alkynylene, and another of $R_2$ and $R_3$ is arylene-diyl, or heteroarylene-diyl; or (iii) both $R_2$ and $R_3$ are absent. Certain specific such embodiments are those wherein $R_2$ is $(C_2$-$C_4)$alkenylene or $(C_2$-$C_4)$alkynylene, and $R_3$ is $(C_6)$arylene-diyl; or $R_2$ is $(C_6)$arylene-diyl, and $R_3$ is $(C_2$-$C_4)$alkenylene or $(C_2$-$C_4)$alkynylene.

In certain embodiments, the metal-organic material of the present invention is a material of the general formula I as defined above, wherein $R_4$ each independently is a pyridyl of the formula II, wherein $R_5$ each independently is H, —COOH, —CN, —OH, or —$NH_2$, preferably H or —COOH.

In certain embodiments, the metal-organic material of the present invention is a material of the general formula I as defined above, wherein $R_1$ is C or adamantane-1,3,5,7-tetrayl; $R_2$ and $R_3$ each independently is absent, or selected from $(C_1$-$C_4)$alkylene, $(C_2$-$C_4)$alkenylene, $(C_2$-$C_4)$alkynylene, cycloalkylene, heterocycloalkylene, arylene-diyl, heteroarylene-diyl, or —N=N—, wherein said alkylene, alkenylene, alkynylene, cycloalkylene, heterocycloalkylene, arylene-diyl and heteroarylene-diyl may optionally be substituted with one or more groups each independently selected from halogen, —$OR_6$, —CN, —$COR_6$, —$COOR_6$, —$CON(R_6)_2$, —$OCOOR_6$, —$OCON(R_6)_2$, —$(C_1$-$C_4)$alkyl, —O—$(C_1$-$C_4)$alkyl, —$(C_1$-$C_4)$alkylene-$COOR_6$, —$N(R_6)_2$, —$NO_2$, —$SR_6$, —$SO_2R_6$, or —$S(=O)R_6$, wherein $R_6$ is H, or said alkylene, alkenylene and alkynylene may optionally be interrupted by one or more identical or different heteroatoms selected from S, O or N, and/or at least one group selected from —N=N—, —NH—CO—, —CO—NH—, —N($C_1$-$C_2$alkyl)-, —N($C_6$aryl)-, or —($C_6$)arylene-diyl-; $R_4$ each independently is pyridyl of the formula II; and $R_5$ each independently is H, —COOH, —CN, —OH, or —$NH_2$, preferably H or —COOH.

In certain particular such embodiments, $R_2$ and $R_3$ each independently is absent, or selected from ($C_1$-$C_4$)alkylene, ($C_2$-$C_4$)alkenylene, ($C_2$-$C_4$)alkynylene, arylene-diyl, or heteroarylene-diyl; $R_4$ is a pyridyl of the formula II linked through the carbon atom para to the nitrogen atom; and $R_5$ is H or —COOH. In more particular such embodiments, the metal-organic material of the present invention is a material of the general formula I, wherein (i) one of $R_2$ and $R_3$ is absent and another of $R_2$ and $R_3$ is ($C_2$-$C_4$)alkylene, ($C_2$-$C_4$)alkenylene, ($C_2$-$C_4$)alkynylene, arylene-diyl, or heteroarylene-diyl; (ii) one of $R_2$ and $R_3$ is ($C_2$-$C_4$)alkylene, ($C_2$-$C_4$)alkenylene or ($C_2$-$C_4$)alkynylene, and another of $R_2$ and $R_3$ is arylene-diyl, or heteroarylene-diyl; or (iii) both $R_2$ and $R_3$ are absent, e.g., wherein $R_2$ is ($C_2$-$C_4$)alkenylene or ($C_2$-$C_4$)alkynylene, and $R_3$ is ($C_6$)arylene-diyl; or $R_2$ is ($C_6$)arylene-diyl, and $R_3$ is ($C_2$-$C_4$)alkenylene or ($C_2$-$C_4$)alkynylene. Certain specific such embodiments are those wherein $R_2$ is ($C_6$)arylene-diyl; and $R_3$ is ($C_2$)alkenylene or ($C_2$)alkynylene, i.e., metal-organic materials comprising at least two metal ions structurally coordinated with at least two polypyridyl ligands each of the general formula I, consisting of C or adamantane-1,3,5,7-tetrayl linked to four identical "arms" each being (4-(2-(pyridin-4-yl)vinyl)phenyl) or (4-(pyridin-4-ylethynyl)phenyl), respectively.

In specific embodiments, the metal-organic material of the present invention is a material of the general formula I, wherein (i) $R_1$ is C, and each one of said ligands is tetrakis(4-(pyridin-4-ylethynyl)phenyl)methane or tetrakis(4-(2-(pyridin-4-yl)vinyl)phenyl)methane, herein identified ligands L1 and L2, respectively; or (ii) $R_1$ is adamantane-1,3,5,7-tetrayl, and each one of said ligands is 1,3,5,7-tetrakis(4-(pyridin-4-ylethynyl)phenyl)adamantane or 1,3,5,7-tetrakis(4-(2-(pyridin-4-yl)vinyl)phenyl)adamantane, herein identified ligands L3 and L4, respectively (see Appendix).

In certain embodiments, the metal ions comprised within the metal-organic material of the present invention are ions of a transition metal such as Os, Ru, Fe, Pt, Pd, Ni, Ir, Rh, Zn, Co, Cu, Re, Tc, Mn, V, Nb, Ta, Hf, Zr, Cr, Mo, W, Ti, Sc, Ag, Au, Y, or a combination thereof. In particular such embodiments, the metal ions are ions of one or more, i.e., a combination, of Ni, Cu, Pd or Zn.

In certain embodiments, the counter anions comprised within the metal-organic material of the present invention are selected from inorganic anions, organic anions, or a combination thereof. Examples of inorganic anions include, without being limited to, $F^-$, $Cl^-$, $Br^-$, $I^-$, $NO_3^-$, $PF_6^-$, $BF_4^-$, $OH^-$, $ClO_4^-$, $SO_3^-$, and $CN^-$; and non-limiting examples of organic anions include alkylCOO$^-$, preferably acetoxy (OAc), $CF_3COO^-$, arylCOO$^-$, trifluoromethanesulfonate (triflate, OTf).

As defined above, the metal-organic material of the present invention is a particular type of a coordination polymer containing metal ions, preferably transition metal ions, coordinated to organic ligands each of the general formula I to form one-, two-, or three-dimensional structures. In certain embodiments, the metal-organic material of the present invention comprises at least one of said metal ions structurally coordinated between two of said at least two ligands.

In certain embodiments, the metal-organic material of the present invention comprises metal ions coordinated to organic ligands each of the general formula I to form a three-dimensional (3D) structure. In particular such embodiments, the metal-organic material of the invention has a 3D crystalline micro or sub-micro structure, more particularly wherein said crystalline micro or sub-micro structure has a geometrical shape, e.g., a brick-like microstructure. Examples of 3D crystalline geometric shape include, without being limited to, hexagonal, spherical, stella-octangula, and flower-like shape.

MOFs having 3D structures in general and such MOFs according to the present invention in particular, are porous and may thus further comprise solvent molecules, also referred to as "guest molecules", left from the preparation process and confined within the pores of the 3D structure. As the pores of the MOFs are stable during elimination of those solvent molecules, such MOFs can be used as adsorbents in processes for gas adsorption, e.g., $H_2$, CO, $CO_2$ or methane adsorption, or gas separation and/or purification, e.g., separation of $CO_2$ from methane.

In one specific embodiment, the metal-organic material of the invention comprises ligands each being ligand L1, Ni(II) ions structurally coordinated with nitrogen atoms of said ligands, and Cl$^-$ as counter anions, wherein said metal-organic material has the chemical formula $(NiCl_2N_2C_{26.5}H_{16})_n$ wherein n is an integer of at least 4, and a 3D crystalline micro or sub-micro structure optionally further comprising solvent molecules. This material is herein identified NiClL1 and may be formed, e.g., by adding a chloroform solution of L1 to a dimethylformamide (DMF) suspension of $NiCl_2$·6$H_2O$ in an oven-dried glass pressure tube, which is then sealed; heated for 5 days at 105° C. without stirring and with exclusion of light; and then gradually cooled to RT over 9-10 h. to thereby obtain NiClL1 as a light green precipitate having the geometrical shape of an elongated hexagons (brick-like). The NiClL1 crystalline structures obtained may further comprise chloroform and/or DMF molecules confined within the structural pores.

In another specific embodiment, the metal-organic material of the invention comprises ligands each being ligand L1, Ni(II) ions structurally coordinated with nitrogen atoms of said ligands, and Br$^-$ as counter anions, wherein said metal-organic material has the chemical formula $(NiBr_2N_2C_{26.5}H_{16})_n$ wherein n is an integer of at least 4, and a 3D crystalline micro or sub-micro structure optionally further comprising solvent molecules. This material is herein identified NiBrL1 and may be formed, e.g., by adding a chloroform solution of L1 to a DMF suspension of $NiBr_2$ in an oven-dried glass pressure tube, which is then sealed; heated for 5 days at 105° C. without stirring and with exclusion of light; and then gradually cooled to RT over 9-10 h. to thereby obtain NiBrL1 as a light green precipitate. The NiBrL1 crystalline structures obtained may further comprise chloroform and/or DMF molecules confined within the structural pores.

In still another specific embodiment, the metal-organic material of the invention comprises ligands each being ligand L2, Ni(II) ions structurally coordinated with nitrogen atoms of said ligands, and Cl$^-$ as counter anions, wherein said metal-organic material has the chemical formula $(NiCl_2N_2C_{26.5}H_{20})_n$ wherein n is an integer of at least 4, and a 3D crystalline micro or sub-micro structure optionally further comprising solvent molecules. This material is herein identified NiClL2 and may be formed, e.g., by carefully layering a chloroform solution of L2 below a DMF solution of $NiCl_2$·6$H_2O$ in an oven-dried glass tube, which is then sealed and kept in the dark for 5 days, to thereby obtain NiClL2 as a light green precipitate. The NiClL2 crystalline structures obtained may further comprise chloroform and/or DMF molecules confined within the structural pores.

In yet another specific embodiment, the metal-organic material of the invention comprises ligands each being ligand L2, Ni(II) ions structurally coordinated with nitrogen atoms of said ligands, and Br$^-$ as counter anions, wherein said metal-organic material has the chemical formula (NiBr$_2$N$_2$C$_{26.5}$H$_{20}$)$_n$ wherein n is an integer of at least 4, and a 3D crystalline micro or sub-micro structure optionally further comprising solvent molecules. This material is herein identified NiBrL2 and may be formed, e.g., by adding a chloroform solution of L2 to a DMF solution of NiBr$_2$ in a glass pressure tube, which is then sealed; heated for 5 days at 105° C. without stirring and with exclusion of light; and then gradually cooled to RT over 9-10 h. to thereby obtain NiBrL2 as a light green precipitate having the geometrical shape of near-regular hexagons. The NiBrL2 crystalline structures obtained may further comprise chloroform and/or DMF molecules confined within the structural pores.

In another specific embodiment, the metal-organic material of the invention comprises ligands each being ligand L2, Cu(II) ions structurally coordinated with nitrogen atoms of said ligands, and Cl$^-$ as counter anions, wherein said metal-organic material has the chemical formula (CuCl$_2$N$_2$C$_{26.5}$H$_{20}$)$_n$ wherein n is an integer of at least 4, and a 3D crystalline micro or sub-micro structure optionally further comprising solvent molecules. This material is herein identified CuClL2 and may be formed, e.g., by adding a chloroform solution of L2 to a DMF solution of CuCl$_2$ in a glass pressure tube, which is then sealed; heated for 5 days at 105° C. without stirring and with exclusion of light; and then gradually cooled to RT over 9-10 h. to thereby obtain CuClL2 as a dark green precipitate. The CuClL2 crystalline structures obtained may further comprise chloroform and/or DMF molecules confined within the structural pores.

In still another specific embodiment, the metal-organic material of the invention comprises ligands each being ligand L2, Cu(II) ions structurally coordinated with nitrogen atoms of said ligands, and Br$^-$ as counter anions, wherein said metal-organic material has the chemical formula (CuBr$_2$N$_2$C$_{26.5}$H$_{20}$)$_n$ wherein n is an integer of at least 4, and a 3D crystalline micro or sub-micro structure optionally further comprising solvent molecules. This material is herein identified CuBrL2 and may be formed, e.g., by adding a chloroform solution of L2 to a DMF solution of CuBr$_2$ in a glass pressure tube, which is then sealed; heated for 5 days at 105° C. without stirring and with exclusion of light; and then gradually cooled to RT over 9-10 h. to thereby obtain CuBrL2 as a dark green precipitate having the geometrical shape of stella-octangula. The CuBrL2 crystalline structures obtained may further comprise chloroform and/or DMF molecules confined within the structural pores.

In yet another specific embodiment, the metal-organic material of the invention comprises ligands each being ligand L2, Cu(II) ions structurally coordinated with nitrogen atoms of said ligands, and NO$_3$ as counter anions, wherein said metal-organic material has the chemical formula (Cu(NO$_3$)$_2$N$_2$C$_{26.5}$H$_{20}$)$_n$ wherein n is an integer of at least 4, and a 3D crystalline micro or sub-micro structure optionally further comprising solvent molecules. This material is herein identified Cu(NO$_3$)$_2$L2 and may be formed, e.g., by adding a chloroform solution of L2 to a DMF solution of Cu(NO$_3$)$_2$ in a glass pressure tube, which is then sealed; heated for 5 days at 105° C. without stirring and with exclusion of light; and then gradually cooled to RT over 9-10 h. to thereby obtain Cu(NO$_3$)$_2$L2 as a dark green precipitate. Alternatively, Cu(NO$_3$)$_2$L2 may be formed by adding a dry chloroform solution of L2 to a dry DMF solution of Cu(NO$_3$)$_2$.3H$_2$O under N$_2$ atmosphere in an oven-dried glass pressure tube, which is then sealed; heated for 6 days at 105° C. without stirring and with exclusion of light; and then gradually cooled to RT over 9-10 h. to thereby obtain Cu(NO$_3$)$_2$L2 as a light green precipitate having the geometrical shape of rectangular prisms. The Cu(NO$_3$)$_2$L2 crystalline structures obtained may further comprise chloroform and/or DMF molecules confined within the structural pores.

In another specific embodiment, the metal-organic material of the invention comprises ligands each being ligand L2, Cu(II) ions structurally coordinated with nitrogen atoms of said ligands, and OTf$^-$ as counter anions, wherein said metal-organic material has the chemical formula (Cu(OTf)$_2$N$_2$C$_{26.5}$H$_{20}$)$_n$ wherein n is an integer of at least 4, and a 3D crystalline micro or sub-micro structure optionally further comprising solvent molecules. This material is herein identified Cu(OTf)$_2$L2 and may be formed, e.g., by carefully layering a chloroform solution of L2 below a DMF solution of Cu(OTf)$_2$ in an oven-dried glass tube, which is then sealed and kept in the dark for 5 days, to thereby obtain Cu(OTf)$_2$L2 as a light blue precipitate. Alternatively, Cu(OTf)$_2$L2 may be formed by carefully layering a chloroform solution of L2 below a DMF solution of Cu(OTf)$_2$ in an oven-dried glass tube, which is then sealed and kept in the dark for 10 days; heated for another 2 days at 60° C. without stirring and with exclusion of light; and then gradually cooled to RT to thereby obtain Cu(OTf)$_2$L2 as a light blue precipitate. The Cu(OTf)$_2$L2 crystalline structures obtained may further comprise chloroform and/or DMF molecules confined within the structural pores.

In still another specific embodiment, the metal-organic material of the invention comprises ligands each being ligand L2, Pd(II) ions structurally coordinated with nitrogen atoms of said ligands, and Cl$^-$ as counter anions, wherein said metal-organic material has the chemical formula (PdCl$_2$N$_2$C$_{26.5}$H$_{20}$)$_n$ wherein n is an integer of at least 4, and a 3D crystalline micro or sub-micro structure optionally further comprising solvent molecules. This material is herein identified PdClL2 and may be formed, e.g., by adding a sonicated toluene solution of Pd(COD)Cl$_2$ to a toluene suspension of L2 in an oven-dried glass pressure tube, which is then sealed; heated for 3 days at 105° C. without stirring and with exclusion of light; and then gradually cooled to RT over 9-10 h. to thereby obtain PdClL2 as a yellowish precipitate. In one alternative process, PdClL2 may be formed by adding a sonicated toluene suspension of PdCl$_2$ to a toluene suspension of L2 in an oven-dried glass pressure tube, which is then sealed; heated for 3 days at 105° C. without stirring and with exclusion of light; and then gradually cooled to RT over 9-10 h. to thereby obtain PdClL2 as a yellowish precipitate. In another alternative process, PdClL2 may be formed by adding an ethylbenzene solution of Pd(PhCN)$_2$Cl$_2$ to an ethylbenzene suspension of L2 in an oven-dried glass pressure tube, which is then sealed; heated for 3 days at 105° C. without stirring and with exclusion of light; and then gradually cooled to RT over 9-10 h. to thereby obtain PdClL2 as a yellowish precipitate. In a further alternative process, PdClL2 may be formed by adding a toluene solution of Pd(PhCN)$_2$Cl$_2$ to a heptane suspension of L2 in an oven-dried glass pressure tube, which is then sealed; heated for 3 days at 105° C. without stirring and with exclusion of light; and then gradually cooled to RT over 9-10 h. to thereby obtain PdClL2 as a yellowish precipitate. The PdClL2 crystalline structures obtained may further comprise toluene, ethylbenzene and/or heptane molecules confined within the structural pores.

In yet another specific embodiment, the metal-organic material of the invention comprises ligands each being ligand L2, Zn(II) ions structurally coordinated with nitrogen atoms of said ligands, and OAc$^-$ as counter anions, wherein said metal-organic material has the chemical formula $(Zn(OAc)_2N_2C_{26.5}H_{20})_n$, wherein n is an integer of at least 4, and a 3D crystalline micro or sub-micro structure optionally further comprising solvent molecules. This material is herein identified ZnOAcL2 and may be formed, e.g., by adding a chloroform solution of L2 to a DMF solution of $Zn(OAc)_2 \cdot 2H_2O$ in an oven-dried glass pressure tube, which is then sealed; heated for 2 days at 105° C. without stirring and with exclusion of light; and then gradually cooled to RT over 9-10 h. to thereby obtain ZnOAcL2 as a light white precipitate having the geometrical shape of spheres. Alternatively, ZnOAcL2 may be formed by adding a chloroform solution of L2 to a DMF solution of $Zn(OAc)_2 \cdot 2H_2O$ in an oven-dried glass pressure tube, which is then sealed; heated for 3 days at 105° C. without stirring and with exclusion of light; and then gradually cooled to RT over 9-10 h. to thereby obtain ZnOAcL2 as a light white precipitate having the geometrical shape of spheres. The ZnOAcL2 crystalline structures obtained may further comprise chloroform and/or DMF molecules confined within the structural pores.

In another specific embodiment, the metal-organic material of the invention comprises ligands each being ligand L2, Zn(II) ions structurally coordinated with nitrogen atoms of said ligands, and Cl$^-$ as counter anions, wherein said metal-organic material has the chemical formula $(ZnCl_2N_2C_{26.5}H_{20})_n$ wherein n is an integer of at least 4, and a 3D crystalline micro or sub-micro structure optionally further comprising solvent molecules. This material is herein identified ZnClL2 and may be formed, e.g., by adding a chloroform solution of L2 to a DMF solution of $ZnCl_2 \cdot 2H_2O$ in an oven-dried glass pressure tube, which is then sealed; heated for 3 days at 105° C. without stirring and with exclusion of light; and then gradually cooled to RT over 9-10 h. to thereby obtain ZnClL2 as a light white precipitate having the geometrical shape of spheres. In one alternative process, ZnClL2 may be formed by adding a chloroform solution of L2 to a DMF solution of $ZnCl_2 \cdot 2H_2O$ in an oven-dried glass pressure tube, which is then sealed; heated for 2 days at 105° C. without stirring and with exclusion of light; and then gradually cooled to RT over 9-10 h. to thereby obtain ZnClL2 as a light white precipitate having the geometrical shape of spheres. In another alternative process, ZnClL2 may be formed by adding a chloroform solution of L2 to a DMF solution of $ZnCl_2 \cdot 2H_2O$ in an oven-dried glass pressure tube, which is then sealed; heated for 3 days at 105° C. without stirring and with exclusion of light; and then gradually cooled to RT over 9-10 h. to thereby obtain ZnClL2 as a light white precipitate having the geometrical shape of spheres. The ZnClL2 crystalline structures obtained may further comprise chloroform and/or DMF molecules confined within the structural pores.

In still another specific embodiment, the metal-organic material of the invention comprises ligands each being ligand L2, Zn(II) ions structurally coordinated with nitrogen atoms of said ligands, and Br$^-$ as counter anions, wherein said metal-organic material has the chemical formula $(ZnBr_2N_2C_{26.5}H_{20})_n$ wherein n is an integer of at least 4, and a 3D crystalline micro or sub-micro structure optionally further comprising solvent molecules. This material is herein identified ZnBrL2 and may be formed, e.g., by adding a chloroform solution of L2 to a DMF solution of $ZnBr_2$ in an oven-dried glass pressure tube, which is then sealed; heated for 2 days at 105° C. without stirring and with exclusion of light; and then gradually cooled to RT over 9-10 h. to thereby obtain ZnBrL2 as a white precipitate having the geometrical shape of spheres. The ZnBrL2 crystalline structures obtained may further comprise chloroform and/or DMF molecules confined within the structural pores.

In another aspect, the present invention relates to a method for the preparation of a metal-organic material as defined above, comprising the steps of: (i) providing (a) an organic solution or suspension of a metal salt, herein referred to as the "metal component", consisting of anions and said metal ions; and (b) an organic solution or suspension of said ligands, herein referred to as the "organic component", in a pressure vessel; (ii) sealing and keeping said pressure vessel for a period of time, e.g., for about 1, 2, 3, 4, 5, 6, 7, 8, 9 or 10 days, or more, with exclusion of light and without stirring, thereby reacting said metal ions with said ligands to obtain said metal-organic material as a precipitate; and (iii) collecting said precipitate. It should be noted that where particular values are described in the description and claims, unless otherwise stated, the term "about" means that an acceptable error range, e.g., up to 5% or 10%, for the particular value should be assumed.

The term "pressure vessel" as used herein refers to a closed container designed to hold liquids or gases at a pressure substantially different from the ambient pressure. Pressure vessels can theoretically be almost any shape, e.g., cylinders with end caps, i.e., heads, either hemispherical or dished (torispherical), and can be made of any suitable composite material. In one embodiment, the pressure vessel utilized in the method of the present invention is a glass pressure vessel, more particularly, a glass pressure tube as used in the studies described herein.

In certain embodiments, step (ii) of the method of the invention is carried out while heating the pressure vessel containing the metal salt solution/suspension and the ligand solution/suspension to a temperature ranging from 60° C. to 120° C., e.g., from 60° C. to 70° C., 70° C. to 80° C., 80° C. to 90° C., 90° C. to 100° C., 100° C. to 105° C., 105° C. to 110° C., 110° C. to 115° C., or 115° C. to 120° C., for the whole said period of time or a part thereof, and then gradually cooling said pressure vessel. As shown herein, in some cases, step (ii) comprises sealing and keeping said pressure vessel for a period of time with exclusion of light and without stirring, while heating to a temperature as defined above for the whole period of time and then gradually cooling, e.g., to room temperature, prior to step (iii). Alternatively, step (ii) may comprise sealing and keeping said pressure vessel for a period of time with exclusion of light and without stirring, while heating as defined above for a part of said period of time, i.e., at the beginning of said period of time, during said period of time, or at the end of said period of time, and then gradually cooling, e.g., to room temperature.

In certain embodiments, steps (i) and (ii) of the method of the invention are carried out under inert conditions, e.g., under argon or $N_2$.

The organic solvents in which said ligands and metal salt are dissolved may independently be either polar or non-polar, wherein the solubility of the ligands in the organic solvent in which they are dissolved determines whether the organic component would be in the form of a solution or suspension, and the solubility of the metal salt in the organic solvent in which it is dissolved determines whether the metal component would be in the form of a solution of suspension. Non-limiting examples of organic solvents include chloroform, dimethylformamide (DMF), alkanols such as methanol, ethanol, isopropanol, n-butanol, sec-butanol, isobutanol, pentanol and hexanol, DMSO, acetonitrile, ethylene glycol, toluene, benzene, ethylbenzene, ether (diethyl ether), and alkanes such as pentane, hexane, cyclohexane, heptane, cycloheptane, octane, cyclooctane, nonane, decane and decalin.

As shown herein, in cases the solubility of the metal salt in the organic solvent utilized is poor, however an organic solution rather than suspension of the metal salt is desired, a compound capable of forming a coordination complex, i.e., metal complex, with the metal atom thus increasing the solubility of said metal salt in said organic solvent may be added. In particular such cases exemplified herein, $PdCl_2$ in which the Pd atoms are coordinated with 1,5-cyclooctadiene (COD) or benzonitrile (PhCN), i.e., $Pd(COD)Cl_2$ or $Pd(PhCN)_2Cl_2$, respectively, were dissolved in toluene or ethylbenzene so as to obtain a toluene or ethylbenzene solution rather than suspension of $PdCl_2$.

According to the method of the invention, the metal-organic material is obtained as a result of a reaction taking place in the pressure vessel during step (ii). As clearly shown herein, metal-organic materials comprising the same ligands and metal ions, but having different 3D crystalline structures, thus potentially different physical and chemical properties, are obtained depending on the reaction components, e.g., anions and organic solvents in which said ligands and metal salt are dissolved, as well as the reaction conditions, e.g., the period of time during which the organic component and metal component are reacted in step (ii), the temperature in which the reaction is conducted or the thermal profile of the reaction (in cases the reaction includes heating for a part of said period of time), and cooling rate (in cases the reaction comprises heating for the whole said period of time or a part thereof).

The metal-organic material obtained by the method of the present invention comprises metal ions, preferably transition metal ions, coordinated to organic ligands each of the general formula I to form one-, two-, or three-dimensional structures, wherein the particular metal ion and organic ligand selected dictates the structure and hence physical and chemical properties of the material. In certain embodiments, the metal-organic material has a 3D crystalline micro or sub-micro structure that may have a particular geometric shape as defined above. It should be understood that while crystalline micro and sub-micro structures obtained using different reaction components and/or under different reaction conditions may have different geometrical shapes, a preparation process as defined above, utilizing particular reaction components and carried out under particular reaction conditions, results in a population of 3D crystal structures having uniform geometrical shape.

In certain embodiments, the geometrical shape of the 3D micro and sub-micro structures obtained by the method of the invention is thus affected by reaction components and/or the reaction conditions or parameters in steps (ii), wherein said reaction components are, e.g., one or more of said metal ions, anions, and organic solvents, and said reaction conditions or parameters are, e.g., one or more of said temperature, period of time, and cooling rate.

The MOFs of the present application are useful as adsorbents in processes for gas adsorption, e.g., $H_2$, CO, $CO_2$ or methane adsorption, or gas separation and/or purification, e.g., separation of $CO_2$ from methane.

In yet another aspect, the present invention thus relates to use of a metal-organic material as defined above as an adsorbent in a process for gas adsorption or gas separation.

In still another aspect, the present invention relates to a process for gas adsorption or gas separation by adsorbing said gas to an adsorbent, the improvement wherein said adsorbent is a metal-organic material as defined above.

The invention will now be illustrated by the following non-limiting Examples.

EXAMPLES

Materials and Methods

General Methods.

Glass pressure tubes were cleaned by immersion in a piranha solution (7:3 v/v, $H_2SO_4$/30% $H_2O_2$) for 10 min and deionized (DI) water and then dried for 12 h at 130° C. Caution: piranha is an extremely dangerous oxidizing agent and should be handled with care using appropriate personal protection.

Transmission Electron Microscopy (TEM).

TEM imaging was performed with a Philips CM-120 instrument operating at 120 kV, equipped with a charge-coupled device camera (2k×2k Gatan Ultrascan 1000). TEM samples were prepared by placing a 5 µl drop of the reaction mixture on a formvar/carbon, 400 mesh Cu grid and blotting after 10 s. Due to beam sensitivity of the specimens, TEM imaging and SAED measurements were performed under low-dose conditions. An EDAX EDS system was used to perform the elemental analysis.

Scanning Electron Microscopy (SEM).

SEM measurements were performed using HRSEM ULTRA-55 ZEISS and HRSEM SUPRA-55 VP ZEISS instruments at an EHT voltage of 3 kV. SEM samples were prepared by placing a drop of the reaction mixture or a DMF suspension of isolated MOFs on a silicon substrate which was dried under air.

FTIR and NMR Spectroscopy.

The infra-red spectra were obtained using a Nicolet 460 single beam FT-IR. $^1H$ and $^{13}C\{^1H\}$NMR measurements were run on a 300 MHz Bruker NMR spectrometer.

Atomic Force Microscope (AFM).

AFM topographical imaging was performed on a P47 Solver AFM (NT-MDT, Zelenograd, Russia) using AC240 probes (Olympus) in intermittent contact mode, as well as with Multimode 8 AFM (Bruker, Santa Barbara, Calif.). The latter system was operated with the "Peak force Quantitative Mechanical Mapping (PF-QNM)" mode which enables acquisition of elastic modulus simultaneously with the topographic image. For this measurement, Bruker RTESPA probes were used. The spring constant, determined by the Sader method (Sader et al., 1999) was 80 N/m. The elastic modulus is derived from force curves acquired at each pixel, and rely on several calibrations (cantilever deflection sensitivity, spring constant, tip radius) which are input into the DMT analysis (Tabor, 1977). The deformation was on the order of 5-10 nm, thus very sensitive to the tip and sample surface condition, which can change the effective tip radius during course of scan. Estimated uncertainty in modulus measurement is 30%. Samples were prepared on silicon substrates as in the case of SEM.

Rapid Thermal Processing (RTP) and Thermogravimetric Analysis (TGA).

RTP was carried out on a Rapid Thermal Annealer for 5 min. under a stream of 10% $H_2/N_2$ or under vacuum at different temperatures (200-600° C.). The samples were prepared as in the case of SEM. TGA was performed on a SDT Q600 V8.3 Build 101 instrument using alumina sample pans under a stream of $N_2$.

Magnetic Measurements.

Figure 20A:
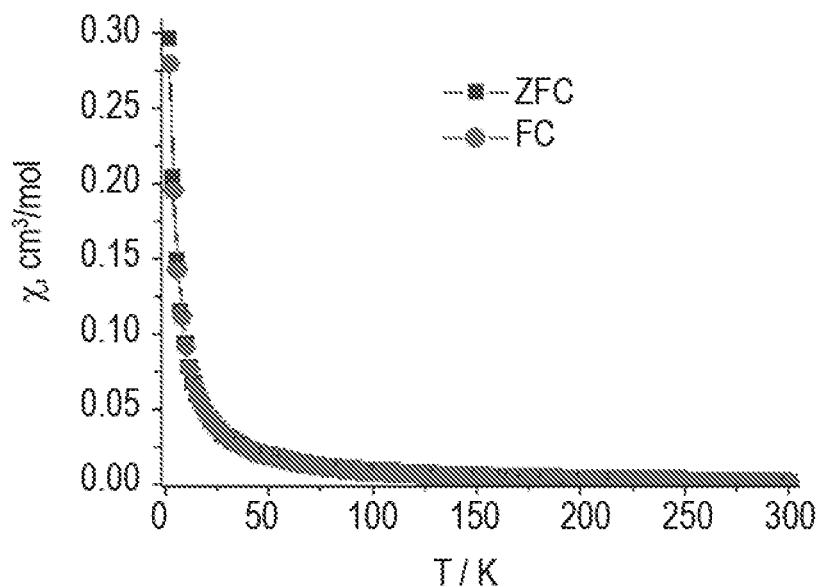
FIGS. 20A-20C show ZFC and FC temperature dependence of molar magnetic susceptibility of NiClL1 (20A); magnetic field dependencies of magnetic moment at T=6K (20B); and calculated effective magnetic moment of $Ni^{2+}$ vs. temperature (20C).
Figure 20B:
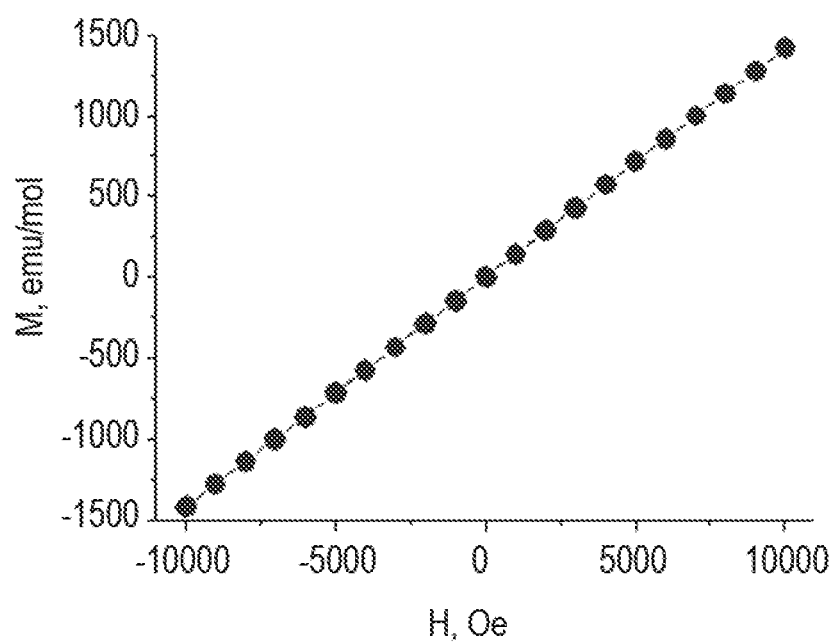
Figure 20C:
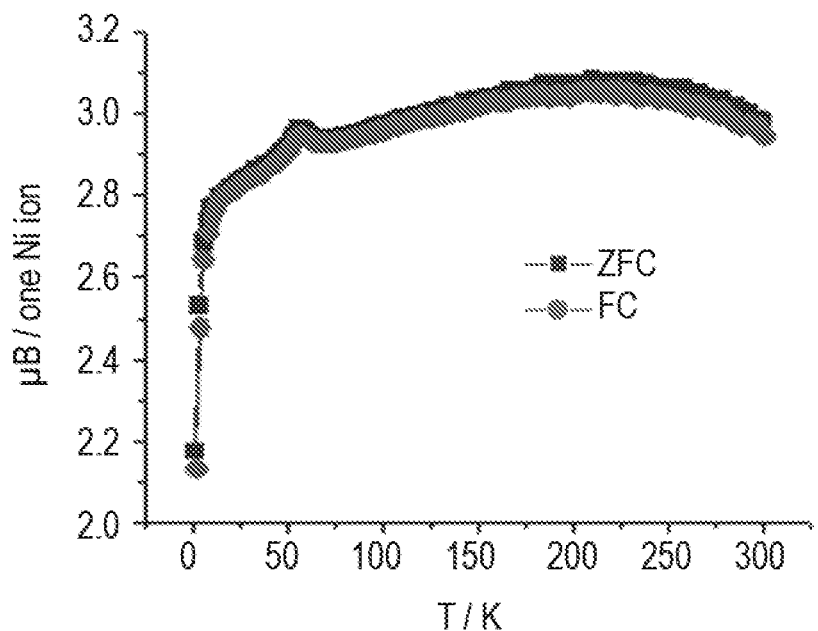
Figure 21:
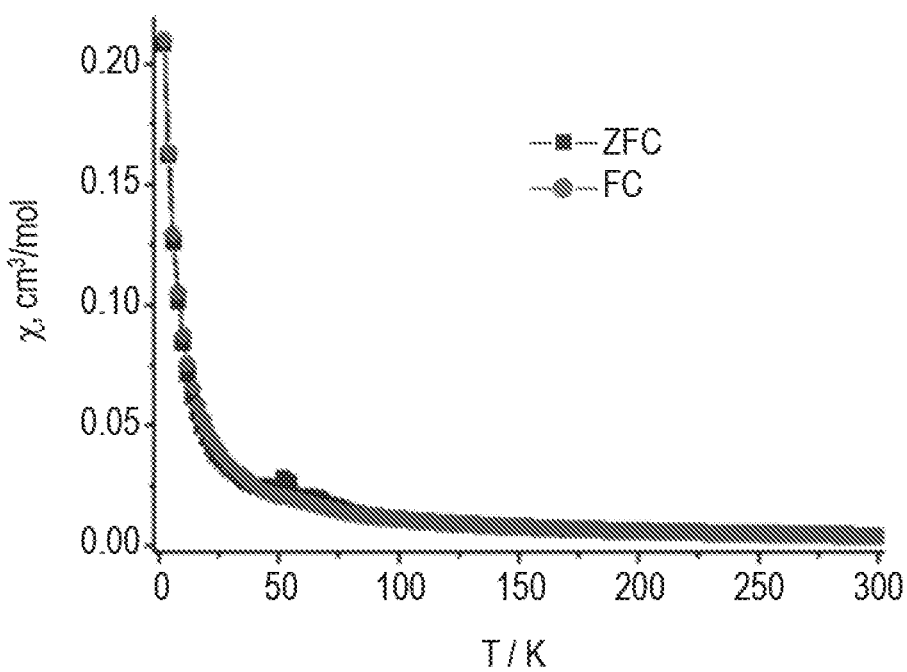
FIG. 21 shows magnetic profiles (ZFC and FC measurement) of NiBrL2.

The magnetic properties of isolated samples were measured using a SQUID magnetometer MPMS XL. The samples were weighed and placed in gelatine capsules and cooled from RT down to 2K without applying any external magnetic field (ZFC) and an internal magnetic field of strength 1000 Oe (FC). Temperature dependences of the magnetic moment were measured during heating from 2K to 300K under an applied external magnetic field (H=1000 Oe). The dependence of magnetic susceptibility on the temperature was normalized using the estimated chemical formula of NiClL1 $(NiCl_2N_2C_{26.5}H_{16})_n$ and NiBrL2 $(NiBr_2N_2C_{26.5}H_{20})_n$. This dependence is similar for the inclusion of DMF (0.5-4 molecules/Ni). The ZFC and FC dependences were found to be superimposed (FIGS. 20A, 21). The Weiss equation defines the temperature dependency of magnetic susceptibility and can be expressed as $\chi=\chi_0 + C/(T-\theta)$, where C is Curie constant, $\chi_0$ is the temperature independent parameter and $\theta$ corresponds to the Weiss parameter.

Gas Uptake Studies.

The gas adsorption studies were carried out on a Pressure Composition Isotherm (PCI) instrument (Advanced Materials Corporation, USA). About 50 mg of the compound, e.g., NiClL1, was loaded into a sample chamber inside a glove box under argon. The sample chamber was then connected to a vacuum line. The sample was activated by heating slowly to 120° C. (for $CH_4$ adsorption) and to 70° C., 100° C. and 120° C. (for $H_2$ adsorption) and held for 4 hours at these temperatures followed by cooling to RT. The temperature of the sample chamber was held constant during the measurements. The gas uptake was determined using Sieverts principle. The density of the sample was measured by gas pycnometry using helium (10 bar).

General Procedure for the Synthesis of the MOFs.

A $CHCl_3$ solution (1.0 ml) of the polypyridyl ligand L1 (Schilling et al., 2011) or L2 (Thompson et al., 1997) (6.8 μmol) was added to a DMF solution (3.0 ml) of the corresponding metal salt: $NiCl_2$, $NiBr_2$, $CuCl_2$, $CuBr_2$ and $Cu(NO_3)_2$ (6.8 μmol for 1 eq. and 13.6 μmol for 2 eq.), in a glass pressure tube. Then, the tube was sealed and heated for 5 days at 105° C. without stirring and with exclusion of light, followed by controlled cooling to RT over 9-10 h in steps of 10° C./h. This resulted in a precipitate (light green for the Ni-based MOFs and dark green for the Cu-based MOFs). The MOFs were collected in near quantitative yield (>95%) by centrifugation of the reaction mixture for ~10 min. at 5000 rpm and decanting the mother liquor.

Study 1. Homogeneously Microstructured Srystalline Nickel-Organic Coordination Polymers Micro-sized brick-like structures of the coordination polymer were obtained by differential solvothermal synthesis as described. A DMF solution of 1 equivalent of $NiCl_2.6H_2O$ was heated with a chloroform solution of 0.5 equivalents of the ligand L1 in a sealed pressure tube at 105° C. for 5 days in the dark, and then subjected to slow cooling over 9-10 hours. A white precipitate was formed immediately on mixing the two solutions and was allowed to stand and sediment without disturbance under the mentioned conditions. After cooling to RT, the light green precipitate was collected by centrifugation.

SEM image of NiClL1 revealed the brick-like structures and a statistical analysis on three hundred randomly chosen brick-like structures from a representative sample of NiClL1 established a reasonable uniformity in size distribution (FIG. 1) with most of the structures fitting in lengths of 2.5-2.7 μm, breadths of 1.2-1.4 μm and thickness of 200-300 nm. TEM images showed the crystalline nature of the material; the existence of lattice planes could be recognized via TEM imaging and SAED (FIG. 2); and the longest axis of symmetry was found to be along the length of the crystal.

AFM studies revealed the same shapes as seen in electron micrographs as well as the apparent surface roughness of the material. The debris observed also in the TEM micrographs appears to be disordered material, ranging from tens to over one hundred nm height. The upper surface of the crystallites was generally flat, although scattered depressions could be observed, as well as new layers appearing over parts of the surface (FIG. 3).

Measurements of elastic modulus on these nanostructures gave values between 2-12 gigapascals (GPa). These values are within the range of those observed for organic crystals (Roberts et al., 1991). The elastic modulus was measured simultaneously with the topographic image, so values are correlated at the pixel level with topographic features. FIG. 2 shows images of modulus and corresponding topography. The modulus signal over the Si substrate saturates at high values for this probe. For these stepped features, the modulus of the higher regions was about half that of the lower regions. This observation is consistent with the premise that crystallites undergo a polishing process during the growth, with the higher, less ordered regions being removed with time. Such less ordered regions are expected to be more deformable and hence show lower modulus values (FIG. 4).

Figure 5:
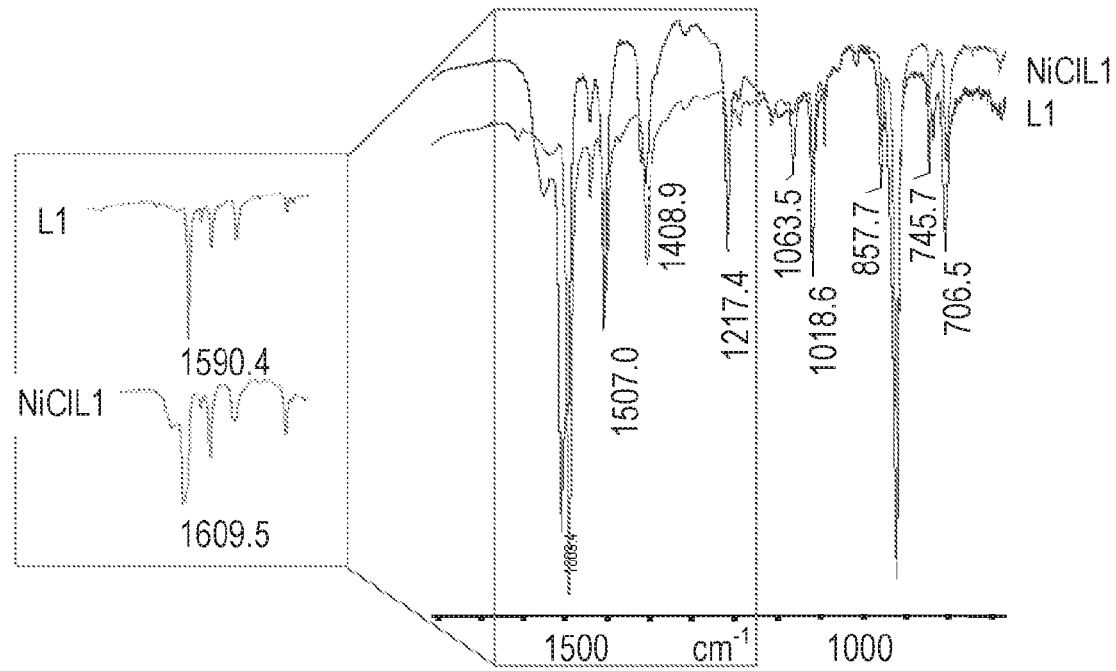
FIG. 5 shows FT-IR spectra (KBR pellet) of L1 and NiClL1.
Figure 6:
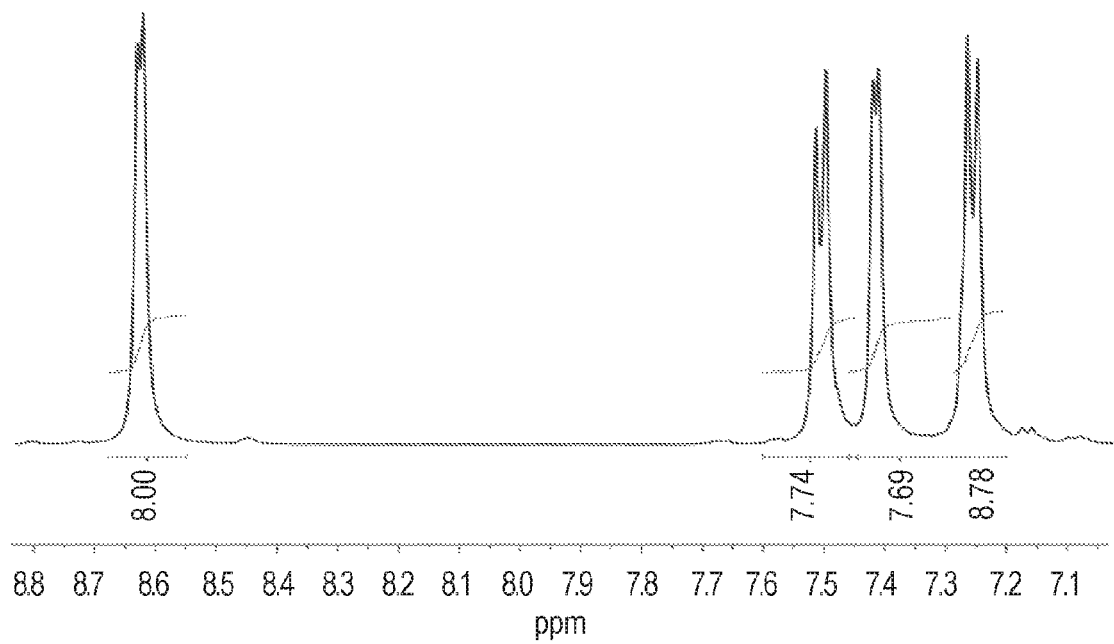
FIG. 6 shows representative $^1$H NMR spectrum ($CDCl_3$) of the $CHCl_3$ extract after reacting NiClL1 with conc. HCl and neutralizing with $Et_3$N. The spectrum corresponds to pure ligand L1.

FT-IR spectrum (KBr pellets) of NiClL1 showed a shift of 20 $cm^{-1}$ compared to free ligand L1 (FIG. 5). Unsurprisingly, concentrated acid digested the whole system and $^1H$ NMR of resulting mixture extracted with chloroform after neutralizing with $Et_3N$, matched exactly the ligand L1 (FIG. 6) and the mass spectrometric analysis of the crude mixture revealed the presence of the ligand L1 and $NiCl_2$. MALDI-TOF analysis also confirmed that the ligand was intact in the complex NiClL1. The elemental composition of the micro bricks were confirmed by nanoprobe X-ray EDS, revealing the presence of Ni, Cl and N atoms and the Ni/N ratio was found to be 0.44 (FIG. 7) and the value is in close agreement with the formation of a completely formed coordination saturated network comprising of two pyridines per Ni centre (Kaminker et al., 2010; Choudhury et al., 2010), but other modes of coordination may not be completely excluded.

Figure 8:
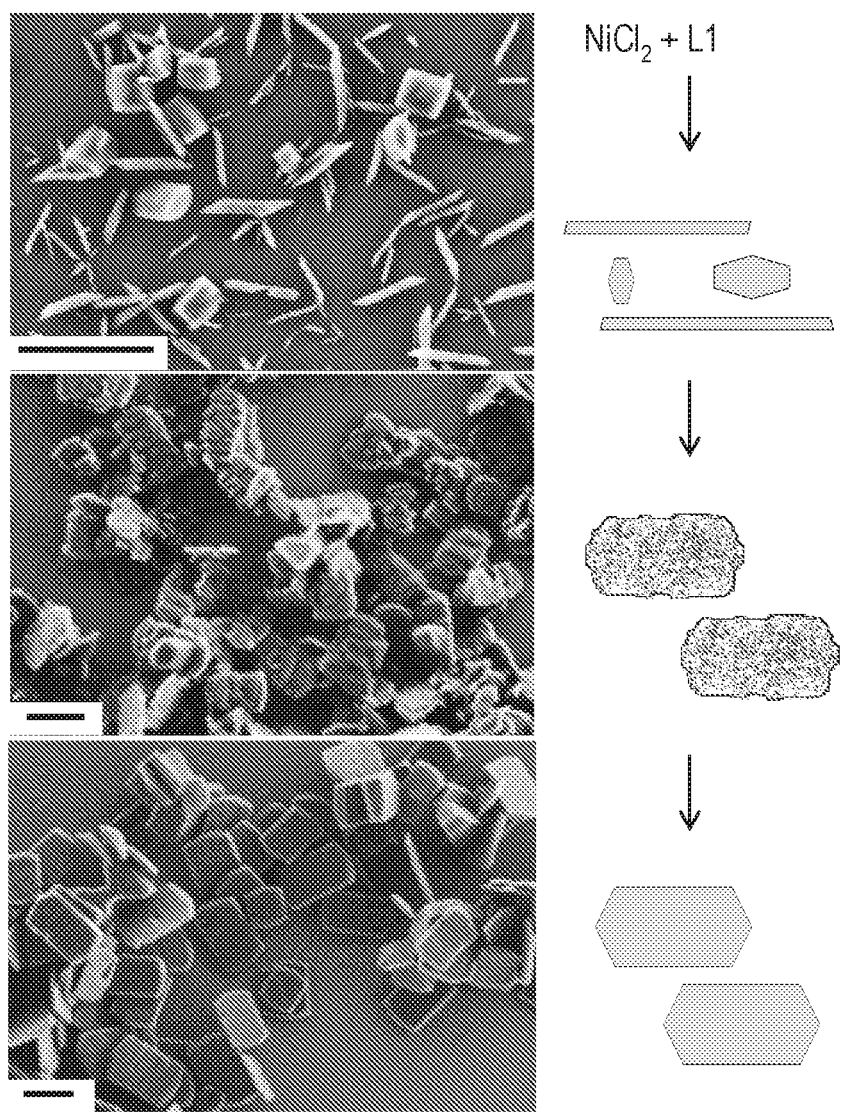
FIG. 8 shows time-dependent SEM analysis on the formation of brick-like structures NiClL1 (left panels) and a cartoon depicting the NiClL1 formation (right panels) immediately on mixing the $CHCl_3$/DMF solutions of $NiCl_2.6H_2O$ and L1 (upper panels); after heating the reaction mixture at 105° C. for 48 h in a sealed pressure tube (middle panels); and after heating the reaction mixture for 5 days and controlled cooling down to RT (scale bar=2 µm) (lower panels).

The formation of these well-defined rectangular structures may be viewed as an impact of face or axial confined growth mechanism, but the mechanistic understanding behind the formation of such uniform structures is still preliminary and can be expected to follow a regular coordination process followed by a thermally initiated close packing by the fusion of individual building blocks. Time dependent SEM analysis alongside the course of reaction revealed a speculative but justifiable mechanism for the formation of the finally observed structures. As expected, the ligand L1 on mixing with the Ni salt solution immediately formed the corresponding coordination polymer with non-uniform rod- and very small block-like structures (FIG. 8, upper panels), which in turn on heating under pressure fused to form the brick-like micro structures (FIG. 8, middle panels). The effect of the solvent mixture at any point time may not be completely excluded as the coordination polymer precipitates instantaneously and hence may account for the reduction in surface tension through agglomeration. Over time and under the influence of high temperature, the surface of these structures got smoothened to a large extent giving rise to flat faces with some apparent degree of surface roughness (FIG. 8, lower panels). Thus, the proposed working mechanism involves coordination/nucleation followed by aggregation/oligomerisation, fusion/growth and annealing. Mirkin and co-workers have proposed a similar mechanism for the formation of perfect micro spheres during the polymerization of Troger's base precursors and Zn(II) (Spokoyny et al., 2009; Oh and Mirkin, 2005; Jeon et al., 2009).

Figure 11:
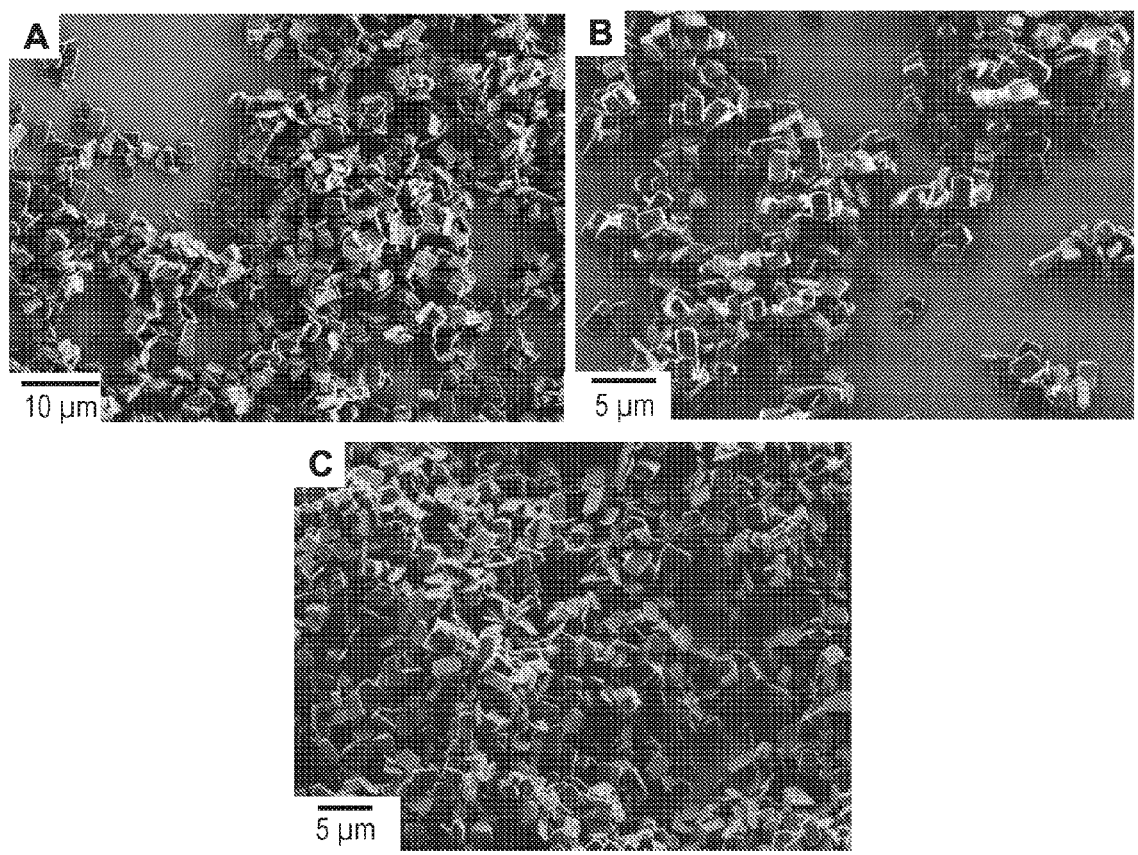
FIG. 11 shows SEM images showing the brick-like microstructures of NiClL1 suspended for 2 months in DMF (panel A); water (panel B); or a 1:1 v/v mixture of DMF/water (panel C) at RT in air with exclusion of light.

The micro moieties thus obtained was found to be insoluble in all common solvents including water and was found to be stable in most of the commonly used solvents in air at RT. This stability of the structure may be established by the SEM images of the solid material suspended in water, DMF and a mixture of both in dark, taken after 2 months (FIG. 11).

The final structure of the coordination polymer was found to depend on several parameters including the technique employed, molar ratios of the reagents, solvent system, time of the reaction and temperature. It has already been mentioned that mixing a $CHCl_3$ solution of the ligand L1 with a DMF solution of $NiCl_2.6H_2O$ at RT gave non-uniform rod- and very small block-like structures. Layering carefully a $CHCl_3$ solution of the ligand L1 under a DMF solution of the Ni salt in a molar ratio of 1:1 or 1:2 afforded a light green precipitate when allowed to stand overnight in the dark, and SEM images of a representative sample showed a mixture of rods—longer and more uniform and some amounts of junk material with no well-defined structure. Heating this mixture (after complete diffusion in about 4 days) in a pressure tube to 80-105° C. for 3-5 days brought about drastic changes in the structures observed under SEM suggesting that the longer rods thus obtained were unstable and underwent random melting and fusion under thermal treatment as the junk material along with the rods seemed to have aggregated to form some sort of lumps.

Figure 12:
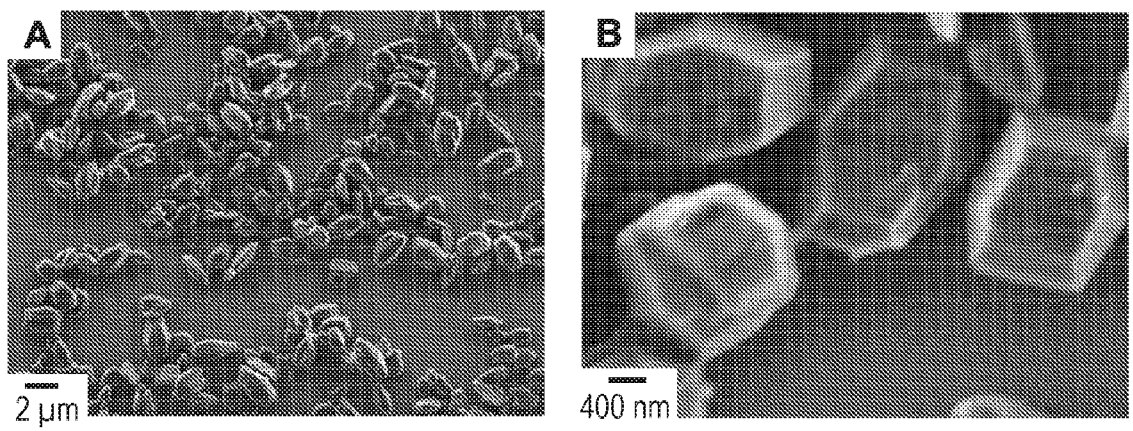
FIG. 12 shows SEM image of the microstructures obtained by heating in a sealed pressure tube at 105° C. for 5 days a DMF solution (3.0 ml) of $NiCl_2.6H_2O$ (1.6 mg, 6.9 µmol) and a $CHCl_3$ solution (1.0 ml) of L1 (5.0 mg, 6.9 µmol) without stirring and with exclusion of light (panel A); and a magnified image (panel B).

Although changing the molar ratio of the ligand and the metal did not affect much the outcome of the layering technique, it was found to have substantial effect on the structural features under thermal protocol. Heating the ligand and the metal in the same solvent system under the same conditions, but in a ratio of 1:1, resulted in smaller and different brick-like structures with a wider size distribution (FIG. 12).

Figure 13:
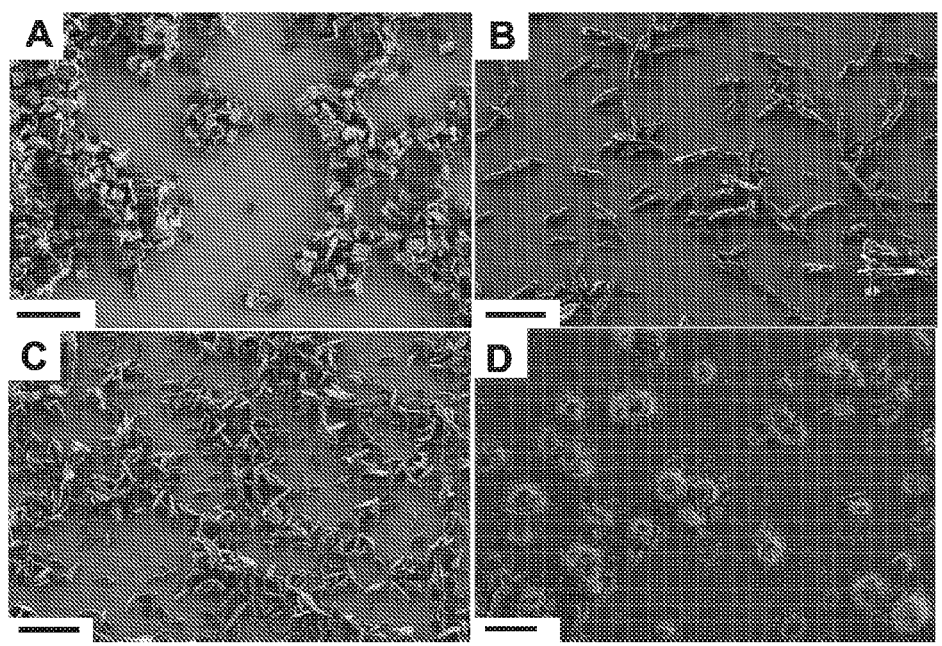
FIG. 13 shows solvent effect on the microstructure of NiClL1. SEM images: DMF:$CHCl_3$ 3:1 (v/v) (panel A); DMF (panel B); DMF:$CHCl_3$ 2:1 (v/v) (panel C); and DMF:$CHCl_3$ 3:1 (v/v)+0.5 ml $H_2O$ (panel D), (scale bar=10 µm). Each experiment was performed under solvothermal conditions at 105° C. for 5 days using a $CHCl_3$ solution of L1 (5.0 mg, 6.9 µmol) and a DMF solution (total volume 4 ml) of $NiCl_2.6H_2O$ (3.2 mg, 13.8 µmol).

The solvents used for the reaction were also found to have pronounced effect on the final structures observed under the electron microscopes. Using DMF alone as the solvent even though the ligand L1 was insoluble (FIG. 13, panel B) resulted in complete loss of the brick-like structure, where as a 1:2 mixture of $DMF/CHCl_3$ in place of a 1:3 mixture led to the formation of a comparatively more defined structures but no real brick-like moieties were observed (FIG. 13, panel C). This may be explained by the acidic nature of the proton in $CHCl_3$ that is capable of exerting H-bonded interactions with pyridines, thereby interfering with the coordination power of the lone pair. Addition of 0.25-0.5 ml of water to the 1:3 $DMF/CHCl_3$ mixture completely ruined the system (FIG. 13, panel D) and these results may also underline the effect of solvent polarity on the formation of these well-defined rectangular structures. It may be noted that in all cases except where a small amount of water was added, the precipitation of the coordination polymer was instantaneous and had the physical appearance of white insoluble material obtained under standard conditions.

Figure 14:
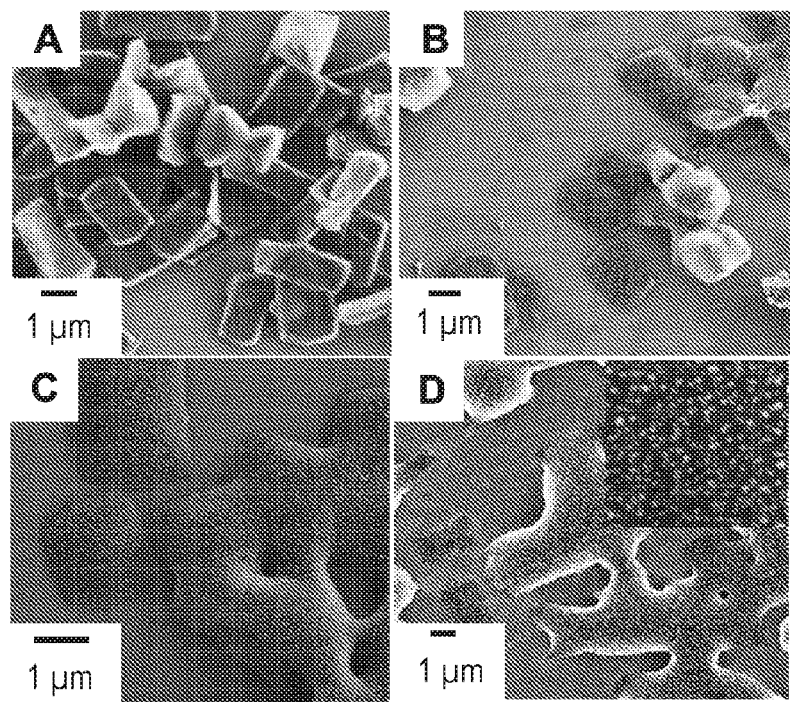
FIG. 14 shows SEM images after RTP at 300° C. (panel A); 400° C. (panel B); 500° C. (panel C); and 600° C. (panel D) of NiClL1 for 5 min. under a stream of 10% $H_2/N_2$. Inset: magnified image of the Ni nanoparticles, scale bar=100 nm.
Figure 15:
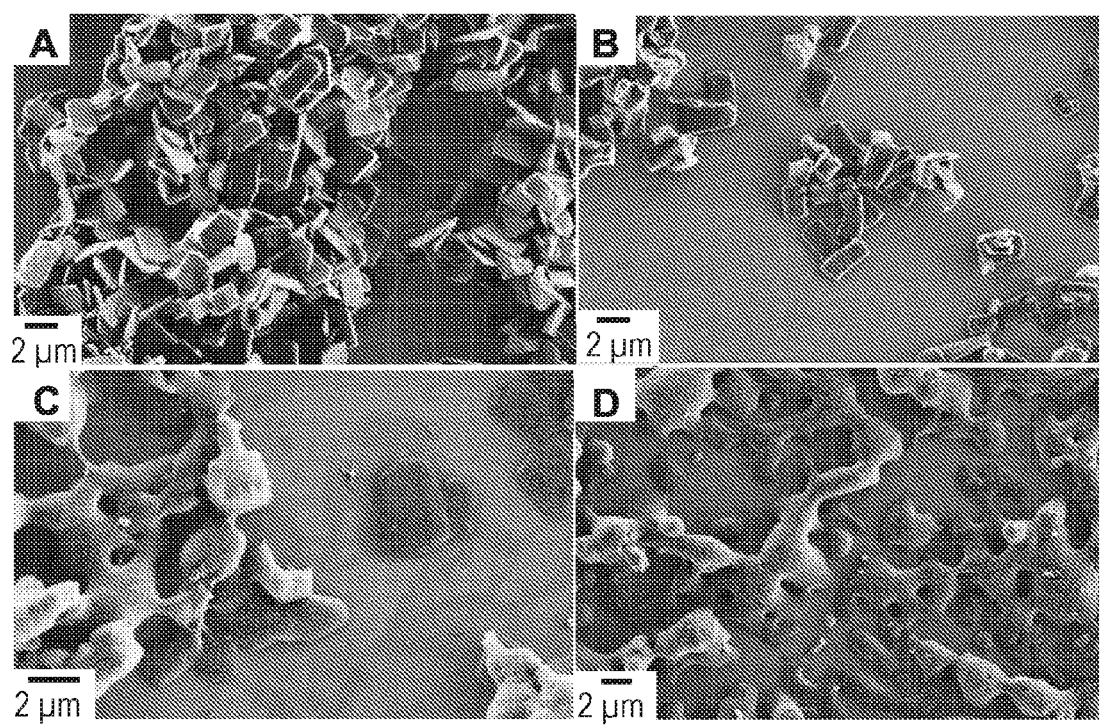
FIG. 15 shows SEM images after RTP at 200° C. (panel A); 300° C. (panel B); 400° C. (panel C); and 500° C. (panel D) of NiClL1 on a silicon substrate for 5 min. under a stream of 10% $H_2/N_2$.

The thermal behavior of materials is yet another interesting aspect of coordination polymers. RTP under a stream of 10% $H_2/N_2$ of the brick-like Ni(II) coordination polymer established that the structure are stable upto a temperature around 300° C. (FIGS. 14, 15). Moreover, the boron doped silicon surface is found to induce better stability to these structures and it may be noted that the micro-bricks lying flat on the surface retained their shape at even higher temperatures. When subjected to processing above 400° C., the melted structures were found to be adorned with nanoparticles of metallic nickel (approx. 20-25 nm).

Figure 16:
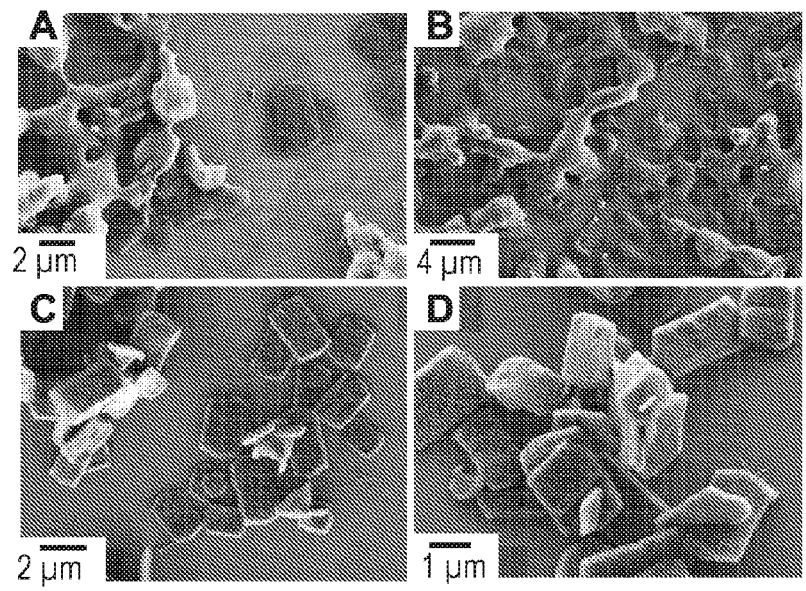
FIG. 16 shows RTP of NiClL1 for 5 min.—comparison of stability under a stream of 10% $H_2/N_2$ and in vacuum. SEM Images: (panel A) 400° C., 10% $H_2/N_2$; (panel B) 500° C., 10% $H_2/N_2$; (panel C) 400° C., vacuum; (panel D) 500° C., vacuum.

Another significant observation was that the structures appear to be much more stable if thermally treated under vacuum (FIG. 16), even though metallic nanoparticle adornment was still found to occur during the event.

Figure 17:
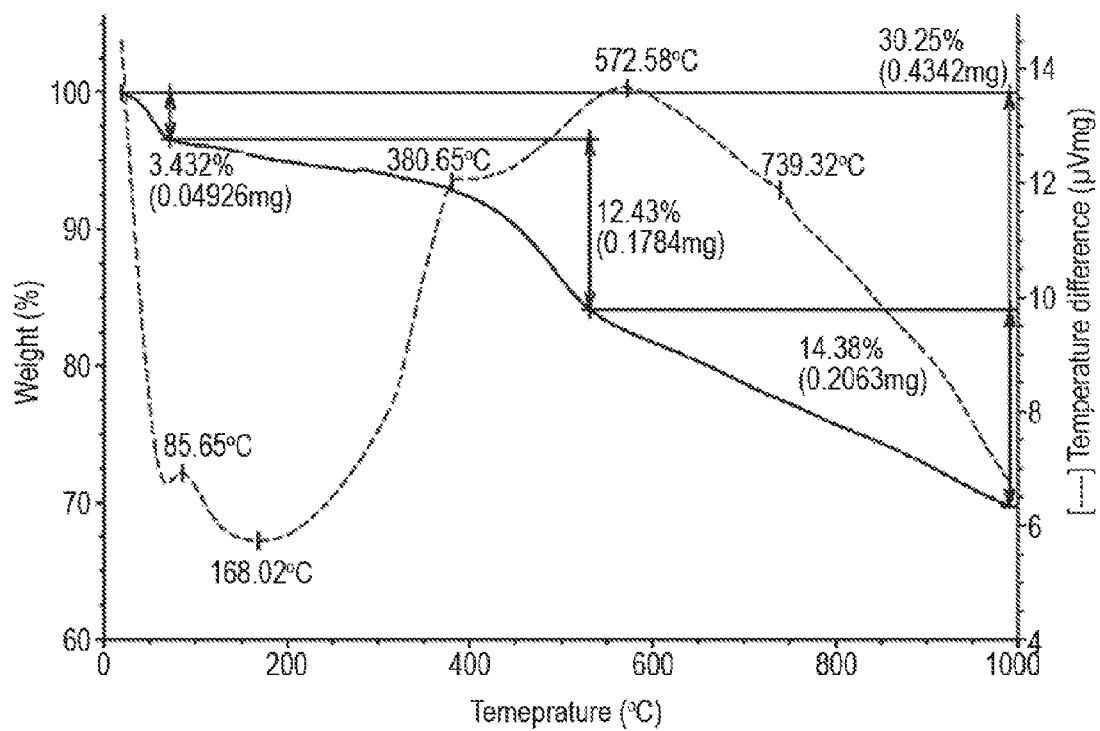
FIG. 17 shows TGA curve (continuous line) and temperature profile (dashed line) of NiClL1 from 30° C. to 1000° C.

The TGA on the brick-like structures allowed us to confirm the presence of DMF as a coordinating solvent inside the crystal lattice, since a weight loss was observed around 150° C. (FIG. 17). As found after Rapid Thermal Annealing, the structures were quite stable at this temperature and it could only be the solvent that vaporizes at this characteristic boiling point of DMF and hence justifies the observed weight loss.

Metal organic frameworks and coordination polymers find interesting application as gas storage materials (Manson et al., 2014; Adisa et al., 2012). The gas adsorption properties NiClL1 was studied as a function of pressure and the experiments done on pre-activated samples showed reasonable amount of methane (about 7.5 wt % at ambient temperature or 0° C. and 11.7 wt % at ~78.5° C. and ~35 atm pressure) and hydrogen (about 1.75 wt % at ~35 atm pressure) adsorption (FIGS. 18, 19 for $H_2$ adsorption-desorption isotherms). Moreover, the samples, during measurements, exhibited very little hysteresis between adsorption and desorption runs. The same technique was also used to determine the density of the substance and was found to be ~0.687 g/cc.

SQUID measurements revealed paramagnetic behavior for both NiClL1 and NiBrL2. The ZFC and FC dependences were found to be superimposed (FIG. 20A, 21). These magnetic properties are in agreement with a near tetrahedral or an octahedral coordination geometry of the metal center (Bridgeman, 2008).

It has been tried via various techniques including electron diffraction, powder XRD and synchrotron diffraction, to solve the crystal structure of NiClL1, but has remained unsuccessful till date, partially due to the size of the crystallite (that made it difficult to isolate a single crystal and to have a compatible beam line in the range of the size of the crysallite) and partially due to the low intensity of diffraction patterns observed (especially in electron diffraction). Nevertheless, the magnetic properties throw some light into the possible geometry—the paramagnetic behavior neglects to a large extent the possibility of a square planar Ni(II) complex, thereby leaving the options for a tetrahedral or an octahedral one. It has already been known that in a square planar complex, the ligand exerts a very strong σ interaction with the metal at the expense of complete electron pairing, leaving the σ* orbitals unoccupied, resulting in a diamagnetic behavior (Bridgeman, 2008).

Study 2. Topological Control in Metal Organic Frameworks—from Rectangular Bricks to Stellated and Interpenetrating Polyhedra In this study, we demonstrate the control of structural uniformity and diversity for MOFs. More particularly, we introduce the assembly of a series of 3-dimensional (sub)-microstructured MOFs with a narrow size distribution as well as excellent control over their topologies. Diverse structures are demonstrated, ranging from elongated hexagons and rectangular prisms to stellated and interpenetrating polyhedral, by systematically varying the (i) metal center;

(ii) anion; (iii) organic ligand; and (iv) reaction conditions, i.e., solvent, temperature, and aerobic vs. anaerobic. For instance, the use of Ni(II) salts result in distinct polyhedral topologies as opposed to Cu(II) precursors that form interpenetrating and/or stellated polyhedra. Such metal-organic structures are highly uncommon (Masoomi and Morsali, 2013). The uniformity in shape and size of our materials is attained via solvothermal synthesis without the use of surfactants or external modulators (e.g., pyridine, cetyl trimethyl ammonium bromide) (Sindoro et al., 2014; Gao et al., 2014; Ranft et al., 2013; Guo et al., 2012; Cho et al., 2008). Follow-up electron microscopy studies of the formation of the MOFs revealed a complex sequence of reactions. For the Ni-based MOFs, two types of growth process were observed involving nucleation and polishing, whereas fusion processes play a dominant role in the formation of the Cu-based MOFs.

To achieve and rationalize the topological control over metal-organic microstructures, ligand-metal-anion combinations are needed that: (i) form robust and extended 3D networks by interconnected tetrahedral nodes allowing the generation of diamondoid networks (Batten, 2001); and (ii) give rise to exceptionally high permanent microporosities and/or channels with incorporation of solvent molecules to stabilize the microstructures. Therefore, we used the two organic ligands L1 and L2 and commercially available salts of Ni(II) and Cu(II). These tetrahedral ligands are rigid, possess a full $T_d$ symmetry, and four metal ion binding sites. This combination ensures the formation of robust, porous and extended 3D networks (Lu et al., *Chem. Soc. Rev.*, DOI: 10.1039/C4CS00003J). Ni(II) and Cu(II) salts have a high affinity for pyridyl ligands (Tomasik et al., 2008; Hasenknopf et al., 1996), nevertheless the metal-N bond strength allows for the rearrangement of kinetic structures into thermodynamic products to occur at elevated temperatures (Kaminker et al., 2011). The scope of this study is demonstrated by the use of metals that have different coordination requirements. In addition, the dominant role of the anions in the formation of our microstructures has been demonstrated.

In a typical experiment, a DMF solution of the metal salt was mixed with a chloroform solution of 0.5 or 1 equivalent of L1 or L2 and heated in a glass pressure tube at 105° C. with the exclusion of light. After 4-5 days, the reaction mixture was gradually cooled over 9-10 hours and the microstructures were collected quantitatively by centrifugation. The crystalline microstructures have been characterized by electron microscope analysis, XRD and AFM. Information at the molecular level has been obtained by infra-red (IR) spectroscopy, magnetic measurements, and gas adsorption. The nickel structures have also been tested for their thermal stability.

Figure 10:
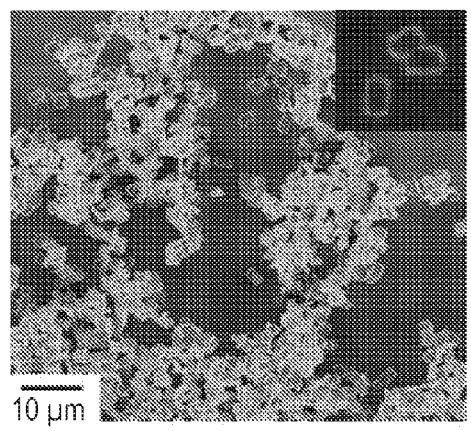
FIG. 10 shows SEM image of NiClL1 taken using an In Lens Detector. Inset—optical microscope image of NiClL1 confirming the microstructure.
Figure 22A:
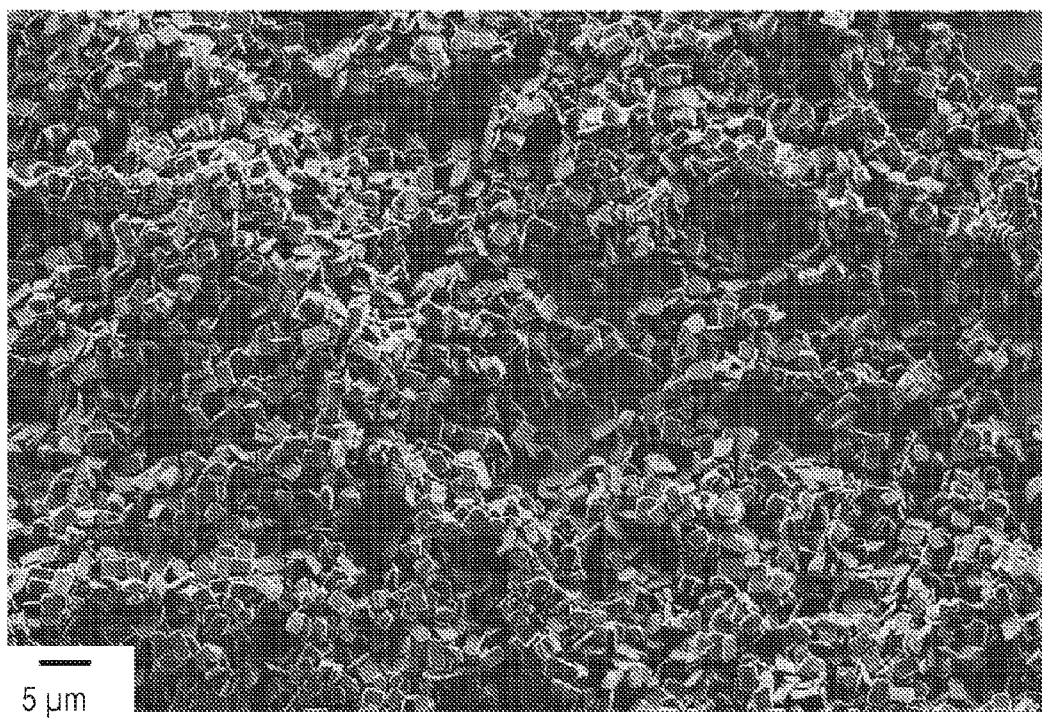
FIGS. 22A-22C show topologies of nickel chloride containing microstructures obtained by solvothermal synthesis. 22A-22B show SEM images of NiClL1 (dimensions: length: 2.6±0.9 µm, width: 1.4±0.5 µm, thickness: 250±50 nm); and 22C demonstrates histograms showing the size distribution of NiClL1. Reaction conditions: $NiCl_2$:L1=2:1, $DMF/CHCl_3$=3:1 v/v, 105° C., 5 days.
Figure 22B:
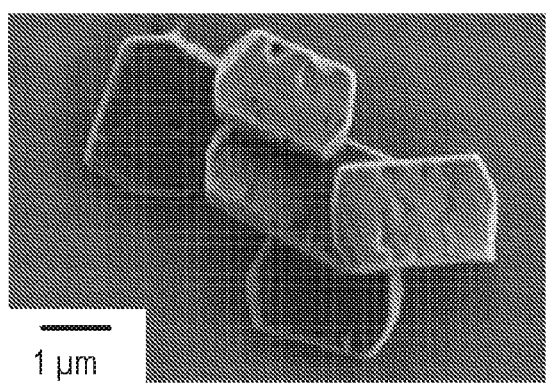
Figure 22C:
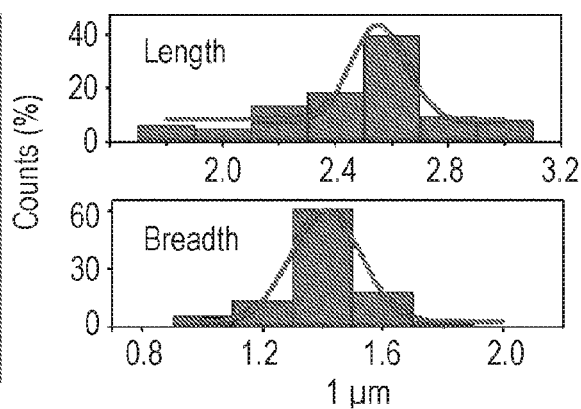
Figure 23:
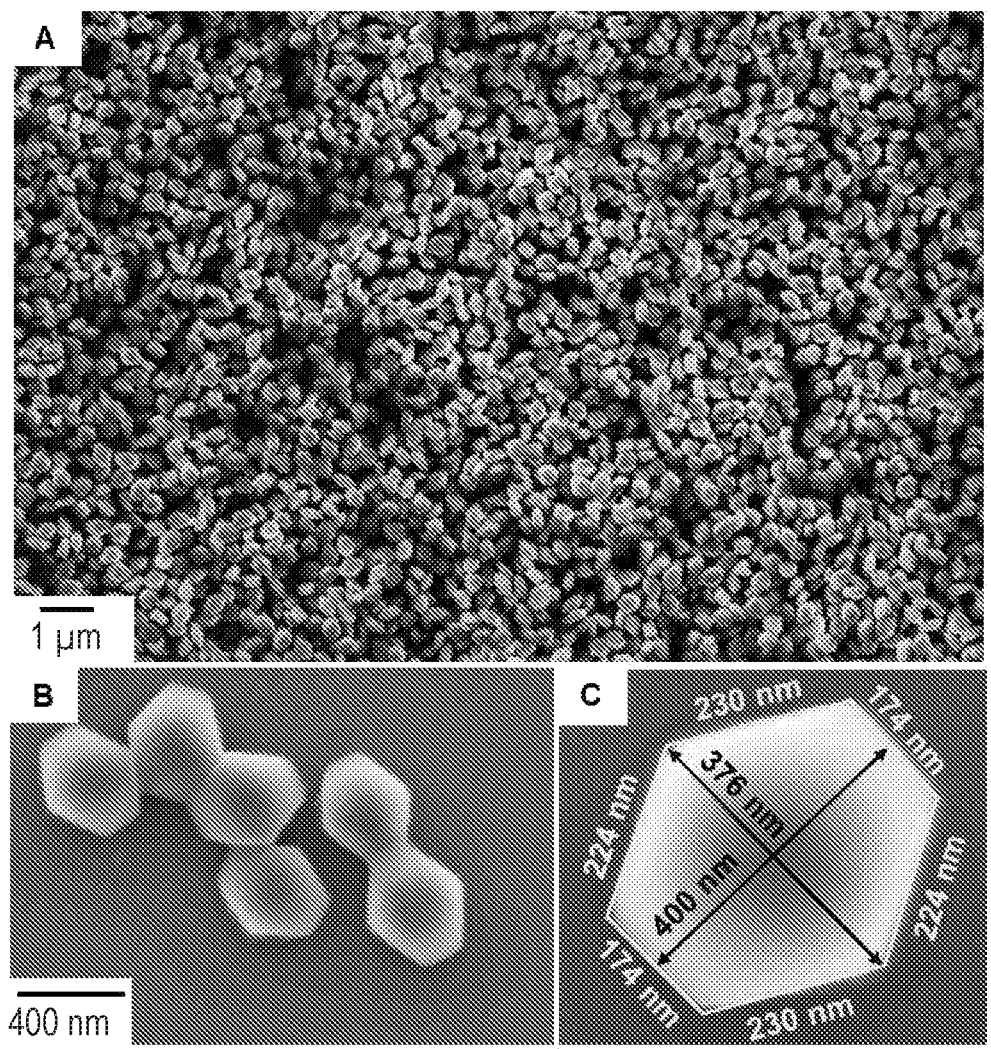
FIG. 23 shows topologies of nickel bromide containing microstructures obtained by solvothermal synthesis. Panels A and B show SEM images of NiBrL2. Dimensions: diagonal: 370±10 nm, side-to-side: 405±10 nm, thickness: 220±20 nm (panel C). Reaction conditions: $NiBr_2$:L2=2:1, $DMF/CHCl_3$=3:1 v/v, 105° C., 5 days.
Figure 24:
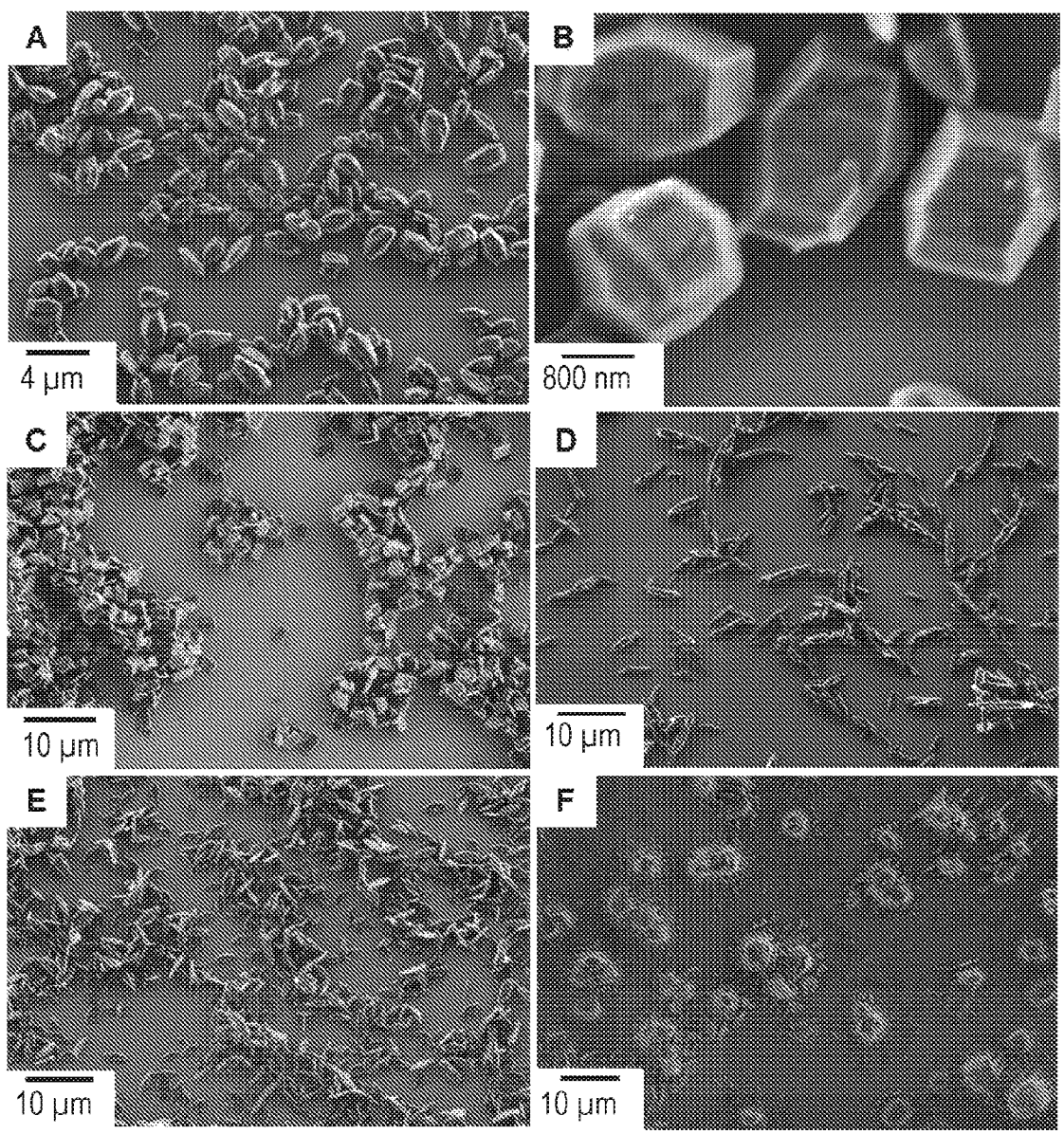
FIG. 24 shows the effect of variation in molar ratios of precursors (panels A-B) and solvent (panels C-F) on the structure of NiClL1. Panels A and B show SEM image of the microstructures obtained using 1:1 ratio of $NiCl_2$ to L1 and a magnified image thereof, respectively; reaction conditions: DMF solution (3.0 ml) of $NiCl_2.6H_2O$ (6.9 µmol), $CHCl_3$ solution (1.0 ml) of L1 (6.9 µmol), 105° C., 5 days, without stirring and with exclusion of light. Panels C, D, E and F show SEM images of NiClL1 obtained using $DMF:CHCl_3$ 3:1 (v/v); DMF; $DMF:CHCl_3$ 2:1 (v/v); and $DMF:CHCl_3$ 3:1 (v/v)+0.5 ml $H_2O$, respectively; reaction conditions: DMF solution of $NiCl_2.6H_2O$ (13.8 µmol), $CHCl_3$ solution of L1 (6.9 µmol), 105° C., 5 days, without stirring and with exclusion of light.

SEM and TEM imaging revealed that the combinations of $NiCl_2$ and L1 or $NiBr_2$ and L2 in a 2:1 ratio, respectively, yield monodispersed structures (NiClL1 and NiBrL2; FIGS. 22 and 23). Although both MOFs have regular hexagonal topologies, NiClL1 forms a distinctly elongated hexagon that can also be observed by optical microscopy (FIG. 10). These observations demonstrate that minor structural differences in the organic ligand (i.e., L1: C≡C vs. L2: C=C) and the anion (Cl, Br) are key-factors that can be used to tune the topology of these MOFs at the microscopic level while a high level of uniformity is retained. Furthermore, the metal-to-ligand and solvent ratios can be used to control the MOF topologies. For instance, using $NiCl_2$ and L1 in a 1:1 ratio resulted in smaller hexagonal topologies, whereas changing the chloroform content resulted in elongated structures (FIG. 24). Addition of water to the reaction resulted in structural deformation (FIG. 24, panel F).

Figure 7:
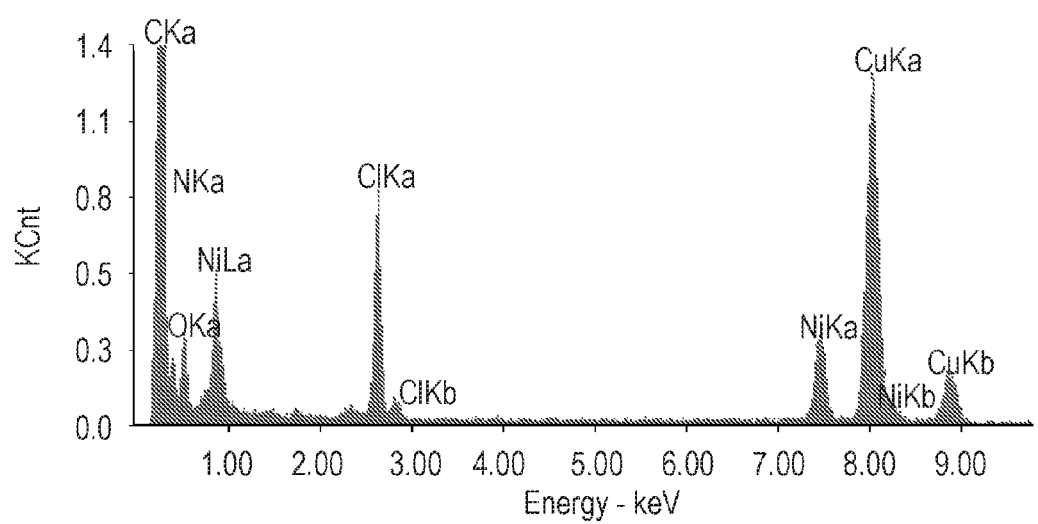
FIG. 7 shows a representative EDS measurement of a brick-like microstructure of NiClL1 using TEM (120 kV).
Figure 9:
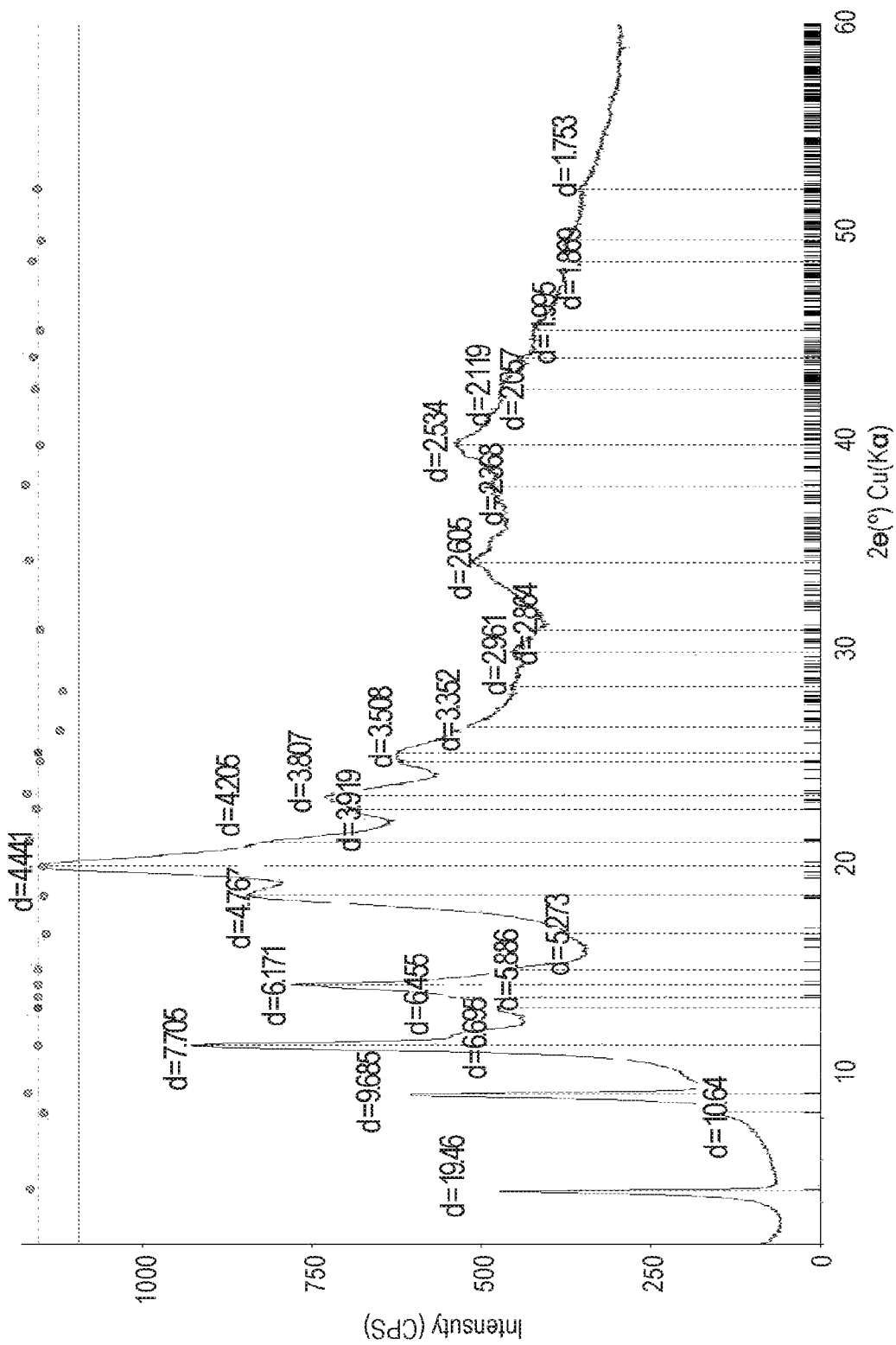
FIG. 9 shows representative XRD spectrum of NiClL1.
Figure 25:
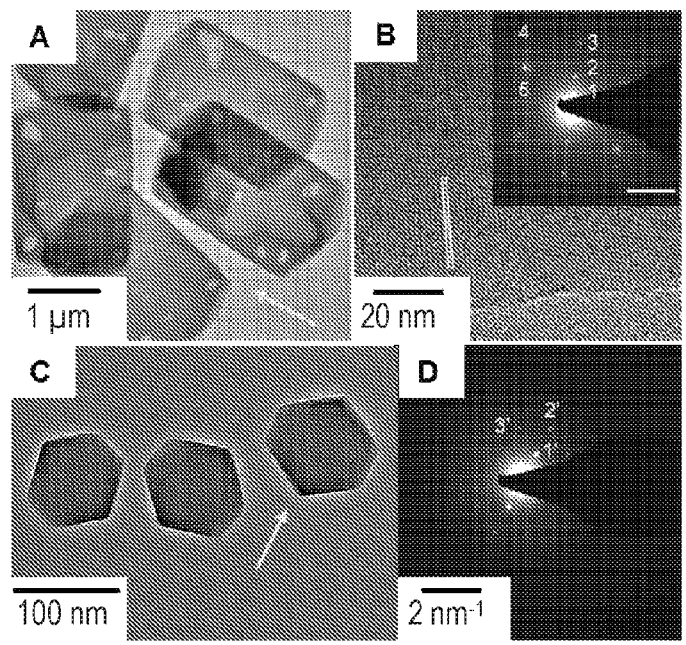
FIG. 25 shows TEM images and SAED of the nickel containing microstructures. Panel A—TEM image of NiClL1; Panel B—high magnification TEM image showing lattice planes in a single crystal of NiClL1, inset: SAED pattern arising from NiClL1, scale bar=2 $nm^{-1}$, with d-spacing corresponding to 1:1.79 nm, 2:0.9 nm, 3:0.46 nm, 4:0.42 nm, 5:0.49 nm; Panel C—TEM image of NiBrL2; and Panel D—SAED pattern arising from NiBrL2, with d-spacing corresponding to 1':0.95 nm, 2':0.49 nm, 3':0.55 nm. For SAED, the crystal orientation (longest axis) is indicated by the yellow arrow in panels A and C.
Figure 26:
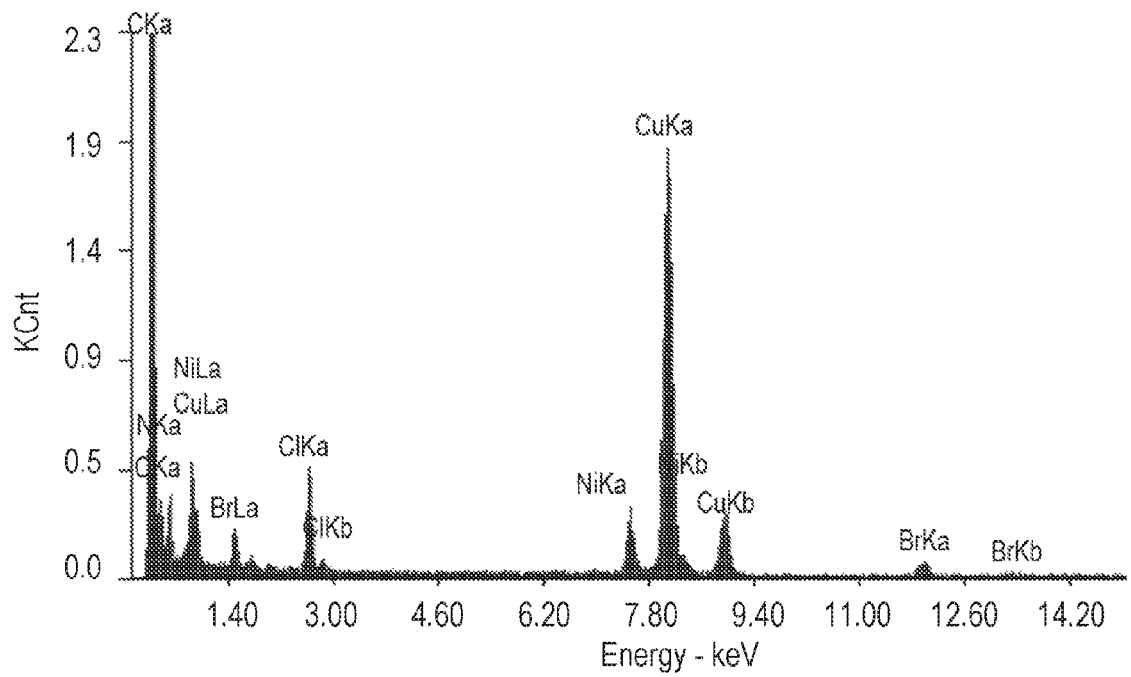
FIG. 26 shows representative EDS of NiBrL2 using TEM (120 kV).
Figure 27:
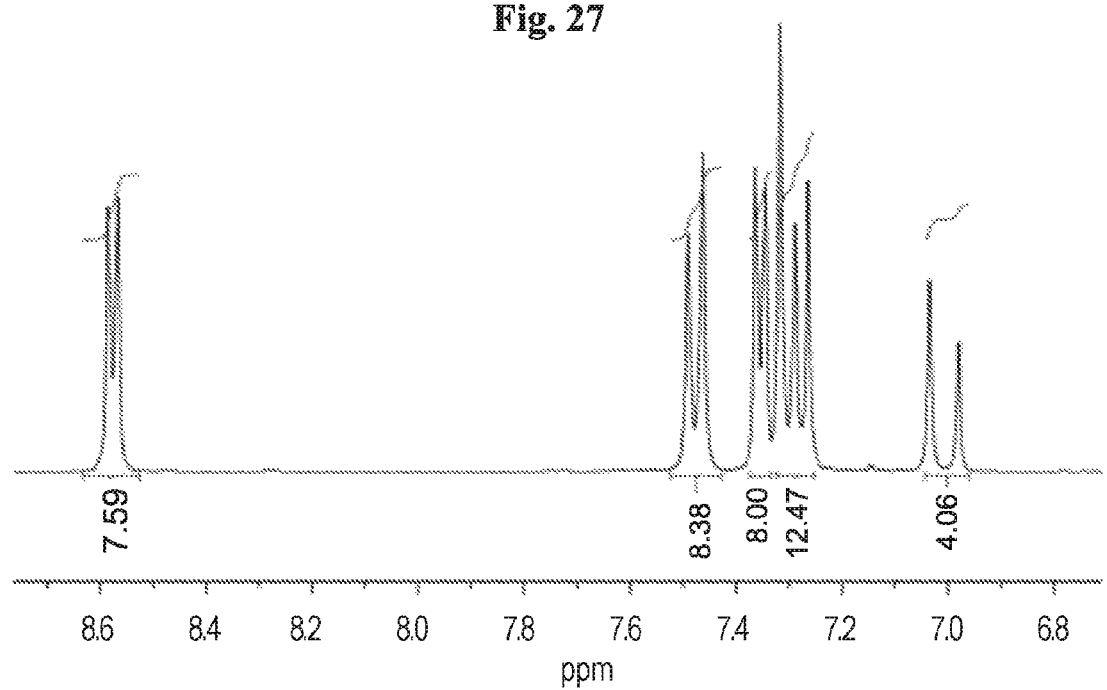
FIG. 27 shows representative $^1H$ NMR spectrum ($CDCl_3$) of the $CHCl_3$ extract after reacting CuBrL2 with conc. HCl and neutralizing with $Et_3N$. The spectrum corresponds to pure L2.

AFM measurements of NiClL1 and NiBrL2 confirmed the topologies and allowed precise measurement of the structure height (FIG. 3), as well as determination of mechanical properties (materials and methods are available as supplementary materials on Science Online). The elastic modulus of NiClL1 measured by AFM nanoindentation is 5-6 GPa, which is similar to values reported for organic crystals (Roberts et al., 1991). The crystalline nature of these two MOFs was unambiguously demonstrated by SAED (FIG. 25). XRD measurements of NiClL1 indicated also the formation of ordered structures (FIG. 9). The elemental composition of the MOFs was qualitatively confirmed by X-ray EDS, showing peaks corresponding to all characteristic atoms (nitrogen, metal and the anions) (FIGS. 7 and 26). The presence of the ligands is confirmed by FT-IR spectroscopy showing peaks corresponding to the ligand framework of NiClL1 and NiBrL2 that are shifted as compared to the free ligands (FIG. 5). The molecular structures of L1 and L2 are unlikely to be affected by the solvothermal conditions in the presence of these nickel salts. This assumption was verified by dissolving the MOFs under strong acidic conditions (pH<1), and subsequent isolation and characterization of the organic components. $^1H$ and $^{13}C\{^1H\}$ NMR spectroscopy (FIGS. 6 and 27), and mass-spectrometry (ESI-MS and MALDI-TOF) confirmed the ligand stability. SQUID measurements revealed paramagnetic behavior for both NiClL1 and NiBrL2. The ZFC and FC dependences were found to be superimposed (FIG. 20A, 21). These magnetic properties are in agreement with a near tetrahedral or an octahedral coordination geometry of the metal center (Bridgeman, 2008).

Figure 28:
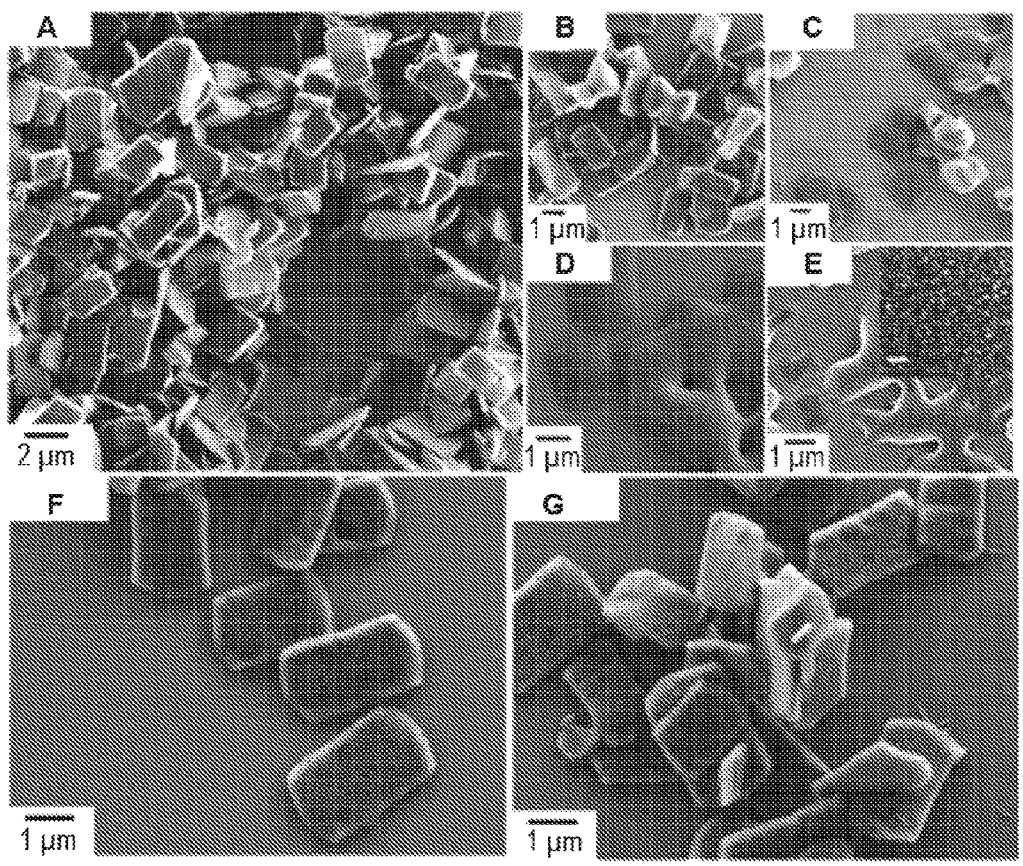
FIG. 28 shows RTP of NiClL1. Panels A-E: RTP under 10% $H_2/N_2$ (inset scale bar=100 nm). Panels F-G: RTP under vacuum. The experiments were done on NiClL1 drop-casted in silicon substrates, for 5 min.
Figure 29:
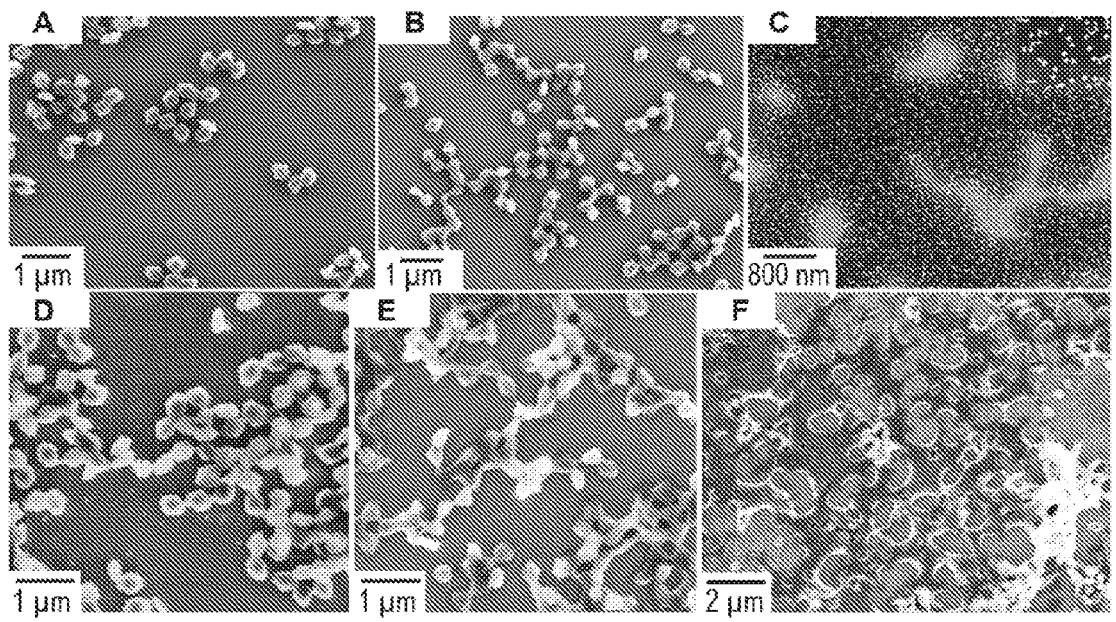
FIG. 29 shows RTP of NiBrL2. Panels A-C: RTP under 10% $H_2/N_2$ (inset scale bar=60 nm). Panels D-F: RTP under vacuum. The experiments were done on NiBrL2 drop-casted in silicon substrates, for 5 min.

The isolated NiClL1 and NiBrL2 are air stable at RT in the dark for at least one year. Immersing these MOFs in DMF or water for several months does not induce any observable change in their microstructure. TGA of NiClL1 showed a relatively small weight decrease of 3.4% around 86° C. corresponding with the loss of $CHCl_3$ (FIG. 17). There was 30% weight loss at 1000° C. RTP of NiClL1 and NiBrL2 under a stream of 10% $H_2/N_2$ and subsequent SEM analysis indicated that the structures were retained at 200° C. Clear deformation for both NiClL1 and NiBrL2 was observed at higher temperatures (FIGS. 28 and 29). The structures were found to be decorated with metallic nanoparticles (ø≈20 nm) at ≥400° C. The topological stability of NiClL1 under vacuum is even higher, indicating that the thermal stability is affected by $H_2$.

Figure 18:
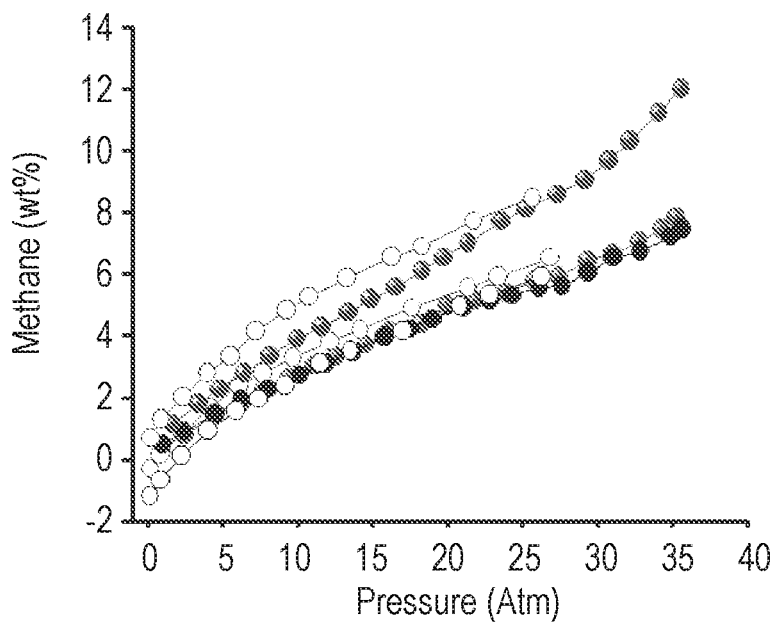
FIG. 18 shows methane adsorption-desorption isotherms for NiClL1. The sample was activated by vacuum treatment at 120° C. before exposing to methane at RT, 0° C. and −78.5° C. Adsorption (full red circle) and desorption (empty red circle) isotherms at RT. Adsorption (full blue circle) and desorption (empty blue circle) isotherms at 0° C. Adsorption (full green circle) and desorption (empty green circle) isotherm at −78.5° C.
Figure 19:
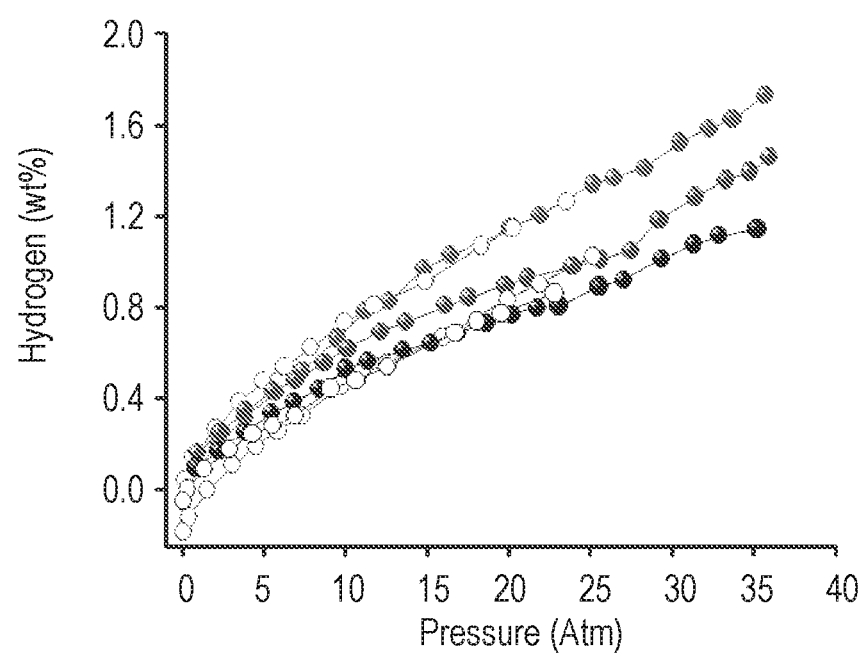
FIG. 19 shows adsorption isotherms (at 78.5K) for $H_2$ for NiClL1 activated at 70° C., 100° C. and 120° C. Adsorption (full red circle) and desorption (empty red circle) isotherms after activation at 70° C. Adsorption (full green circle) and desorption (empty green circle) isotherms after activation at 100° C. Adsorption (full blue circle) and desorption (empty blue circle) isotherms after activation at 120° C.

The porosity of NiClL1 was demonstrated by gas adsorption analysis. NiClL1 was activated at 120° C. under high vacuum for several hours to evaluate its adsorption/release efficiency for natural gas ($CH_4$). The $CH_4$ adsorption is 7.5 wt % at 0-20° C., and 11.7 wt % at −78.5° C. under a pressure of 35 atm. The hysteresis between adsorption and desorption runs is negligible, confirming the microporosity and the reversibility of the $CH_4$ uptake (FIG. 18). Gas pycnometry indicated a density of 0.687 g/cc. The $CH_4$ adsorption capacity of NiClL1 (75 $cm^3$ STP/$cm^3$) is in the range of that of COF-10, $Cd_2(AZPY)_3NO_3$, $Co_2(4,4'-BPY)_2(NO_3)_4$, $Cu_2(PIA)_2(NO_3)_4$ and the commerically available Basolite A520 (Manson et al., 2014; Adisa et al., 2012).

Figure 30:
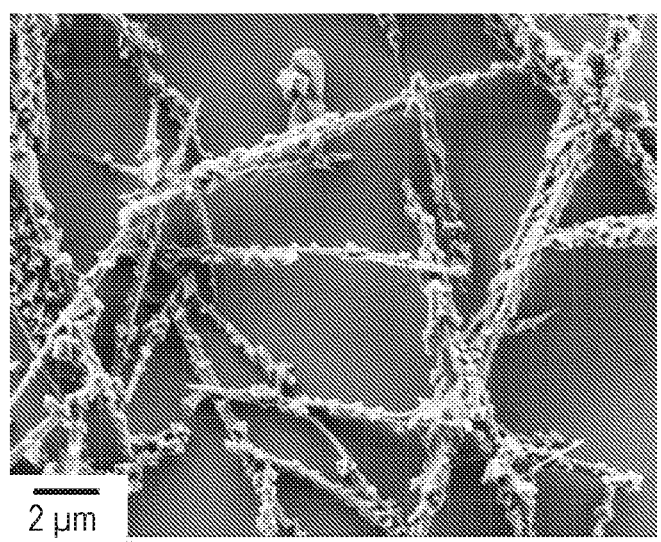
FIG. 30 shows SEM image of CuClL2. Reaction conditions: 1 eq. L2, 2 eq. $CuCl_2$, 3:1 (v/v) $DMF/CHCl_3$, 105° C., 5 days.
Figure 31:
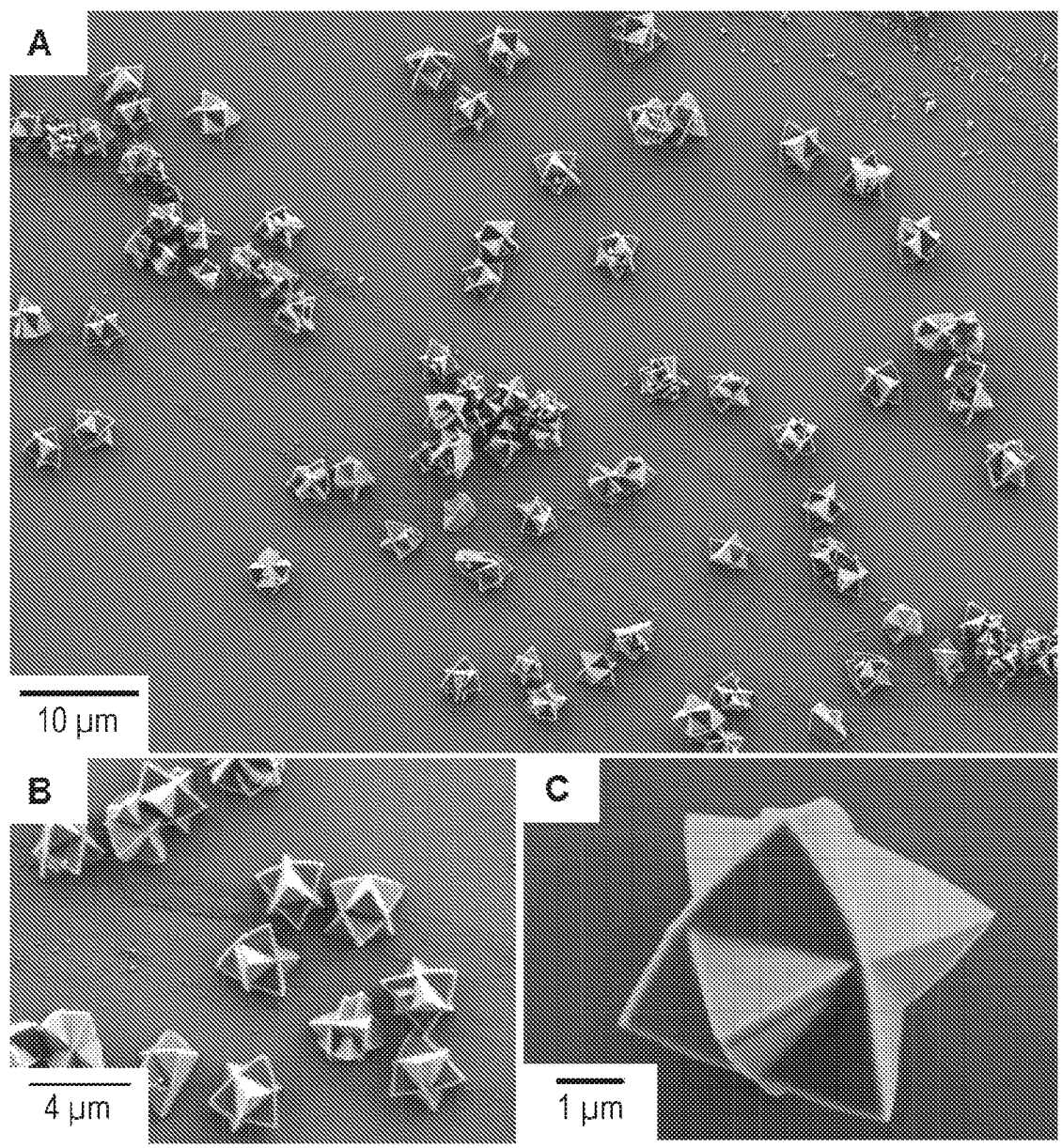
FIG. 31 shows interpenetrating topologies of Cu bromide containing MOFs obtained by solvothermal synthesis. SEM images (panels A-C) of CuBrL2. Reaction conditions: $CuBr_2$:L2=2:1, $DMF/CHCl_3$=3:1 v/v, 105° C., 5 days.

The use of Cu salts resulted in MOFs with strikingly differently structures. Non-uniform structured MOFs were obtained with $CuCl_2$ and L2 (FIG. 30). However, the reaction of $CuBr_2$ with L2 resulted in the formation of two interpenetrating tetrahedra (stella octangula) which can be described as a 3D extension of the Star of David (CuBrL2; FIG. 31). The reaction conditions are identical to those used for the formation of NiClL1 and NiBrL2 (FIG. 22). The crystalline nature of the Cu-based MOF was unequivocally confirmed by XRD; a powder XRD pattern similar to NiClL1 was obtained.

Figure 32:
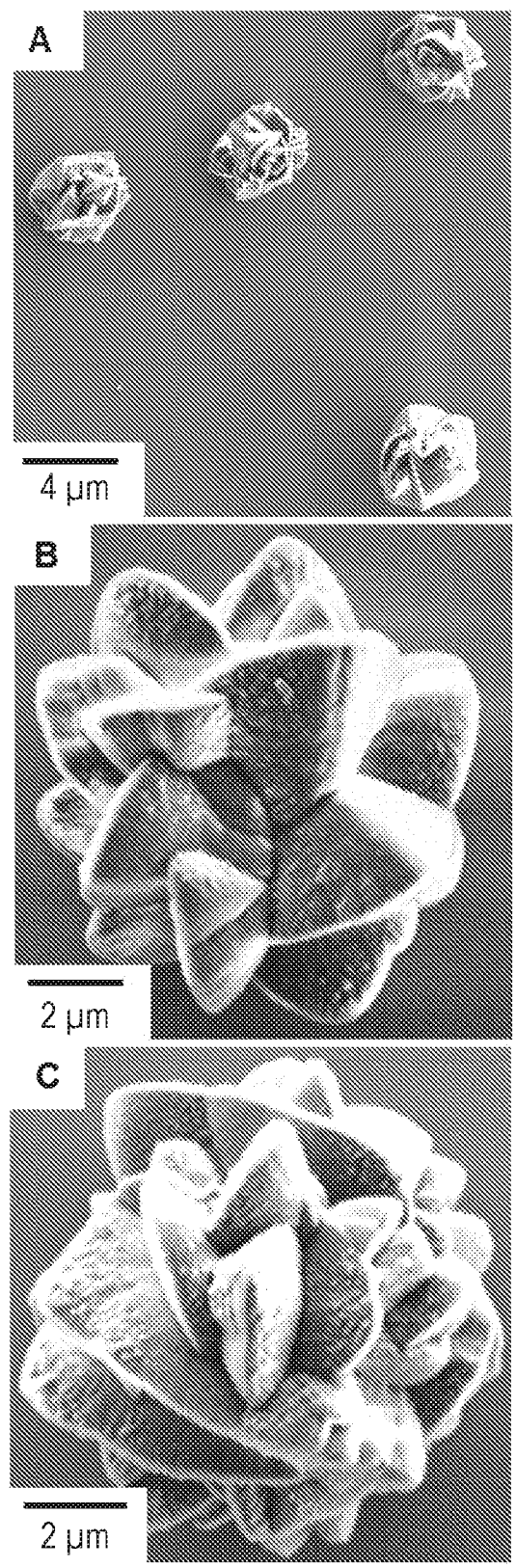
FIG. 32 shows interpenetrating topologies of Cu nitrate containing MOFs obtained by solvothermal synthesis. Representative SEM images (panels A-C) of $Cu(NO_3)L2$. Reaction conditions: $Cu(NO_3)_2$:L2=1:1, $DMF/CHCl_3$=3:1 v/v, 105° C., 5 days.
Figure 33:
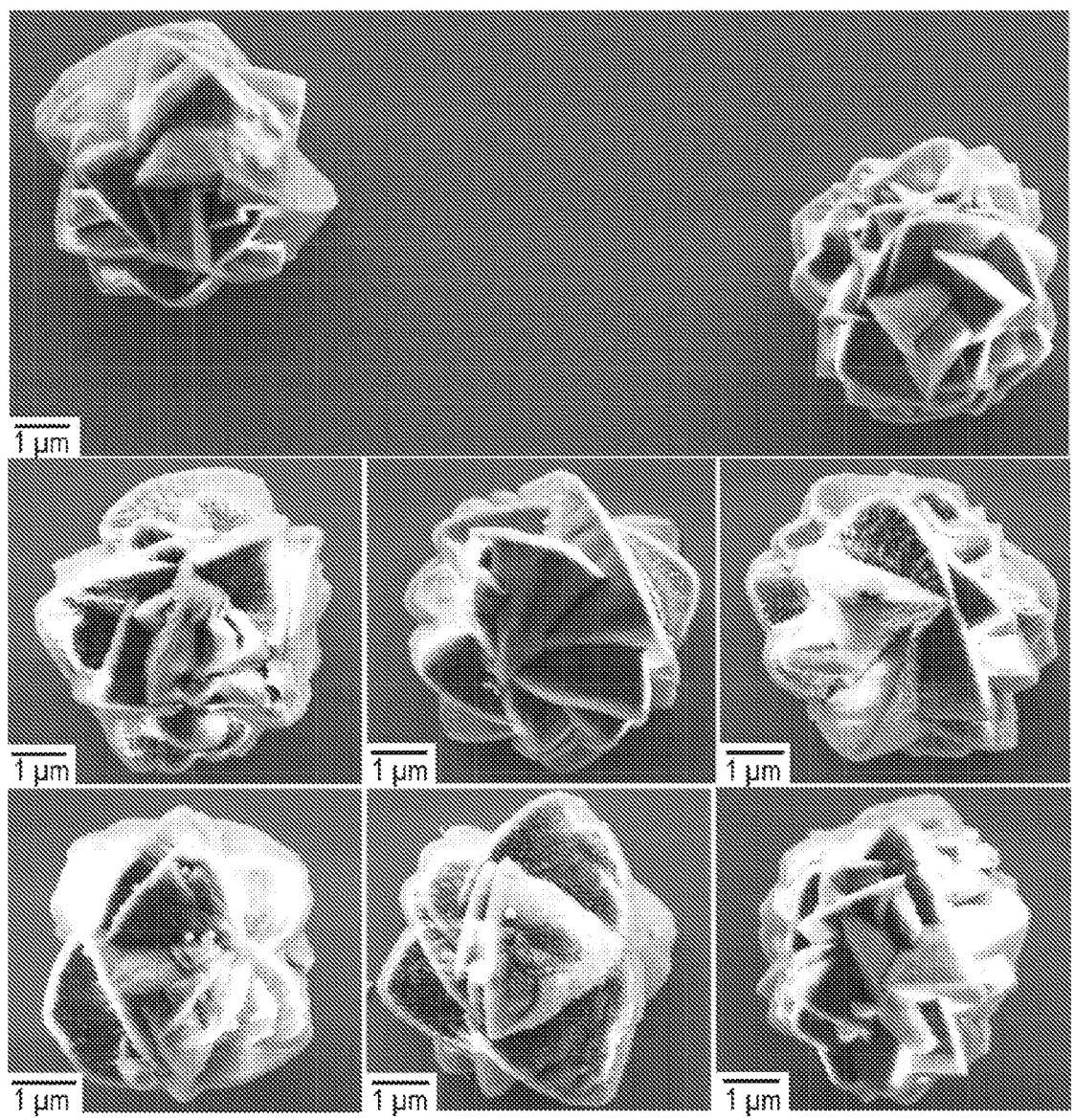
FIG. 33 shows examples of SEM images of $Cu(NO_3)L2$ (1 eq. L2, 1 eq. $Cu(NO_3)_2$, 3:1 (v/v) $DMF/CHCl_3$, 105° C., 5 days).
Figure 34A:
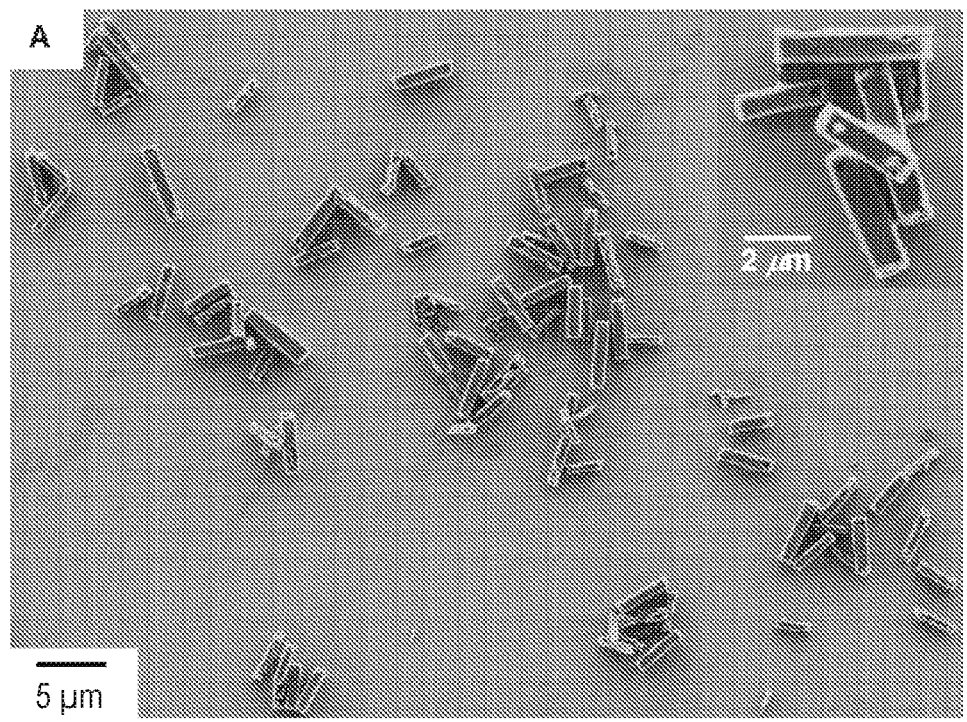
FIGS. 34A-34B show rectangular topologies of Cu nitrate containing MOFs obtained by solvothermal synthesis under inert atmosphere. (34A) Representative SEM image of $Cu(NO_3)L2$. (34B) Histograms showing the size distribution of $Cu(NO_3)L2$. Length: 3.65±0.95 µm, breadth: 0.675±0.09 µm. Reaction conditions (using dry solvents, under nitrogen): $Cu(NO_3)_2$:L2=1:1, $DMF/CHCl_3$=3:1 v/v, 105° C., 5 days.
Figure 34B:
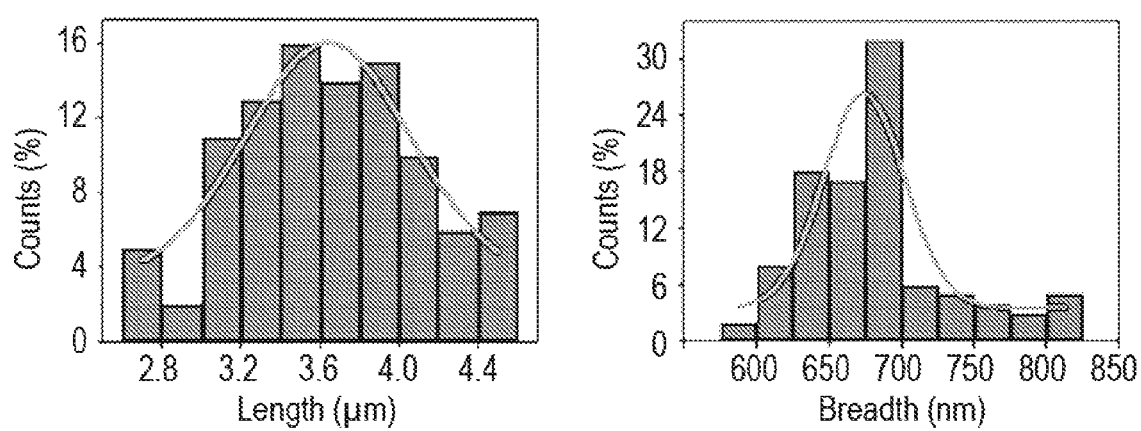
Figure 35:
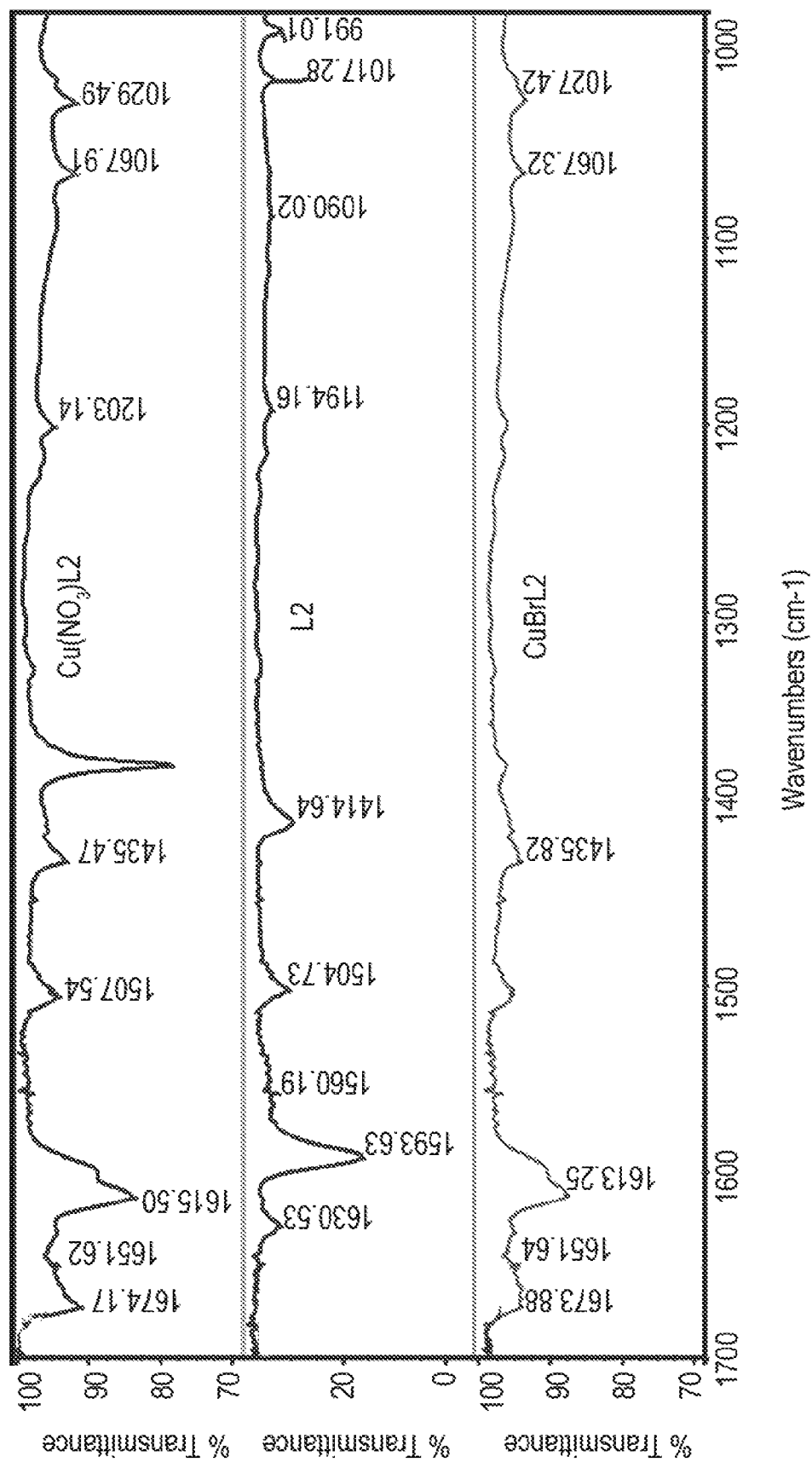
FIG. 35 shows FT-IR spectra of L2, $Cu(NO_3)L2$ and CuBrL2 (KBr pellet).

The nature of the anions and the metal-to-ligand ratio are also key parameters for the formation of well-defined Cu-based MOFs. The use of $Cu(NO_3)_2$ and a 1:2 (metal:L2) ratio resulted in ill-defined structures, contrasted with the higher degree of uniformity obtained for a 1:1 ratio. The latter resulted in flower-like topologies ($Cu(NO_3)L2$; FIGS. 32 and 33). Interestingly, performing this reaction with rigorous exclusion of air and use of dry solvents resulted in the formation of rectangular prisms with an average length of 3.65±0.95 µm and breadth of 0.675±0.09 µm ($Cu(NO_3)L2$; FIG. 34). In contrast to the other Cu-based MOFs, $Cu(NO_3)L2$ does not show any evidence of interpenetration. The presence and coordination of L2 is confirmed by FT-IR spectroscopy showing peaks corresponding to the ligand framework of CuBrL2 and $Cu(NO_3)L2$ (FIG. 35). Dissolving the Cu-based MOFs under acidic conditions, and subsequent isolation and characterization of L2 by NMR spectroscopy and mass-spectrometry confirmed its stability. The three Cu-based MOFs were found to be less uniform than NiClL1 and NiBrL2; however, they still have a common structural motif. The lesser degree of uniformity for the Cu-based MOFs might be related to their higher structural complexity and larger diversity of possible structures.

Figure 36:
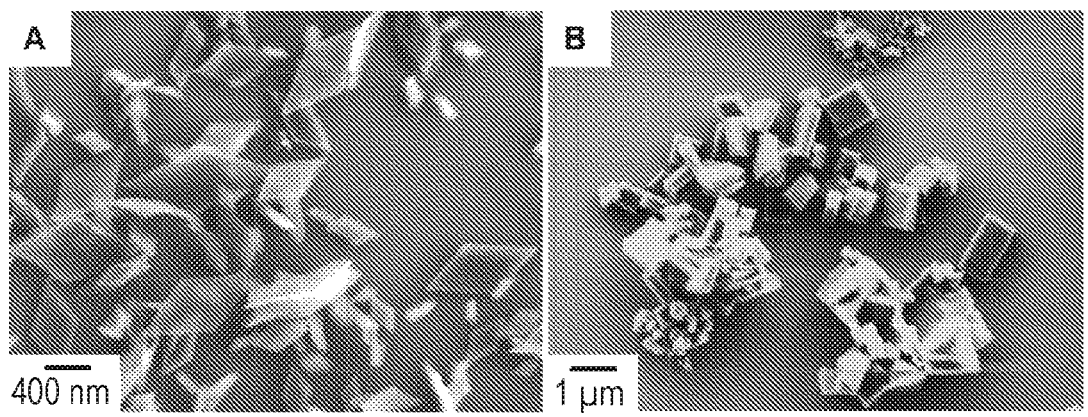
FIG. 36 shows effect of variations in solvent and temperature on the structure of $Cu(NO_3)L2$. SEM image of the structures obtained using $DMSO/CHCl_3$ (4 ml, 3:1 V/V) at 60° C. (panel A); and $PhCN/CHCl_3$ (4 ml, 3:1 v/v) at 60° C. (panel B). Reaction conditions: $Cu(NO_3)_2.3H_2O$ (3.3 mg, 13.6 mol), $CHCl_3$ solution (1.0 ml) of L2 (5.0 mg, 6.8 mol), 60° C., 5 days, without stirring and with exclusion of light. Similar structures were obtained at 105° C.
Figure 37:
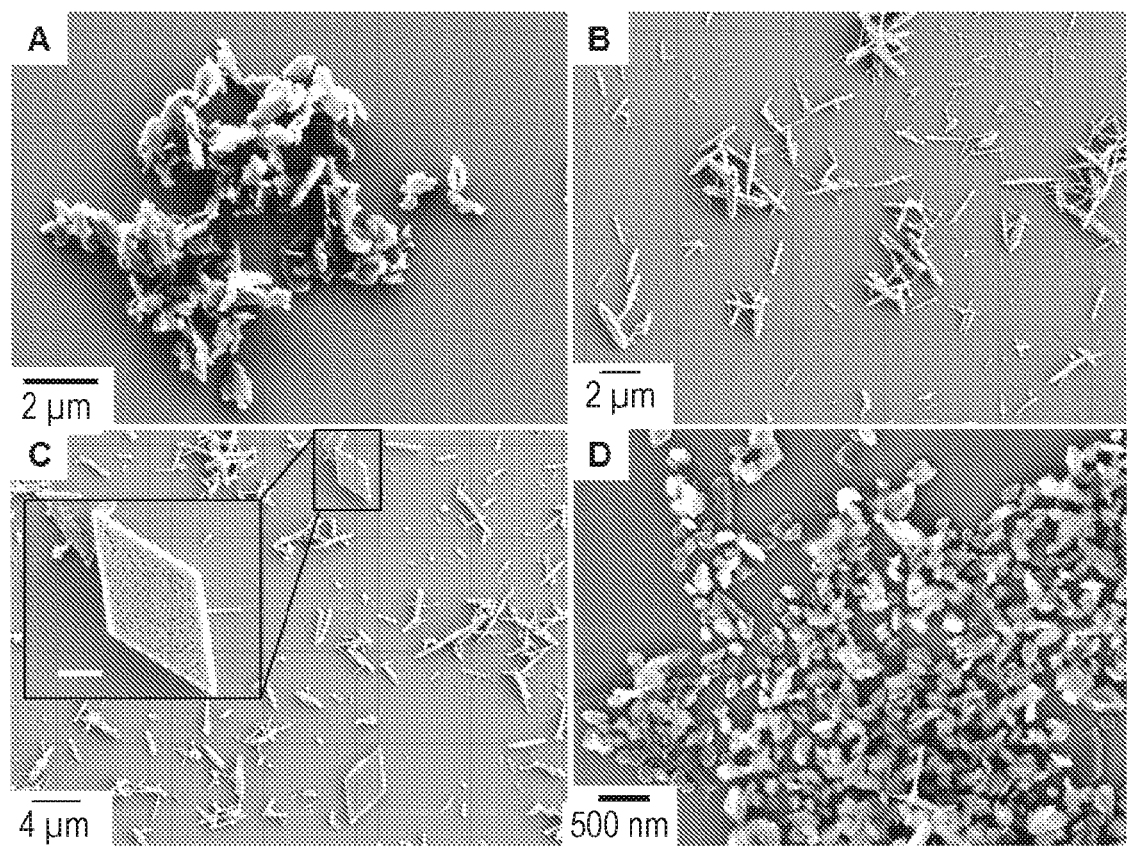
FIG. 37 shows effect of variations in solvent and temperature on the structure of CuBrL2. SEM image of the structures obtained using $PhCN/CHCl_3$ (4 ml, 3:1 v/v) at 60° C. (panel A); $DMF/MeCN/CHCl_3$ (4 ml, 1.5:1.5:1 v/v/v) at 60° C. (panel B); $MeCN/CHCl_3$ (4 ml, 3:1 v/v) at 60° C. (panel C); and $DMSO/CHCl_3$ (4 ml, 3:1 v/v) at 60° C. (panel D). Reaction conditions: CuBr (3 mg, 13.6 µmol), $CHCl_3$ solution (1.0 ml) of L2 (5.0 mg, 6.8 µmol), 60° C., 5 days, without stirring and with exclusion of light. Similar structures were obtained at 105° C.

The formation of the MOFs is probably a result of a complex cascade of assembly processes (Spokoyny et al., 2009; Oh and Mirkin, 2005). For both Ni and Cu-based MOFs the solvent composition plays a crucial role as well for the generation of uniform structures (FIGS. 24, 36 and 37). Varying the $DMF/CHCl_3$ ratios and/or addition of other solvents (PhCN, DMSO, water) leads to different assemblies.

Figure 38:
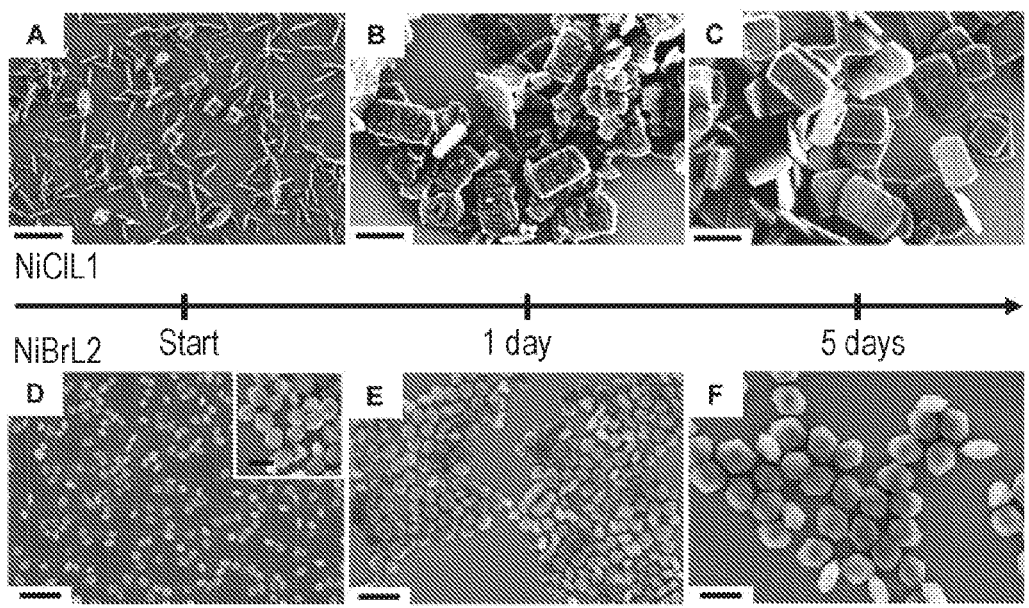
FIG. 38 shows time dependent SEM analysis for the formation of Ni-based MOFs. NiClL1: Immediately upon mixing a DMF solution of $NiCl_2$ and a $CHCl_3$ solution of L1 at RT (panel A); heating this mixture for 1 and 5 days at 105° C. (panel B and C, respectively). NiBrL2: Immediately upon mixing a DMF solution of $NiBr_2$ and a $CHCl_3$ solution of L2 at RT (panel D); heating this mixture for 1 and 5 days at 105° C. (panels E and F, respectively). Scale bar: (panels A-C=2 µm; panels D-F=500 nm; inset panel D=200 nm).
Figure 39:
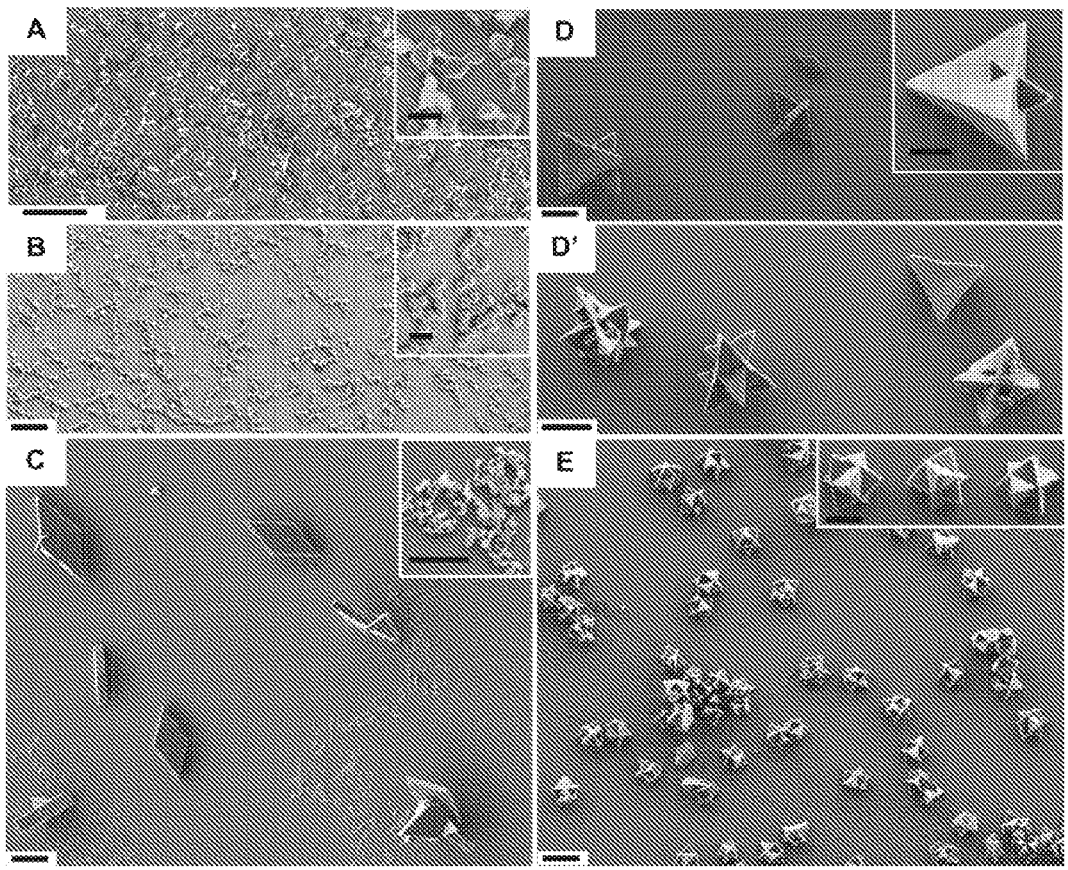
FIG. 39 shows time dependent SEM analysis for the formation of CuBrL2. Topologies of CuBrL2 (panels A-E; scale bar=5 µm) obtained after: (panel A) immediately upon mixing a DMF solution of $CuBr_2$ and a $CHCl_3$ solution of L2 at RT. Inset scale bar=200 nm; (panel B) heating this mixture for 1.5 days at 105° C. Inset scale bar=2 µm; (panel C) heating the mixture for 2.5 days at 105° C. Inset scale bar=1 µm; (panels D,D') heating the mixture for 3.5 days at 105° C. Inset scale bar=2 µm; and (panel E) heating the mixture for 5 days at 105° C. Inset scale bar=2 µm.

Extending the electron microscope studies of the formation of the Ni- and Cu-based MOFs revealed interesting mechanistic information. A time-dependent analysis showed distinctly different pathways for the formation of the uniform structures obtained. Mixing the solutions of $NiCl_2$ and $NiBr_2$ salts with the corresponding ligand (L1 or L2) result in an immediate precipitation. Apparently, the process starts with the coordination of the ligand to the metal center as the first nucleation step as common in crystallizations and colloid synthesis. SEM analysis of NiClL1 aliquots taken immediately upon mixing showed the formation of a mixture of elongated (needles) and cubical structures (<1 µm; FIG. 38, panel A). Thermolysis of this mixture resulted in the formation of premature hexagonal structures, whose overall shape and size resembles the final product, but with coarse texture and edges (FIG. 38, panel B). Continuous heating for 5 days afforded the polished NiClL1 (FIGS. 23 and 38, panel C). Amorphous infinite coordination polymers (ICP) reported by Mirkin undergo annealing similar to the structural polishing observed here (Spokoyny et al., 2009; Jeon et al., 2009). The rough surfaces are likely ideal nucleation sites for the addition of more material. A different growth process operates for the formation of NiBrL2. In the initial stages of mixing, small and uniform crystallites (≈55 nm×27 nm) are formed having the same topology as the final product (NiBRL2; FIGS. 23 and 39, panel D). During the reaction, their size increases by almost fivefold (FIG. 38, panels D-E). For both the Ni-based MOFs, higher temperatures and pressure increases the average size of the nanostructures and decreases the number of smaller nanostructures. The higher surface energies of smaller structures can facilitate their dissolution generating new nuclei (Murray et al., 2001). Unlike the observed polishing process with NiClL1, for NiBRL2 a different mechanism is operating that involves regular crystal growth by addition of material to the nuclei with retention of the same basic shape over the course of formation (akin to Ostwald ripening).

The time-dependent SEM analysis of the growth of the Cu-based MOFs revealed a rather complicated sequence involving several intermediate structures. Mixing a solution of $CuBr_2$ with L2 resulted at RT in non-uniform plate-like structures (FIG. 39, panel A) which transform into laterally fused spheres upon heating after 1.5 days (diameter=650±50 nm, FIG. 39, panel B). Upon continuous heating much larger diamond-like structures (FIG. 39, panel C) and fused structures thereof were observed. Some spherical structures remained, albeit smaller (FIG. 39, panel C, inset). Interestingly, after 3.5 days mostly pyrimidal structures were present, most likely formed from a combination of fusion and nucleation (FIG. 39, panels D,D'). The inset of FIG. 39, panel D, clearly shows a penetrating twin-type structure. The initial pyrimidal shapes are formed by fusion of the diamond-like structures (FIG. 39, panels C,D), and their facets subsequently act as nucleation sites to afford the kinetically complex products seen in FIG. 39, panel D'. Further heating results in the thermodynamically robust CuBrL2 (FIGS. 32 and 39, panel E), that have the appearance of twinned crystals.

Figure 40:
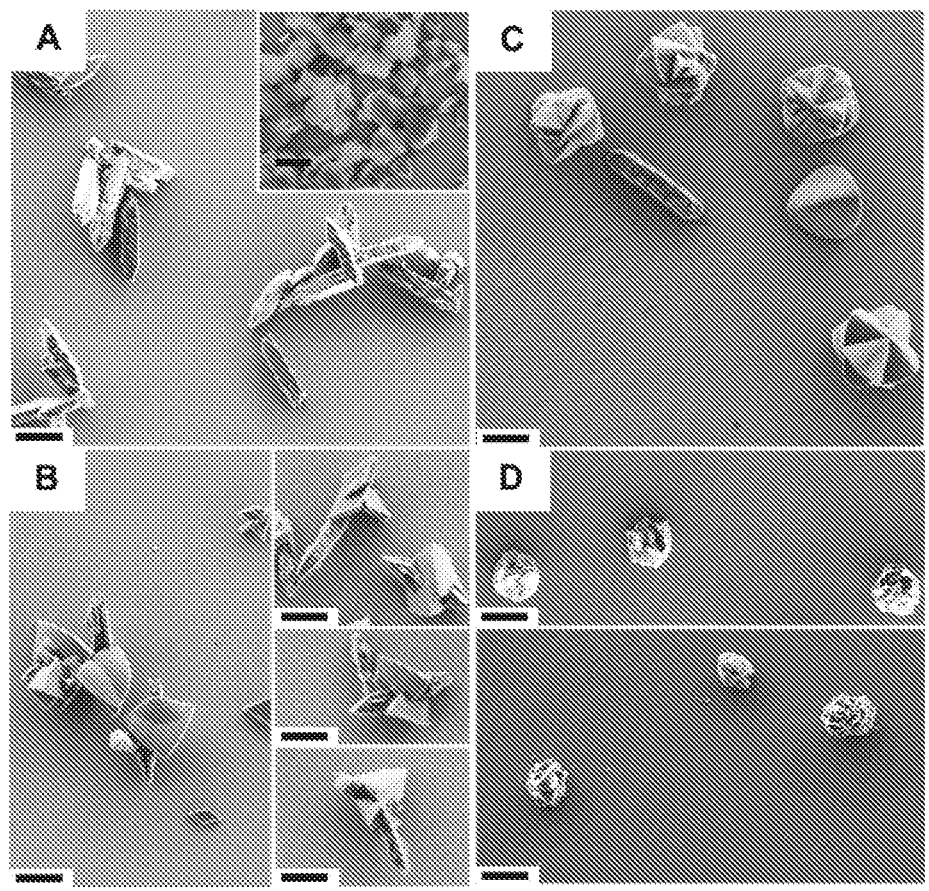
FIG. 40 shows time dependent SEM analysis for the formation of $Cu(NO_3)L2$. Topologies of $Cu(NO_3)L2$ (panels A-D; scale bar=5 µm) obtained after: (panel A) heating a DMF solution of Cu(NO$_3$)$_2$ and a CHCl$_3$ solution of L2 for 1 day at 105° C. Inset: immediately after mixing Cu(NO$_3$)$_2$ and L2. Inset scale bar=200 nm; (panel B) heating the mixture for 2.5 days at 105° C.; (panel C) heating the mixture for 3.5 days at 105° C.; and (panel D) heating the mixture for 5 days at 105° C.

The formation of $Cu(NO_3)L2$ starts with the formation non-uniform plate-like structures similar to the ones observed for CuBrL2 (FIG. 40, panel A, inset). After heating for one day, irregular rectangular prisms were formed (FIG. 40, panel A), that transform after 2.5 days into interpenetrated structures (FIG. 40, panel B). Upon continued heating, these apparent threaded systems undergo another fusion process to provide the flower-like topologies (FIG. 40, panels C,D).

Our observations show that the formation of metal-organic microcrystals with a uniform size distribution can be readily achieved by solvothermal synthesis. Others have been using solvothermal approaches for attaining structural modifications mainly at the molecular level (Stock and Biswas, 2011). In addition, crystal packing variation through systematic chemical modifications is known for many organic and other materials (Stock and Biswas, 2011; Zhao et al., 2011; Smulders et al., 2013; Wang et al., 2013; Shirman et al., 2008). However, such an approach to obtain uniform microcrystals is rare (Masoomi and Morsali, 2013; Ban et al., 2013). It is remarkable that varying the intramolecular structure (i.e., C≡C vs. C=C, Cl vs. Br, Ni vs. Cu) has such a striking effect on the formation, uniformity and topology of the here reported MOFs. Our approach to obtain uniformity at the (sub)-micron level is sensitive to the position of the metal in the perodic table, as well as the reaction time. For example, we have shown previously that the reaction of Pd(II) salts with L2 resulted in the formation of coordination-polymer nanotubes (Kaminker et al., 2011). Structural features and dimensions of such nanotubes are assembly dependent as shown by Aida et al. (Zhang et al., 2009). In the present study, mixtures of (sub)-microstructures were observed initially which gradually transformed into the homogeneously structured crystals. Although this work has not attempted to characterize the factors which predetermine the topology of such microstructures, the possibility of custom-designed topologies is enticing. Considering the range of parameters considered in this study, the possibility for shape-specificity and size uniformity in MOFs could be expected to be a wide and general phenomenon.

Study 3. Various Metal Organic Frameworks

In a series of experiments described herein below, various MOFs have been prepared using the general procedure described above, wherein different metal salts and reaction conditions are utilized.

Figure 41:
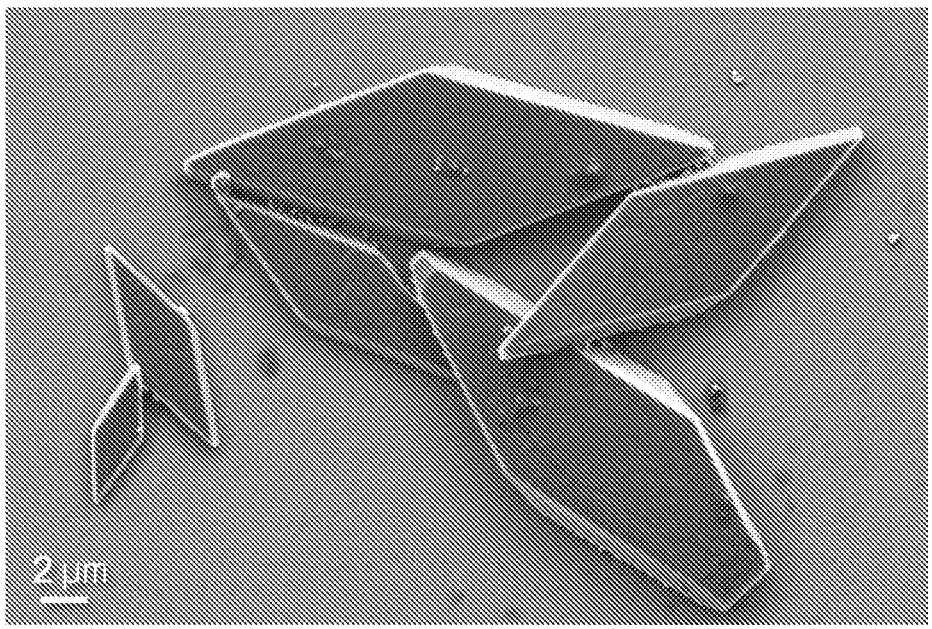
FIG. 41 shows MOFs prepared from a CHCl$_3$ solution of L1 and a DMF suspension of NiBr$_2$, under the conditions described in Study 3.

A $CHCl_3$ solution (1.0 ml) of L1 (5 mg, 6.9 µmol) was added to a DMF suspension (3.0 ml) of $NiBr_2$ (3 mg, 13.8 µmol) in an oven-dried glass pressure tube, which was sealed and heated for 5 days at 105° C. without stirring and with exclusion of light, followed by subsequent controlled cooling to RT over 9-10 h. at a rate of 10° C./h, resulting in a light green precipitate and was collected by centrifugation of the reaction mixture for ~10 min. at 5000 rpm and decanting the mother liquor (FIG. 41).

Figure 42:
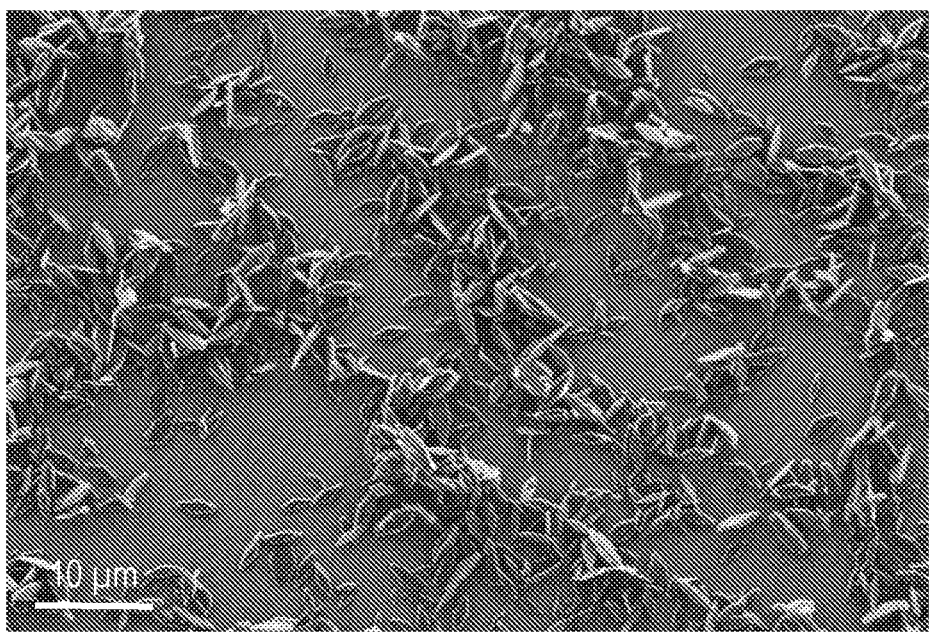
FIG. 42 shows MOFs prepared from a CHCl$_3$ solution of L1 and a DMF suspension of NiCl$_2$.6H$_2$O, under the conditions described in Study 3.

A $CHCl_3$ solution (2.0 ml) of L1 (5 mg, 6.9 µmol) was added to a DMF suspension (3.0 ml) of $NiCl_2.6H_2O$ (3.3 mg, 13.8 µmol) in an oven-dried glass pressure tube, which was sealed and heated for 5 days at 105° C. without stirring and with exclusion of light, followed by subsequent controlled cooling to RT over 9-10 h. at a rate of 10° C./h, resulting in a light green precipitate and was collected by centrifugation of the reaction mixture for ~10 min. at 5000 rpm and decanting the mother liquor (FIG. 42).

Figure 43:
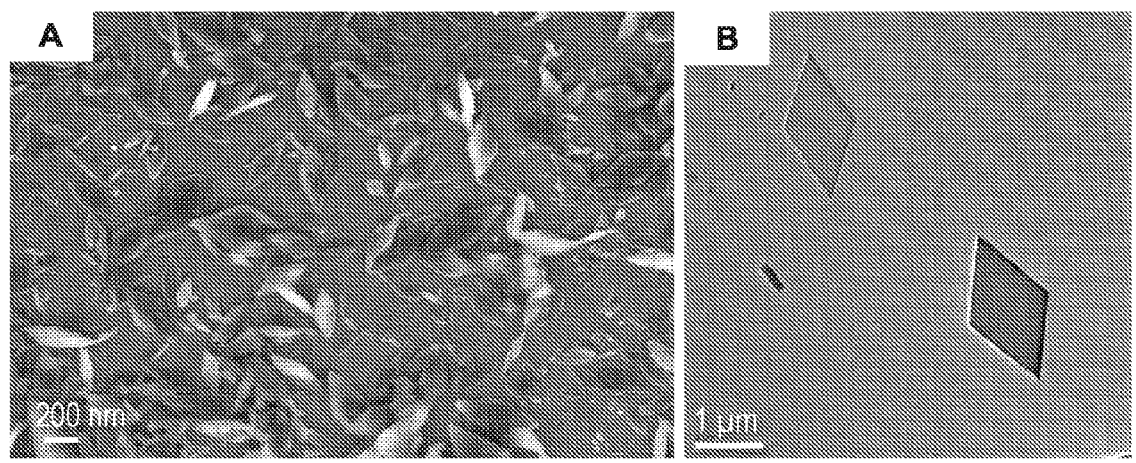
FIG. 43 shows SEM and TEM images (panels A and B, respectively) of MOFs prepared from a CHCl$_3$ solution of L2 and a DMF solution of NiCl$_2$.6H$_2$O, under the conditions described in Study 3.

A $CHCl_3$ solution (1.0 ml) of L2 (5.7 mg, 7.8 µmol) was carefully layered below a DMF solution (3.0 ml) of $NiCl_2.6H_2O$ (1.9 mg, 7.8 µmol) in an oven-dried glass tube, which was sealed and kept in the dark for 5 d, resulting in a light green precipitate and was collected by centrifugation for ~10 min. at 5000 rpm and decanting the mother liquor (FIG. 43).

Figure 44:
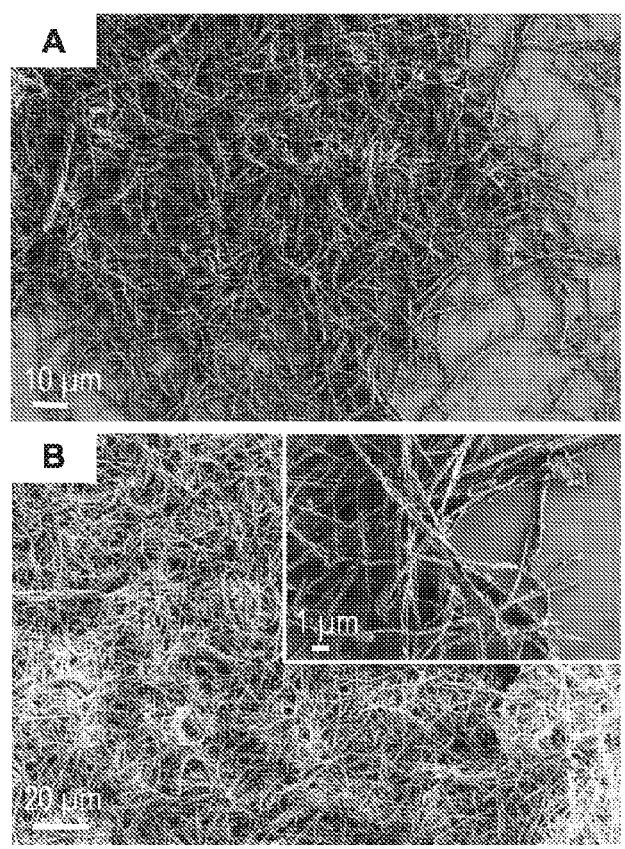
FIG. 44 shows MOFs prepared from a sonicated toluene solution of Pd(COD)Cl$_2$ and a toluene suspension of L2, under the conditions described in Study 3.

A sonicated toluene solution (2.0 ml) of $Pd(COD)Cl_2$ (4.5 mg, 15.6 µmol) was added to a toluene suspension (4.0 ml) of L2 (5.7 mg, 7.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a yellowish precipitate and was collected by centrifugation of the reaction mixture for ~10 min. at 5000 rpm and decanting the mother liquor (FIG. 44).

Figure 45:
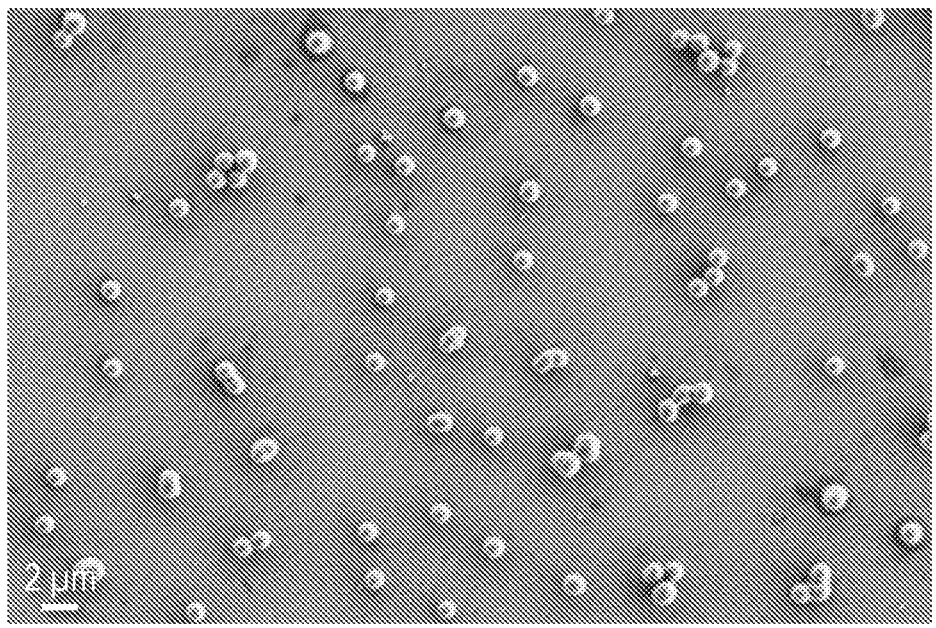
FIG. 45 shows MOFs prepared from a sonicated toluene suspension of PdCl$_2$ and a toluene suspension of L2, under the conditions described in Study 3.

A sonicated toluene suspension (2.0 ml) of $PdCl_2$ (2.8 mg, 15.6 µmol) was added to a toluene suspension (4.0 ml) of L2 (5.7 mg, 7.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a yellowish precipitate and was collected by centrifugation of the reaction mixture for 10 min. at 5000 rpm and decanting the mother liquor (FIG. 45).

Figure 46:
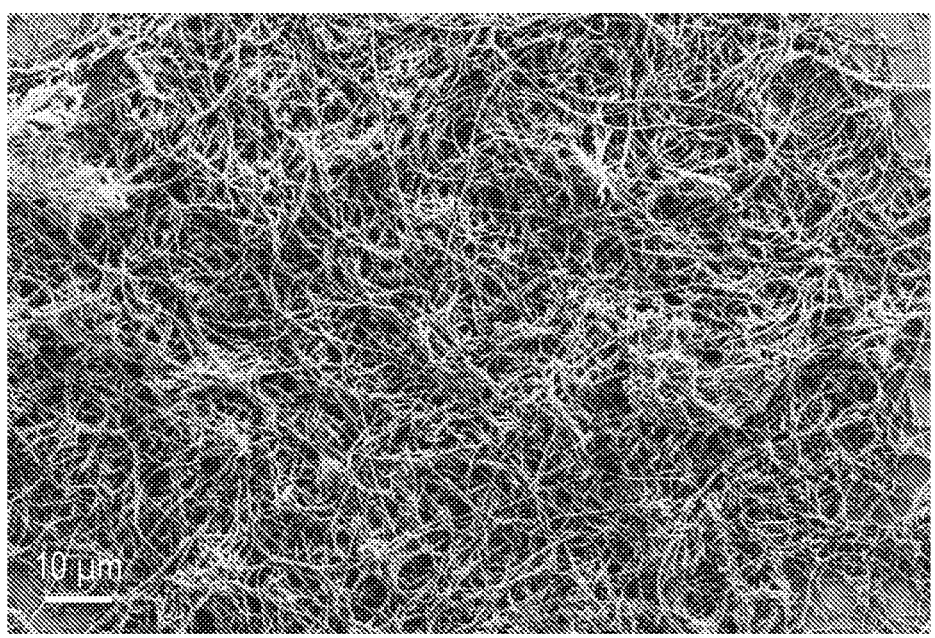
FIG. 46 shows MOFs prepared from an ethylbenzene solution of Pd(PhCN)$_2$Cl$_2$ and an ethylbenzene suspension of L2, under the conditions described in Study 3.

An ethylbenzene solution (2.0 ml) of $Pd(PhCN)_2Cl_2$ (5 mg, 15.6 µmol) was added to an ethylbenzene suspension (4.0 ml) of L2 (5.7 mg, 7.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a yellowish precipitate and was collected by centrifugation of the reaction mixture for ~10 min. at 5000 rpm and decanting the mother liquor (FIG. 46).

Figure 47:
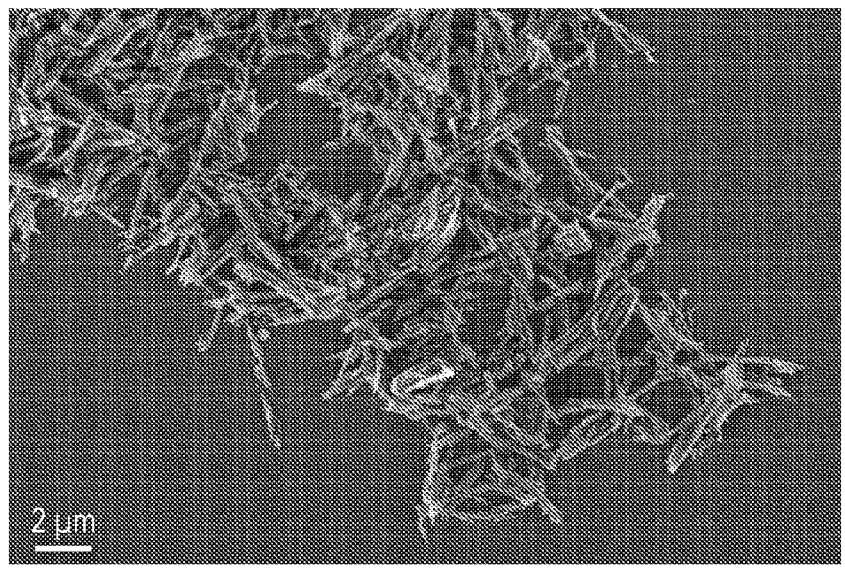
FIG. 47 shows MOFs prepared from a toluene solution of Pd(PhCN)$_2$Cl$_2$ and a heptane suspension of L2, under the conditions described in Study 3.

A toluene solution (3.0 ml) of $Pd(PhCN)_2Cl_2$ (5 mg, 15.6 µmol) was added to a heptane suspension (3.0 ml) of L2 (5.7 mg, 7.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a yellowish precipitate and was collected by centrifugation of the reaction mixture for ~10 min. at 5000 rpm and decanting the mother liquor (FIG. 47).

Figure 48:
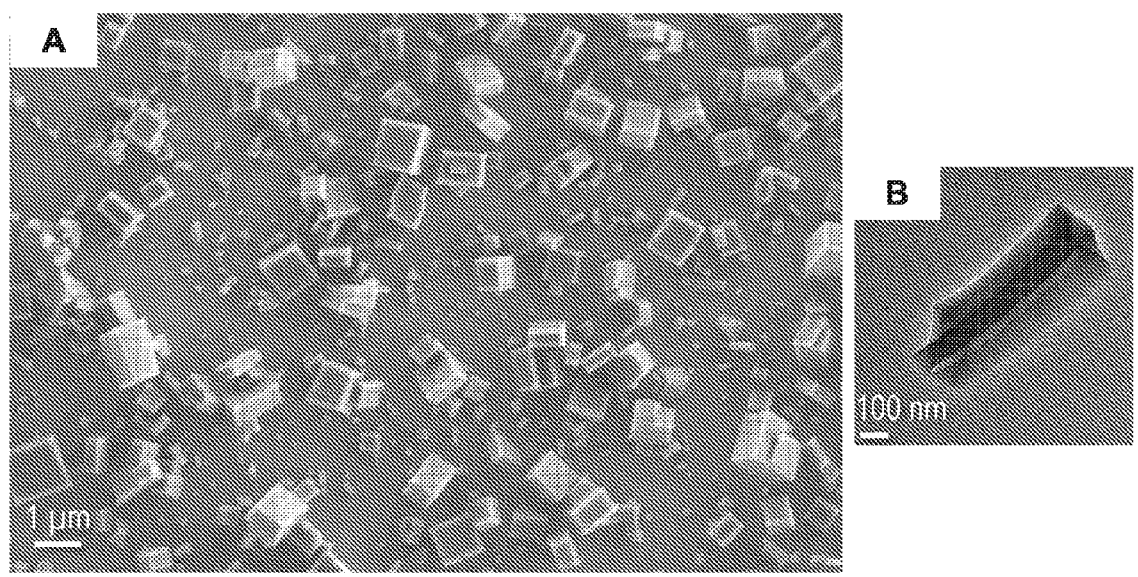
FIG. 48 shows MOFs prepared from a CHCl$_3$ solution of L2 and a DMF solution of Cu(OTf)$_2$, under the conditions described in Study 3.

A $CHCl_3$ solution (1.0 ml) of L2 (5.7 mg, 7.8 µmol) was carefully layered below a DMF solution (3.0 ml) of $Cu(OTf)_2$ (2.8 mg, 7.8 µmol) in an oven-dried glass tube, which was sealed and kept in the dark for 5 d, resulting in a light blue precipitate and was collected by centrifugation of the reaction mixture for ~10 min. at 5000 rpm and decanting the mother liquor (FIG. 48).

Figure 49:
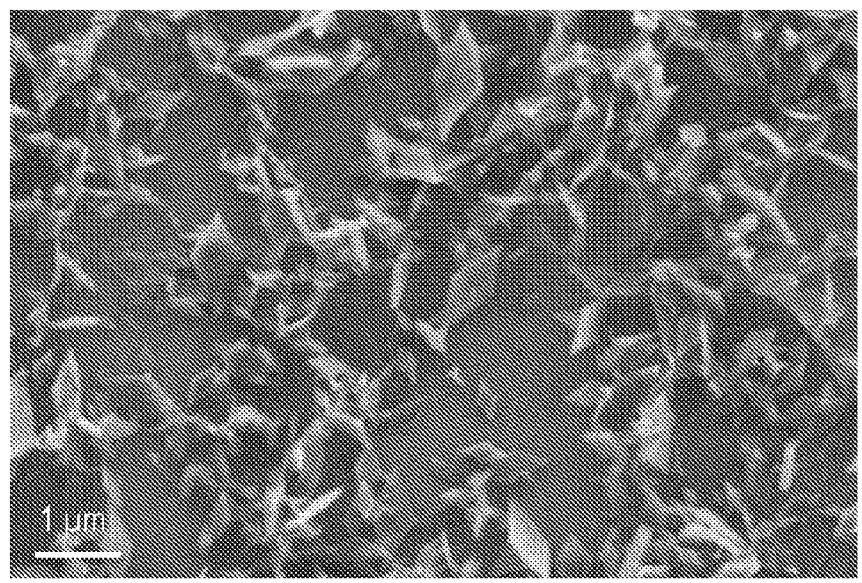
FIG. 49 shows MOFs prepared from a CHCl$_3$ solution of L2 and a DMF solution of Cu(OTf)$_2$, under the conditions described in Study 3.

A $CHCl_3$ solution (1.0 ml) of L2 (5.7 mg, 7.8 µmol) was carefully layered below a DMF solution (3.0 ml) of $Cu(OTf)_2$ (2.8 mg, 7.8 µmol) in an oven-dried glass tube, which was sealed and kept in the dark for 10 days and then heated for another 2 days at 60° C. without stirring and with exclusion of light, followed by subsequent cooling to RT temperature, resulting in a light blue precipitate and was collected by centrifugation of the reaction mixture for ~10 min. at 5000 rpm and decanting the mother liquor (FIG. 49).

Figure 50:
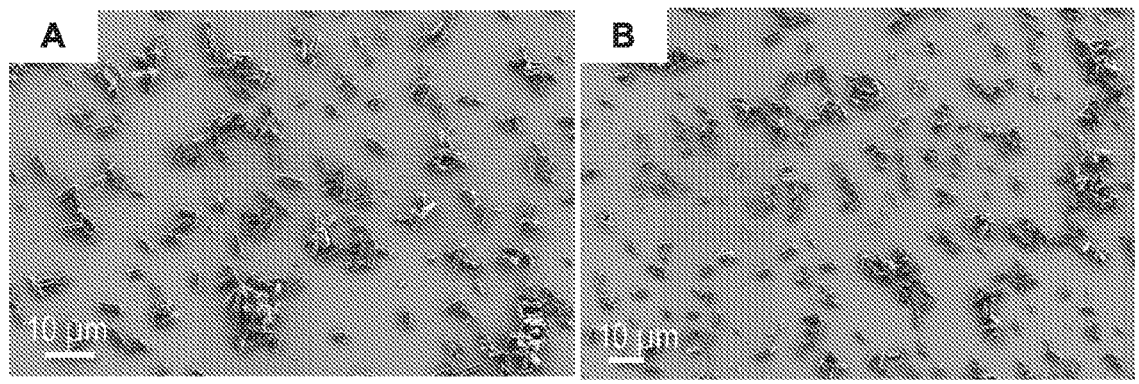
FIG. 50 shows MOFs prepared from a dry CHCl$_3$ solution of L2 and a dry DMF solution of Cu(NO$_3$)$_2$.3H$_2$O, under the conditions described in Study 3.

A dry $CHCl_3$ solution (1.0 ml) of L2 (5 mg, 6.8 µmol) was added to a dry DMF solution (3.0 ml) of $Cu(NO_3)_2.3H_2O$ (1.65 mg, 6.8 µmol) in an oven-dried glass pressure tube under $N_2$ atmosphere, which was sealed and heated for 6 days at 105° C. without stirring and with exclusion of light, followed by subsequent controlled cooling to RT over 9-10 h. at a rate of 10° C./h, resulting in a light green precipitate and was collected by centrifugation of the reaction mixture for ~10 min. at 5000 rpm and decanting the mother liquor (FIG. 50).

Figure 51:
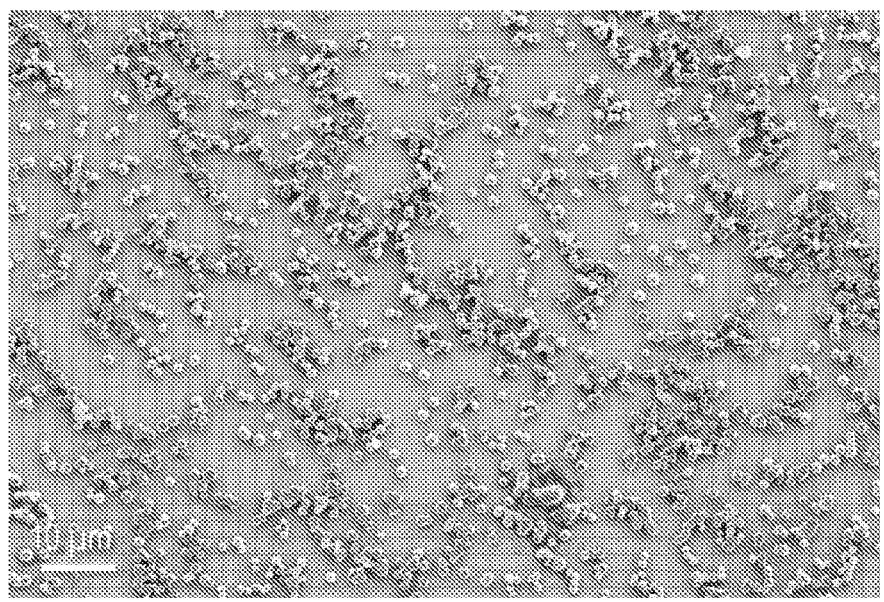
FIG. 51 shows MOFs prepared from a CHCl$_3$ solution of L2 and a DMF solution of Zn(OAc)$_2$.2H$_2$O, under the conditions described in Study 3.

A $CHCl_3$ solution (1.0 ml) of L2 (5 mg, 6.8 µmol) was added to a DMF solution (3.0 ml) of $Zn(OAc)_2.2H_2O$ (3 mg, 13.6 µmol) in an oven-dried glass pressure tube, which was sealed and heated for 2 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 51).

Figure 52:
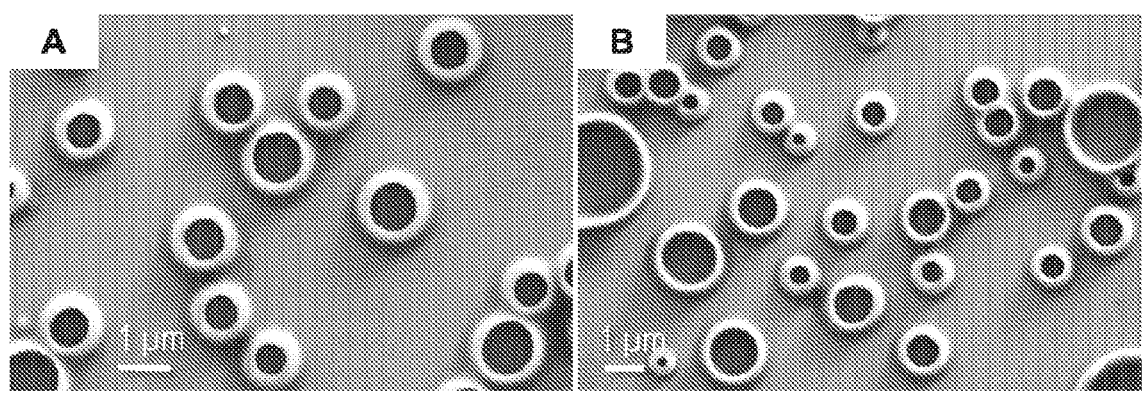
FIG. 52 shows MOFs prepared from a CHCl$_3$ solution of L2 and a DMF solution of Zn(OAc)$_2$.2H$_2$O, under the conditions described in Study 3.

A $CHCl_3$ solution (1.0 ml) of L2 (5 mg, 6.8 µmol) was added to a DMF solution (3.0 ml) of $Zn(OAc)_2.2H_2O$ (3 mg, 13.6 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 52).

Figure 53:
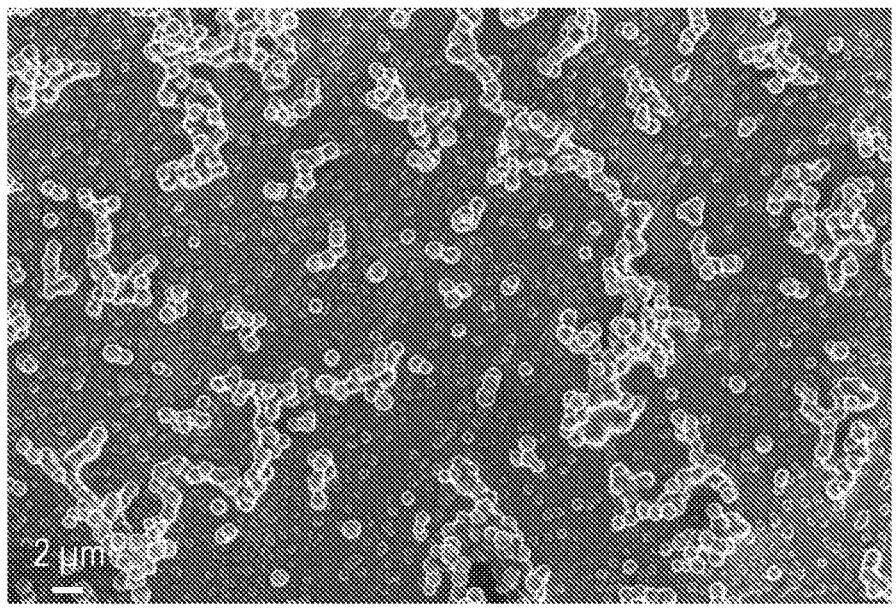
FIG. 53 shows MOFs prepared from a CHCl$_3$ solution of L2 and a DMF solution of ZnCl$_2$.2H$_2$O, under the conditions described in Study 3.

A $CHCl_3$ solution (1.0 ml) of L2 (5 mg, 6.8 µmol) was added to a DMF solution (3.0 ml) of $ZnCl_2.2H_2O$ (0.92 mg, 6.8 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 53).

Figure 54:
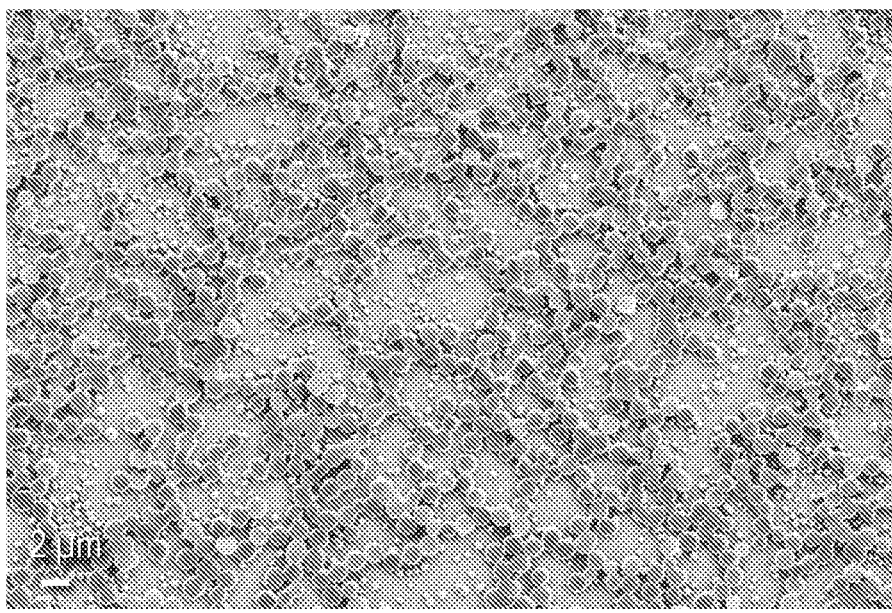
FIG. 54 shows MOFs prepared from a CHCl$_3$ solution of L2 and a DMF solution of ZnCl$_2$.2H$_2$O, under the conditions described in Study 3.

A $CHCl_3$ solution (1.0 ml) of L2 (5 mg, 6.8 µmol) was added to a DMF solution (3.0 ml) of $ZnCl_2.2H_2O$ (1.86 mg, 13.6 µmol) in an oven-dried glass pressure tube, which was sealed and heated for 2 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 54).

Figure 55:
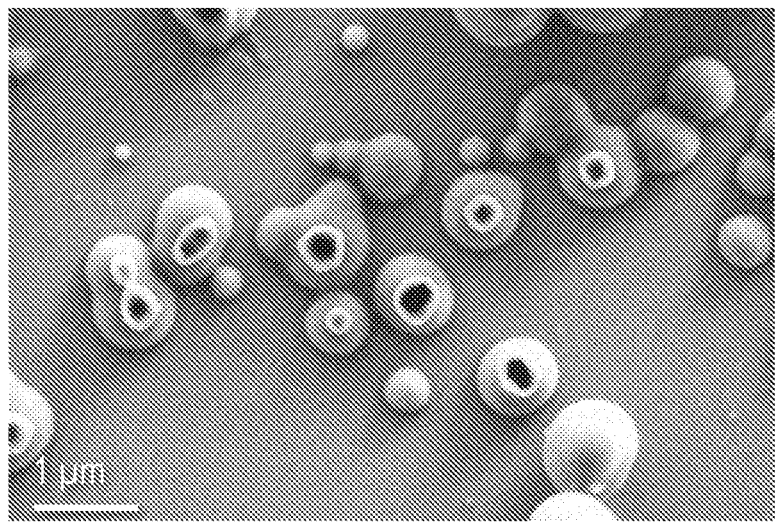
FIG. 55 shows MOFs prepared from a CHCl$_3$ solution of L2 and a DMF solution of ZnCl$_2$.2H$_2$O, under the conditions described in Study 3.

A $CHCl_3$ solution (1.0 ml) of L2 (5 mg, 6.8 µmol) was added to a DMF solution (3.0 ml) of $ZnCl_2.2H_2O$ (1.86 mg, 13.6 µmol) in an oven-dried glass pressure tube, which was sealed and heated for 3 days at 105° C. without stirring and with exclusion of light, followed by subsequent controlled cooling to RT over 9-10 h. at a rate of 10° C./h, resulting in a light white precipitate and was collected by centrifugation of the reaction mixture for ~10 min. at 5000 rpm and decanting the mother liquor (FIG. 55).

Figure 56:
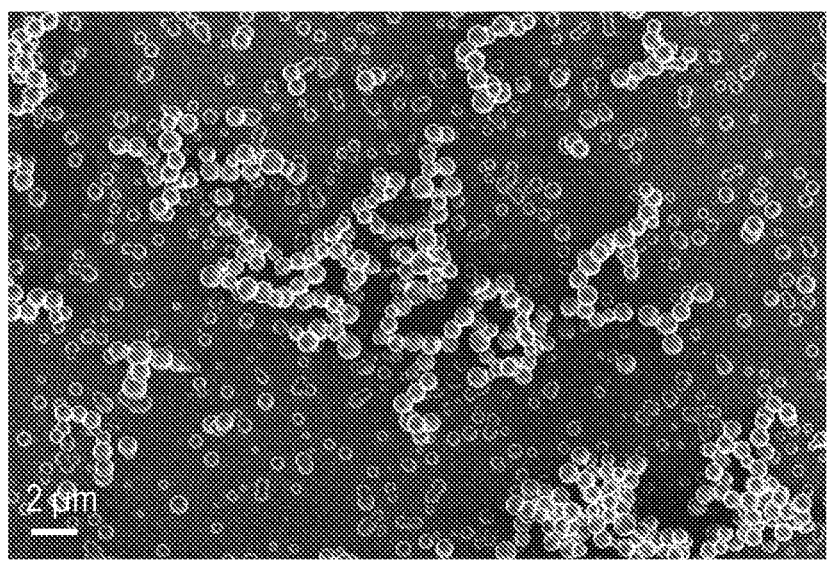
FIG. 56 shows MOFs prepared from a CHCl$_3$ solution of L2 and a DMF solution of ZnBr$_2$, under the conditions described in Study 3.

A CHCl$_3$ solution (1.0 ml) of L2 (5 mg, 6.8 μmol) was added to a DMF solution (3.0 ml) of ZnBr$_2$ (3.1 mg, 13.6 μmol) in an oven-dried glass pressure tube, which was sealed and heated for 2 days at 105° C. without stirring and with exclusion of light, followed by subsequent controlled cooling to RT over 9-10 h. at a rate of 10° C./h, resulting in a white precipitate and was collected by centrifugation of the reaction mixture for ~10 min. at 5000 rpm and decanting the mother liquor (FIG. 56).

APPENDIX

Scheme 1: Chemical structures of the polypyridyl ligands L1-L4

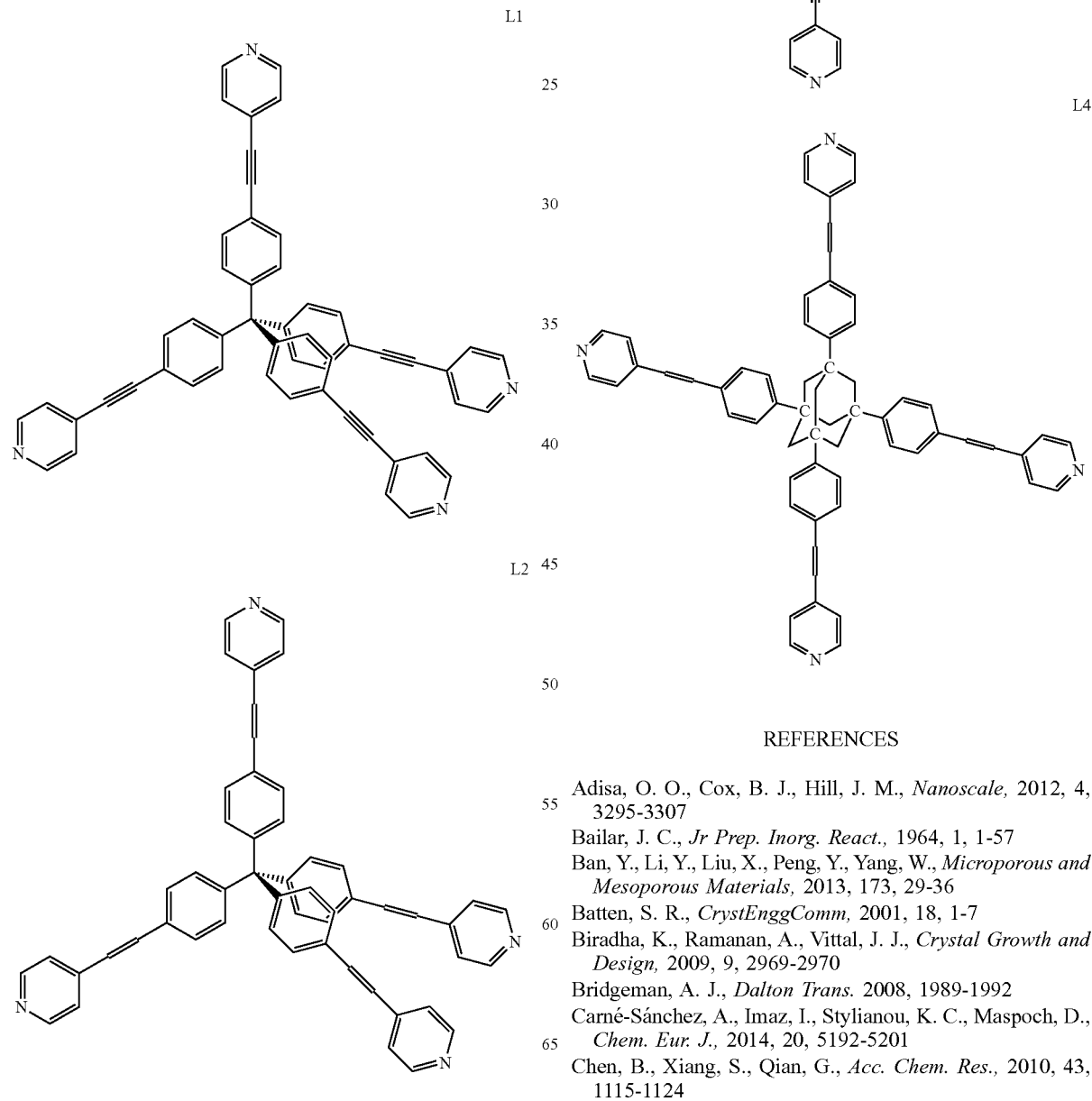

REFERENCES

Adisa, O. O., Cox, B. J., Hill, J. M., *Nanoscale,* 2012, 4, 3295-3307

Bailar, J. C., *Jr Prep. Inorg. React.,* 1964, 1, 1-57

Ban, Y., Li, Y., Liu, X., Peng, Y., Yang, W., *Microporous and Mesoporous Materials,* 2013, 173, 29-36

Batten, S. R., *CrystEnggComm,* 2001, 18, 1-7

Biradha, K., Ramanan, A., Vittal, J. J., *Crystal Growth and Design,* 2009, 9, 2969-2970

Bridgeman, A. J., *Dalton Trans.* 2008, 1989-1992

Carné-Sánchez, A., Imaz, I., Stylianou, K. C., Maspoch, D., *Chem. Eur. J.,* 2014, 20, 5192-5201

Chen, B., Xiang, S., Qian, G., *Acc. Chem. Res.,* 2010, 43, 1115-1124

Cho, W., Lee, H. J; Oh, M., *J. Am. Chem. Soc.*, 2008, 130, 16943-16946

Choudhury, L., Kaminker, R., Motiei, L., de Ruiter, G., Morozov, M., Lupo, F., Gulino, A., van der Boom, M. E., *J. Am. Chem. Soc.*, 2010, 132, 9295

Cook, T. R., Yang, R. Y., Stang, P. J., *Chem. Rev.*, 2013, 113, 734-777

Evans, O. R., Lin, W., Acc. Chem. Res., 2002, 35, 511

Furukawa, H., Cordova, K. E., O'Keeffe, M., Yaghi, O. M., *Science*, 2013, 341, 1230444

Gao, J., Ye, K., Yang, L., Xiong, W. W., Ye, L., Wang, Y., Zhang, Q., *Inorg. Chem.*, 2014, 53, 691-693

Gu, X. W., Loynachan, C. N., Wu, Z., Zhang, Y. W., Srolovitz, D. J., Greer, J. R., *Nano Lett.*, 2012, 12, 6385-6392

Guo, Y. N., Li, Y., Zhi, B., Zhang, D., Liua, Y., Huo, Q., *RSC Adv.*, 2012, 2, 5424-5429

Hasenknopf, B., Lehn, J. M., Baum, G., Fenske, D., *Proc. Natl. Acad. Sci. USA*, 1996, 93, 1397-1400

Jeon, Y. M., Armatas, G. S., Kim, D., Kanatzidis, M. G., Mirkin, C. A., *Small*, 2009, 5, 46-50

Jung, S., Oh, M., *Angew. Chem., Int. Ed.* 2008, 47, 2049-2051

Kaminker, R., Motiei, L., Gulino, A., Fragal, I., Shimon, L. J. W., Evmenenko, G., Dutta, P., Iron, M. A., van der Boom, M. E., *J. Am. Chem. Soc.*, 2010, 132, 14554

Kaminker, R., Popovitz-Biro, R., van der Boom, M. E., *Angew. Chem, Int. Ed.*, 2011, 50, 3224-3226

Kitagawa, S., Kitaura, R., Noro, S., *Angew. Chem., Int. Ed.* 2004, 43, 2334

Kittel, C., Introduction to Solid State Physics. John Wiley and Sons, 1996

Kondo, M., Okubo, T., Asami, A., Noro, S.-i., Yoshitomi, T., Kitagawa, S., Ishii, T., Matsuzaka, H., Seki, K., *Angew. Chem. Int. Ed.* 1999, 38, 140-143

Lei, B. F., Li, B., Zhang, H. R., Zhang, L. M., Li, W. L., *J. Phys. Chem. C*, 2007, 111, 11291

Li, W., Doblinger, M., Vaneski, A., Rogach, A. L., Jackel, F., Feldmann, J., *J. Mat. Chem.*, 2011, 21, 17946-17952

Liu, K., You, H., Jia, G., Zheng, Y., Huang, Y., Song, Y., Yang, M., Zhang, L., Zhang, H., *Crystal Growth and Design*, 2010, 10, 790-797

Long, J. R., Yaghi, O. M., *Chem. Soc. Rev.*, 2009, 38, 1213-1214

Lu, Y., Cao, H., Zhang, S., Zhang, X., *J. Mater. Chem.*, 2011, 21, 8633-8639

Lu, W., Wei, Z., Gu, Z. Y., Liu, T. F., Park, J., Park, J., Tian, J., Zhang, M., Zhang, Q., Gentle III, T., Bosch, M., Zhou, H. C., *Chem. Soc. Rev., DOI:* 10.1039/C4CS00003J (Advance Article)

Manson, J. A., Veenstra, M., Long, J. R., *Chem. Sci.*, 2014, 5, 32-51

Masoomi, M. Y., Morsali, A., *RSC Adv.*, 2013, 3, 19191-19218

Murray, C. B., Sun, S., Daschler, W., Doyle, H., Betley, T. A., Kagen, C. R., *Ibm. J. Res. & Dev.*, 2001, 45, 47-56

Ni, Z., Masel, R. I., *J. Am. Chem. Soc.*, 2006, 128, 12394-12395

Noorduin, W., Grinthal, A., Mahadevan, L., Aizenberg, J., *Science*, 2013, 340, 832-837

Oh, M., Mirkin, C. A., *Nature*, 2005, 438, 651-654

Oh, M., Mirkin, C. A., *Angew. Chem., Int. Ed.* 2006, 45, 5492-5494

Park, K. H., Jang, K., Son, S. U., Sweigart, D. A., *J. Am. Chem. Soc.*, 2006, 128, 8740-8741

Pevzner, A., Engel, Y., Elnathan, R., Tsukernik, A., Barkay, Z., Patolsky, F., *Nano Lett.*, 2012, 12, 7-12

Ranft, A., Betzler, S. B., Haase, F., Lotsch, B. V., *CrystEngComm*, 2013, 15, 9296-9300

Rieter, W. J., Taylor, K. M. L., An, H., Lin, W., Lin, W., *J. Am. Chem. Soc.*, 2006, 128, 9024-9025

Roberts, R. J., Rowe, R. C., York, P., *Powder Technology*, 1991, 65 139-146

Rowsell, J. L C., Yaghi, O. M., *Angew. Chem., Int. Ed.* 2005, 44, 4670

Sader, J. E., Chon, J. W. M., Mulvaney, P., *Rev. Sci. Instrum.*, 1999, 70, 3967

Schilling, C. I., Plietzsch, O., Nieger, M., Muller, T., Brase, S., *Eur. J. Org. Chem.*, 2011, 1743-1754

Seo, J. S., Whang, D., Lee, H., Jun, S. I., Oh, J., Jeon, Y. J., Kim, K., *Nature*, 2000, 404, 982

Shi, N., Xie, L., Sun, H., Duan, J., Yin, G., Xub, Z., Huang, W., *Chem. Commun.*, 2011, 47, 5055-5057

Shirman, T., Lambre, J. F., Shimon, L. J. W., Gupta, T., Martin, J. M. L., van der Boom, M. E., *Cryst. Growth Des.*, 2008, 8, 3066-3072

Sindoro, M., Yanai, N., Jee, A. Y., Granick, S., *Acc. Chem. Res.*, 2014, 47, 459-469

Smulders, M. M., Riddell, I. A., Browne, C., Nitschke, J. R., *Chem. Soc. Rev.*, 2013, 42, 1728-1754

Spokoyny, A. M., Kim, D., Sumrein, A., Mirkin, C. A., *Chem. Soc. Rev.*, 2009, 38, 1218-1227

Stock, N., Biswas, S., *Chem. Rev.*, 2011, 112, 933-969

Sun, X., Dong, S., Wang, E., *J. Am. Chem. Soc.*, 2005, 127, 13102-13103

Tabellion, F. M., Seidel, S. R., Arif, A M., Stang, P. J., *J. Am. Chem. Soc.*, 2001, 123, 7740

Tabor, D., *J. Coll. Int. Sci.* 1977, 58, 2-13

Tao, A. R., Habas, S., Yang, P., *Small*, 2008, 4, 310-325

Thompson, A. M. W. C., Hock, J, McCleverty, J. A., Ward, M. D., *Inorg. Chim. Acta.*, 1997, 256, 331-334

Tomasik, P., Ratajewicz, Z., Newkome, G. R., Strekowski, L. E., In Chemistry of Heterocyclic Compounds: Pyridine Metal Complexes (Part 6, Volume 14). (John Wiley & Sons, Inc., 2008).

Tuxen, A., Carenco, S., Chintapalli, M., Chuang, C. H., Escudero, C., Pach, E., Jiang, P., Borondics, F., Beberwyck, B., Alivisatos, A. P., Thornton, G., Pong, W. F., Guo, J., Perez, R., Besenbacher, F., Salmeron, M., *J. Am. Chem. Soc.*, 2013, 135, 2273-2278

Wang, H., Zeng, Y., Ma, J. S., Fu, H., Yao, J., Mikhaleva, A. I., Trofimov, B. A., *Chem. Commun.*, 2009, 5457-5459

Wang, C., Liu, D., Lin, W., *J. Am. Chem. Soc.*, 2013, 135, 13222-13234

Wei, H., Li, B., Du, Y., Dong, S., Wang, E., *Chem. Mater.*, 2007, 19, 2987-2993

Whitesides, G. M., Grzybowski, B., *Science*, 2002, 295, 2418-2421

Yaghi, O. M., Obkeeffe, M., Ockwig, N. W., Chae, H. K., Eddaoudi, M., Kim, J., *Nature*, 2003, 423, 705

Zhang, W., Jin, W., Fukushima, T., Ishii, N., Aida, T., *Angew. Chem, Int. Ed.*, 2009, 48, 4747-4750

Zhao, X., Xiao, B., Fletcher, A. J., Thomas, K. M., Bradshaw, D., Rosseinsky, M. J., *Science*, 2004, 306, 1012

Zhao, X. Y., Liang, D. D., Liu, S. X., Sun, C. Y., Cao, R. G., Gao, C. Y., Ren, Y. H., Su, Z. M., *Inorg. Chem.*, 2008, 47, 7133

Zhao, D., Timmons, D. J., Yuan, D., Zhou, H. C., *Acc. Chem. Res.*, 2011, 44, 123-133

The invention claimed is:

1. A metal-organic material, having a three-dimensional (3D) crystalline micro or sub-micro structure, comprising at least two ligands, at least two metal ions structurally coordinated with said ligands, and counter anions, wherein each one of the ligands is of the general formula I:

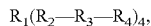

wherein
$R_1$ is C or adamantane-1,3,5,7-tetrayl;
$R_2$ and $R_3$ each independently is absent, or selected from $(C_1$-$C_8)$alkylene, $(C_2$-$C_8)$alkenylene, $(C_2$-$C_8)$alkynylene, cycloalkylene, heterocycloalkylene, arylene-diyl, heteroarylene-diyl, or —N═N—, wherein said alkylene, alkenylene, alkynylene, cycloalkylene, heterocycloalkylene, arylene-diyl and heteroarylene-diyl may optionally be substituted with one or more groups each independently selected from halogen, —$OR_6$, —CN, —$COR_6$, —$COOR_6$, —$CON(R_6)_2$, —$OCOOR_6$, —$OCON(R_6)_2$, —$(C_1$-$C_4)$alkyl, —O—$(C_1$-$C_4)$alkyl, —$(C_1$-$C_4)$alkylene-$COOR_6$, —$N(R_6)_2$, —$NO_2$, —$SR_6$, —$SO_2R_6$, or —S(═O)$R_6$, or said alkylene, alkenylene and alkynylene may optionally be interrupted by one or more identical or different heteroatoms selected from S, O or N, and/or at least one group selected from —N═N—, —NH—CO—, —CO—NH—, —N$(C_1$-$C_4$alkyl)-, —N$(C_6$-$C_{10}$aryl)-, or —$(C_6$-$C_{10})$arylene-diyl-, wherein $R_6$ each independently is H, $(C_1$-$C_4)$alkyl, $(C_2$-$C_4)$alkenyl or $(C_2$-$C_4)$alkynyl;
$R_4$ each independently is a pyridyl of the formula II, 2,2'-bipyridyl of the formula III, or 2,2':6',2''-terpyridyl of the formula IV, linked through a carbon atom thereof; and

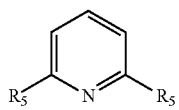
II

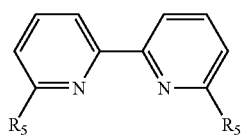
III

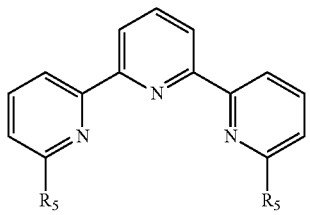
III $R_5$ each independently is H, —COOH, —CN, —OH, or —$NH_2$.

2. The metal-organic material of claim 1, wherein $R_2$ and $R_3$ each independently is absent, or selected from $(C_1$-$C_8)$alkylene, $(C_2$-$C_8)$alkenylene, $(C_2$-$C_8)$alkynylene, cycloalkylene, heterocycloalkylene, arylene-diyl, heteroarylene-diyl, or —N═N—, wherein said alkylene, alkenylene, alkynylene, cycloalkylene, heterocycloalkylene, arylene-diyl and heteroarylene-diyl may optionally be substituted with one or more groups each independently selected from halogen, —OH, —CN, —COH, —COOH, —$CONH_2$, —OCOOH, —$OCONH_2$, —$(C_1$-$C_4)$alkyl, —O—$(C_1$-$C_4)$alkyl, —$(C_1$-$C_4)$alkylene-COOH, —$NH_2$, —$NO_2$, —SH, —$SO_2H$, or —S(═O)H, or said alkylene, alkenylene and alkynylene may optionally be interrupted by one or more identical or different heteroatoms selected from S, O or N, and/or at least one group selected from —N═N—, —NH—CO—, —CO—NH—, —N$(C_1$-$C_4$alkyl)-, —N$(C_6$-$C_{10}$aryl)-, or —$(C_6$-$C_{10})$arylene-diyl-.

3. The metal-organic material of claim 2, wherein $R_2$ and $R_3$ each independently is absent, or selected from $(C_1$-$C_4)$alkylene, $(C_2$-$C_4)$alkenylene, $(C_2$-$C_4)$alkynylene, cycloalkylene, heterocycloalkylene, arylene-diyl, heteroarylene-diyl, or —N═N—, wherein said alkylene, alkenylene, alkynylene, cycloalkylene, heterocycloalkylene, arylene-diyl and heteroarylene-diyl may optionally be substituted with halogen, —OH, —CN, —COH, —COOH, —$CONH_2$, —OCOOH, —$OCONH_2$, —$(C_1$-$C_2)$alkyl, —O—$(C_1$-$C_2)$alkyl, —$(C_1$-$C_2)$alkylene-COOH, —$NH_2$, —$NO_2$, —SH, —$SO_2H$, or —S(═O)H, or said alkylene, alkenylene and alkynylene may optionally be interrupted by one or more identical or different heteroatoms selected from S, O or N, and/or at least one group selected from —N═N—, —NH—CO—, —CO—NH—, —N$(C_1$-$C_2$alkyl)-, —N$(C_6$aryl)-, or —$(C_6)$arylene-diyl-.

4. The metal-organic material of claim 3, wherein $R_2$ and $R_3$ each independently is absent, or selected from $(C_1$-$C_4)$alkylene, $(C_2$-$C_4)$alkenylene, $(C_2$-$C_4)$alkynylene, arylene-diyl, or heteroarylene-diyl.

5. The metal-organic material of claim 4, wherein (i) one of $R_2$ and $R_3$ is absent and another of $R_2$ and $R_3$ is $(C_2$-$C_4)$alkylene, $(C_2$-$C_4)$alkenylene, $(C_2$-$C_4)$alkynylene, arylene-diyl, or heteroarylene-diyl; (ii) one of $R_2$ and $R_3$ is $(C_2$-$C_4)$alkylene, $(C_2$-$C_4)$alkenylene or $(C_2$-$C_4)$alkynylene, and another of $R_2$ and $R_3$ is arylene-diyl, or heteroarylene-diyl; or (iii) both $R_2$ and $R_3$ are absent.

6. The metal-organic material of claim 5, wherein $R_2$ is $(C_2$-$C_4)$alkenylene or $(C_2$-$C_4)$alkynylene, and $R_3$ is $(C_6)$arylene-diyl; or $R_2$ is $(C_6)$arylene-diyl, and $R_3$ is $(C_2$-$C_4)$alkenylene or $(C_2$-$C_4)$alkynylene.

7. The metal-organic material of claim 1, wherein $R_4$ each independently is a pyridyl of the formula II, wherein $R_5$ each independently is H, —COOH, —CN, —OH, or —$NH_2$, preferably H or —COOH.

8. The metal-organic material of claim 1,
wherein
$R_1$ is C or adamantane-1,3,5,7-tetrayl;
$R_2$ and $R_3$ each independently is absent, or selected from $(C_1$-$C_4)$alkylene, $(C_2$-$C_4)$alkenylene, $(C_2$-$C_4)$alkynylene, cycloalkylene, heterocycloalkylene, arylene-diyl, heteroarylene-diyl, or —N═N—, wherein said alkylene, alkenylene, alkynylene, cycloalkylene, heterocycloalkylene, arylene-diyl and heteroarylene-diyl may optionally be substituted with one or more groups each independently selected from halogen, —OH, —CN, —COH, —COOH, —$CONH_2$, —OCOOH, —$OCONH_2$, —$(C_1$-$C_2)$alkyl, —O—$(C_1$-$C_2)$alkyl, —$(C_1$-$C_2)$alkylene-COOH, —$NH_2$, —$NO_2$, —SH, —$SO_2H$, or —S(═O)H, or said alkylene, alkenylene and alkynylene may optionally be interrupted by one or more identical or different heteroatoms selected from S, O or N, and/or at least one group selected from —N═N—, —NH—CO—, —CO—NH—, —N$(C_1$-$C_2$alkyl)-, —N$(C_6$aryl)-, or —$(C_6)$arylene-diyl-;
$R_4$ each independently is pyridyl of the formula II; and
$R_5$ each independently is H, —COOH, —CN, —OH, or —$NH_2$, preferably H or —COOH.

9. The metal-organic material of claim 8, wherein $R_2$ and $R_3$ each independently is absent, or selected from $(C_1$-$C_4)$alkylene, $(C_2$-$C_4)$alkenylene, $(C_2$-$C_4)$alkynylene, arylene-diyl, or heteroarylene-diyl; $R_4$ is a pyridyl of the formula II linked through the carbon atom para to the nitrogen atom; and $R_5$ is H or —COOH.

10. The metal-organic material of claim 9, wherein (i) one of $R_2$ and $R_3$ is absent and another of $R_2$ and $R_3$ is $(C_2-C_4)$ alkylene, $(C_2-C_4)$alkenylene, $(C_2-C_4)$alkynylene, arylene-diyl, or heteroarylene-diyl; (ii) one of $R_2$ and $R_3$ is $(C_2-C_4)$ alkylene, $(C_2-C_4)$alkenylene or $(C_2-C_4)$alkynylene, and another of $R_2$ and $R_3$ is arylene-diyl, or heteroarylene-diyl; or (iii) both $R_2$ and $R_3$ are absent.

11. The metal-organic material of claim 10, wherein $R_2$ is $(C_2-C_4)$alkenylene or $(C_2-C_4)$alkynylene, and $R_3$ is $(C_6)$ arylene-diyl; or $R_2$ is $(C_6)$arylene-diyl, and $R_3$ is $(C_2-C_4)$ alkenylene or $(C_2-C_4)$alkynylene.

12. The metal-organic material of claim 11, wherein $R_2$ is $(C_6)$arylene-diyl; and $R_3$ is $(C_2)$alkenylene or $(C_2)$alkynylene.

13. The metal-organic material of claim 12, wherein:
(i) $R_1$ is C, and each one of said ligands is tetrakis(4-(pyridin-4-ylethynyl) phenyl)methane or tetrakis(4-(2-(pyridin-4-yl) vinyl)phenyl) methane, herein identified ligands L1 and L2, respectively; or
(ii) $R_1$ is adamantane-1,3,5,7-tetrayl, and each one of said ligands is 1,3,5,7-tetrakis(4-(pyridin-4-ylethynyl)phenyl)adamantane or 1,3,5,7-tetrakis(4-(2-(pyridin-4-yl) vinyl)phenyl)adamantane, herein identified ligands L3 and L4, respectively.

14. The metal-organic material of claim 1, wherein said metal ions are ions of a transition metals selected from Os, Ru, Fe, Pt, Pd, Ni, Ir, Rh, Zn, Co, Cu, Re, Tc, Mn, V, Nb, Ta, Hf, Zr, Cr, Mo, W, Ti, Sc, Ag, Au, Y, or a combination thereof.

15. The metal-organic material of claim 14, wherein said transition metal is Ni, Cu, Pd, Zn, or a combination thereof.

16. The metal-organic material of claim 1, wherein said counter anions are selected from inorganic anions, organic anions, or a combination thereof.

17. The metal-organic material of claim 16, wherein said inorganic anions are selected from $Cl^-$, $Br^-$, $I^-$, $NO_3^-$, $PF_6^-$, $BF_4^-$, $OH^-$, $ClO_4^-$, $SO_3^-$, or $CN^-$; and said organic anions are selected form alkylCOO$^-$, preferably acetoxy (OAc), $CF_3COO^-$, arylCOO$^-$, trifluoromethanesulfonate (triflate, OTf), citrate.

18. The metal-organic material of claim 1, wherein at least one of said metal ions is structurally coordinated between two of said at least two ligands.

19. The metal-organic material of claim 1, wherein said crystalline micro or sub-micro structure has a geometrical shape.

20. The metal-organic material of claim 13, comprising ligands each being the herein identified ligand L1 and transition metal ions structurally coordinated with nitrogen atoms of said ligands, wherein:
(i) said transition metal ions are Ni(II) ions, said counter anions are $Cl^-$, and said metal-organic material has the chemical formula $(NiCl_2N_2C_{26.5}H_{16})_n$(solvents)$_m$; or
(ii) said transition metal ions are Ni(II) ions, said counter anions are $Br^-$, and said metal-organic material has the chemical formula $(NiBr_2N_2C_{26.5}H_{16})_n$(solvents)$_m$,
wherein n is an integer of at least 4, and said metal-organic material has a 3D crystalline micro or sub-micro structure optionally further comprising solvent molecules, wherein (m≥0).

21. The metal-organic material of claim 13, comprising ligands each being the herein identified ligand L2 and transition metal ions structurally coordinated with nitrogen atoms of said ligands, wherein:
(i) said transition metal ions are Ni(II) ions, said counter anions are $Cl^-$, and said metal-organic material has the chemical formula $(NiCl_2N_2C_{26.5}H_{20})_n$(solvents)$_m$;
(i) said transition metal ions are Ni(II) ions, said counter anions are $Br^-$, and said metal-organic material has the chemical formula $(NiBr_2N_2C_{26.5}H_{20})_n$(solvents)$_m$;
(ii) said transition metal ions are Cu(II) ions, said counter anions are $Cl^-$, and said metal-organic material has the chemical formula $(CuCl_2N_2C_{26.5}H_{20})_n$(solvents)$_m$;
(iii) said transition metal ions are Cu(II) ions, said counter anions are $Br^-$, and said metal-organic material has the chemical formula $(CuBr_2N_2C_{26.5}H_{20})_n$(solvents)$_m$;
(iv) said transition metal ions are Cu(II) ions, said counter anions are $NO_3^-$, and said metal-organic material has the chemical formula $(Cu(NO_3)_2N_2C_{26.5}H_{20})_n$(solvents)$_m$;
(v) said transition metal ions are Cu(II) ions, said counter anions are $OTf^-$, and said metal-organic material has the chemical formula $(Cu(OTf)_2N_2C_{26.5}H_{20})_n$(solvents)$_m$;
(vi) said transition metal ions are Pd(II) ions, said counter anions are $Cl^-$, and said metal-organic material has the chemical formula $(PdCl_2N_2C_{26.5}H_{20})_n$(solvents)$_m$;
(vii) said transition metal ions are Zn(II) ions, said counter anions are $OAc^-$, and said metal-organic material has the chemical formula $(Zn(OAc)_2N_2C_{26.5}H_{20})_n$(solvents)$_m$;
(viii) said transition metal ions are Zn(II) ions, said counter anions are $Cl^-$, and said metal-organic material has the chemical formula $(ZnCl_2N_2C_{26.5}H_{20})_n$(solvents)$_m$; or
(ix) said transition metal ions are Zn(II) ions, said counter anions are $Br^-$, and said metal-organic material has the chemical formula $(ZnBr_2N_2C_{26.5}H_{20})_n$(solvents)$_m$,
wherein n is an integer of at least 4, and said metal-organic material has a 3D crystalline micro or sub-micro structure optionally further comprising solvent molecules, wherein (m≥0).

22. A method for the preparation of a metal-organic material according to claim 1, comprising the steps of:
(i) providing (a) an organic solution or suspension of a metal salt consisting of anions and said metal ions; and (b) an organic solution or suspension of said ligands, in a pressure vessel such as a sealable glass pressure tube;
(ii) sealing and keeping said pressure vessel for a period of time with exclusion of light and without stirring, thereby reacting said metal ions with said ligands to obtain said metal-organic material as a precipitate; and
(iii) collecting said precipitate;
wherein step (ii) is carried out while heating said pressure vessel to a temperature ranging from 60° C. to 120° C., for the whole said period of time or a part thereof, and then gradually cooling said pressure vessel.

23. The method of claim 22, wherein said pressure vessel is a glass pressure vessel or glass pressure tube.

24. The method of claim 22, wherein the organic solvent in said organic solution or suspension each independently is chloroform, dimethylformamide (DMF), an alkanol, DMSO, acetonitrile, ethylene glycol, toluene, benzene, ethylbenzene, ether (diethyl ether), or an alkane.

25. The method of claim 22, wherein said period of time in step (ii) is from about 1 to about 10 days or more.

26. The method of claim 22, wherein steps (i)-(ii) are carried out under inert conditions.

27. The method of claim 22, wherein the metal-organic material obtained has a three-dimensional crystalline micro or sub-micro structure.

28. The method of claim 27, wherein said crystalline micro or sub-micro structure has a geometrical shape.

29. The method of claim 28, wherein said geometrical shape is affected by reaction components and/or the reaction conditions or parameters in steps (ii).

30. The method of claim 29, wherein said reaction components are one or more of said metal ions, anions, and organic solvents; and said reaction conditions or parameters are one or more of said temperature, period of time, and cooling rate.

31. A process for gas adsorption, gas separation, gas purification or gas storage, comprising the steps of:
providing an adsorbent comprising the metal-organic material according to claim 1; and
adsorbing said gas to said adsorbent.

* * * * *